United States Patent
Goraltchouk et al.

(10) Patent No.: US 9,125,647 B2
(45) Date of Patent: Sep. 8, 2015

(54) METHOD AND APPARATUS FOR ELEVATING RETAINERS ON SELF-RETAINING SUTURES

(75) Inventors: Alexei Goraltchouk, Richmond (CA); Robert A. Herrmann, Vancouver (CA); Lev Drubetsky, Coquitlam (CA); Jeffrey Mendel Gross, Vancouver (CA); William L. D'Agostino, Hamden, CT (US); Carlos Gonzalez Resendiz, Richmond (CA)

(73) Assignee: Ethicon, Inc., Somerville, NJ (US)

( * ) Notice: Subject to any disclaimer, the term of this patent is extended or adjusted under 35 U.S.C. 154(b) by 620 days.

(21) Appl. No.: 12/866,027

(22) PCT Filed: Feb. 20, 2009

(86) PCT No.: PCT/US2009/034703
§ 371 (c)(1),
(2), (4) Date: Nov. 8, 2010

(87) PCT Pub. No.: WO2009/105663
PCT Pub. Date: Aug. 27, 2009

(65) Prior Publication Data
US 2011/0046669 A1 Feb. 24, 2011

Related U.S. Application Data

(60) Provisional application No. 61/030,423, filed on Feb. 21, 2008, provisional application No. 61/030,391, filed on Feb. 21, 2008.

(51) Int. Cl.
*A61B 17/04* (2006.01)
*A61B 17/06* (2006.01)
(Continued)

(52) U.S. Cl.
CPC ............. *A61B 17/06166* (2013.01); *D02J 3/10* (2013.01); *A61B 2017/00526* (2013.01);
(Continued)

(58) Field of Classification Search
CPC ............. A61B 17/06166; A61B 2017/00526; A61B 2017/00871; A61B 2017/06176; D02J 3/10; Y10T 83/02
USPC ................. 606/228; 83/13–56; 428/357–401; 29/7.1–7.3
See application file for complete search history.

(56) References Cited

U.S. PATENT DOCUMENTS

| 709,392 A | 9/1902 | Brown |
| 733,723 A | 7/1903 | Lukens |

(Continued)

FOREIGN PATENT DOCUMENTS

| BE | 1014364 | 9/2003 |
| CA | 2309844 | 12/1996 |

(Continued)

OTHER PUBLICATIONS

Bacci, Pier Antonio, "Chirurgia Estetica Mini Invasiva Con Fili Di Sostegno", Collana di Arti, Pensiero e Scienza; Minelli Editore—2006; 54 pgs.

(Continued)

*Primary Examiner* — Alexander Orkin

(57) ABSTRACT

A method and device to elevate retainers on a suture thread to a desired angle such that the retainers can retain the desired elevation. The retainers can be elevated using an apparatus having at least one roller and at least one bending bar, wherein the bending bar contacts the retainers adjacent to the at least one roller to apply a force to the retainers. The retainers can also be elevated using a tube-shaped apparatus. A suture can be made up of an inner core and a coating that upon a stimuli increases the protrusion of the retainers away from the suture core. A coating can be inserted into the cut associated with the retainer and repulsive or expansive forces result in a pushing out of the cut and distending of the retainers away from the suture core.

18 Claims, 41 Drawing Sheets

(51) Int. Cl.
*D02J 3/10* (2006.01)
*A61B 17/00* (2006.01)

(52) U.S. Cl.
CPC .............. *A61B 2017/00867* (2013.01); *A61B 2017/00871* (2013.01); *A61B 2017/00995* (2013.01); *A61B 2017/06176* (2013.01); *Y10T 83/02* (2015.04)

(56) References Cited

U.S. PATENT DOCUMENTS

| | | | |
|---|---|---|---|
| 816,026 A | 3/1906 | Meier | |
| 1,142,510 A | 6/1915 | Engle | |
| 1,728,316 A | 9/1929 | Von Wachenfeldt | |
| 1,886,721 A | 11/1932 | O'Brien | |
| 2,094,578 A | 10/1937 | Blumenthal et al. | |
| 2,201,610 A | 5/1940 | Dawson, Jr. | |
| 2,232,142 A | 2/1941 | Schumann | |
| 2,254,620 A | 9/1941 | Miller | |
| 2,347,956 A | 5/1944 | Lansing | |
| 2,355,907 A | 8/1944 | Cox | |
| 2,421,193 A | 5/1947 | Gardner | |
| 2,452,734 A | 11/1948 | Costelow | |
| 2,472,009 A | 5/1949 | Gardner | |
| 2,480,271 A | 8/1949 | Sumner | |
| 2,572,936 A | 10/1951 | Kulp et al. | |
| 2,684,070 A | 7/1954 | Kelsey | |
| 2,736,964 A | 3/1956 | Lieberman | |
| 2,779,083 A | 1/1957 | Enton | |
| 2,817,339 A | 12/1957 | Sullivan | |
| 2,830,366 A | 4/1958 | Chisena | |
| 2,866,256 A | 12/1958 | Matlin | |
| 2,910,067 A | 10/1959 | White | |
| 2,928,395 A | 3/1960 | Forbes et al. | |
| 2,988,028 A | 6/1961 | Alcamo | |
| 3,003,155 A | 10/1961 | Mielzynski et al. | |
| 3,066,452 A | 12/1962 | Bott et al. | |
| 3,066,673 A | 12/1962 | Bott et al. | |
| 3,068,869 A | 12/1962 | Shelden et al. | |
| 3,068,870 A | 12/1962 | Levin | |
| 3,082,523 A | 3/1963 | Modes et al. | |
| 3,123,077 A | 3/1964 | Alcamo | |
| 3,166,072 A | 1/1965 | Sullivan, Jr. | |
| 3,187,752 A | 6/1965 | Glick | |
| 3,206,018 A | 9/1965 | Lewis et al. | |
| 3,209,652 A | 10/1965 | Burgsmueller | |
| 3,209,754 A | 10/1965 | Brown | |
| 3,212,187 A | 10/1965 | Benedict | |
| 3,214,810 A | 11/1965 | Mathison | |
| 3,221,746 A | 12/1965 | Noble | |
| 3,234,636 A | 2/1966 | Brown | |
| 3,273,562 A | 9/1966 | Brown | |
| 3,352,191 A | 11/1967 | Crawford | |
| 3,378,010 A | 4/1968 | Codling | |
| 3,385,299 A | 5/1968 | LeRoy | |
| 3,494,006 A | 2/1970 | Brumlik | |
| 3,522,637 A | 8/1970 | Brumlik | |
| 3,525,340 A | 8/1970 | Gilbert | |
| 3,545,608 A | 12/1970 | Berger et al. | |
| 3,557,795 A | 1/1971 | Hirsch | |
| 3,570,497 A | 3/1971 | Lemole | |
| 3,586,002 A | 6/1971 | Wood | |
| 3,608,095 A | 9/1971 | Barry | |
| 3,608,539 A | 9/1971 | Miller | |
| 3,618,447 A | 11/1971 | Goins | |
| 3,646,615 A | 3/1972 | Ness | |
| 3,683,926 A | 8/1972 | Suzuki | |
| 3,716,058 A | 2/1973 | Tanner, Jr. | |
| 3,720,055 A | 3/1973 | de Mestral et al. | |
| 3,748,701 A | 7/1973 | De Mestral | |
| 3,762,418 A | 10/1973 | Wasson | |
| 3,825,010 A | 7/1974 | McDonald | |
| 3,833,972 A | 9/1974 | Brumlik | |
| 3,845,641 A | 11/1974 | Waller | |
| 3,847,156 A | 11/1974 | Trumble | |
| 3,889,322 A | 6/1975 | Brumlik | |
| 3,918,455 A | 11/1975 | Coplan | |
| 3,922,455 A | 11/1975 | Brumlik | |
| 3,941,164 A | 3/1976 | Musgrave | |
| 3,977,937 A * | 8/1976 | Candor | 162/192 |
| 3,980,177 A | 9/1976 | McGregor | |
| 3,981,051 A | 9/1976 | Brumlik | |
| 3,981,307 A | 9/1976 | Borysko | |
| 3,985,138 A | 10/1976 | Jarvik | |
| 3,990,144 A | 11/1976 | Schwartz | |
| 4,006,747 A | 2/1977 | Kronenthal | |
| 4,008,303 A | 2/1977 | Glick et al. | |
| 4,027,608 A | 6/1977 | Arbuckle | |
| 4,043,344 A | 8/1977 | Landi | |
| 4,052,988 A | 10/1977 | Doddi et al. | |
| D246,911 S | 1/1978 | Bess, Jr. et al. | |
| 4,069,825 A | 1/1978 | Akiyama | |
| 4,073,298 A | 2/1978 | Le Roy | |
| 4,137,921 A | 2/1979 | Okuzumi et al. | |
| 4,182,340 A | 1/1980 | Spencer | |
| 4,186,239 A | 1/1980 | Mize et al. | |
| 4,198,734 A | 4/1980 | Brumlik | |
| 4,204,541 A | 5/1980 | Kapitanov | |
| 4,204,542 A | 5/1980 | Bokros et al. | |
| 4,259,959 A | 4/1981 | Walker | |
| 4,278,374 A | 7/1981 | Wolosianski | |
| 4,300,424 A | 11/1981 | Flinn | |
| 4,311,002 A | 1/1982 | Hoffmann et al. | |
| 4,313,448 A | 2/1982 | Stokes | |
| 4,316,469 A | 2/1982 | Kapitanov | |
| 4,317,451 A | 3/1982 | Cerwin et al. | |
| 4,372,293 A | 2/1983 | Vijil-Rosales | |
| 4,428,376 A | 1/1984 | Mericle | |
| 4,430,998 A | 2/1984 | Harvey | |
| 4,434,796 A | 3/1984 | Karapetian | |
| 4,449,298 A | 5/1984 | Patz | |
| 4,454,875 A | 6/1984 | Pratt et al. | |
| 4,467,805 A | 8/1984 | Fukuda | |
| 4,490,326 A | 12/1984 | Beroff et al. | |
| 4,492,075 A | 1/1985 | Faure | |
| 4,493,323 A | 1/1985 | Albright et al. | |
| 4,505,274 A | 3/1985 | Speelman | |
| 4,510,934 A | 4/1985 | Batra | |
| 4,531,522 A | 7/1985 | Bedi et al. | |
| 4,532,926 A | 8/1985 | O'Holla | |
| 4,535,772 A | 8/1985 | Sheehan | |
| 4,548,202 A | 10/1985 | Duncan | |
| 4,553,544 A | 11/1985 | Nomoto et al. | |
| 4,610,250 A | 9/1986 | Green | |
| 4,610,251 A | 9/1986 | Kumar | |
| 4,635,637 A | 1/1987 | Schreiber | |
| 4,637,380 A | 1/1987 | Orejola | |
| 4,653,486 A | 3/1987 | Coker | |
| 4,669,473 A | 6/1987 | Richards et al. | |
| 4,676,245 A | 6/1987 | Fukuda | |
| 4,689,882 A | 9/1987 | Lorenz | |
| 4,702,250 A | 10/1987 | Ovil et al. | |
| 4,712,553 A | 12/1987 | MacGregor | |
| 4,719,917 A | 1/1988 | Barrows et al. | |
| 4,741,330 A | 5/1988 | Hayhurst | |
| 4,750,910 A | 6/1988 | Takayanagi et al. | |
| 4,776,337 A | 10/1988 | Palmaz | |
| 4,832,025 A | 5/1989 | Coates | |
| 4,841,960 A | 6/1989 | Garner | |
| 4,865,026 A | 9/1989 | Barrett | |
| 4,873,976 A | 10/1989 | Schreiber | |
| 4,887,601 A | 12/1989 | Richards | |
| 4,895,148 A | 1/1990 | Bays et al. | |
| 4,898,156 A | 2/1990 | Gatturna et al. | |
| 4,899,743 A | 2/1990 | Nicholson et al. | |
| 4,900,605 A | 2/1990 | Thorgersen et al. | |
| 4,905,367 A | 3/1990 | Pinchuk et al. | |
| 4,930,945 A | 6/1990 | Arai et al. | |
| 4,932,962 A | 6/1990 | Yoon et al. | |
| 4,946,468 A | 8/1990 | Li | |
| 4,948,444 A | 8/1990 | Schultz et al. | |
| 4,950,258 A | 8/1990 | Kawai et al. | |
| 4,950,285 A | 8/1990 | Wilk | |
| 4,968,315 A | 11/1990 | Gatturna | |

(56) References Cited

U.S. PATENT DOCUMENTS

| | | | |
|---|---|---|---|
| 4,976,715 | A | 12/1990 | Bays et al. |
| 4,979,956 | A | 12/1990 | Silvestrini et al. |
| 4,981,149 | A | 1/1991 | Yoon |
| 4,994,073 | A | 2/1991 | Green |
| 4,994,084 | A | 2/1991 | Brennan |
| 4,997,439 | A | 3/1991 | Chen |
| 5,002,550 | A | 3/1991 | Li |
| 5,002,562 | A | 3/1991 | Oberlander |
| 5,007,921 | A | 4/1991 | Brown |
| 5,007,922 | A | 4/1991 | Chen et al. |
| 5,026,390 | A | 6/1991 | Brown |
| 5,037,422 | A | 8/1991 | Hayhurst et al. |
| 5,037,433 | A | 8/1991 | Wilk et al. |
| 5,041,129 | A | 8/1991 | Hayhurst et al. |
| 5,046,513 | A | 9/1991 | Gatturna et al. |
| 5,047,047 | A | 9/1991 | Yoon |
| 5,053,047 | A | 10/1991 | Yoon |
| 5,084,063 | A | 1/1992 | Korthoff |
| 5,089,010 | A | 2/1992 | Korthoff |
| 5,102,418 | A | 4/1992 | Granger et al. |
| 5,102,421 | A | 4/1992 | Anpach, Jr. |
| 5,103,073 | A | 4/1992 | Danilov et al. |
| 5,112,344 | A | 5/1992 | Petros |
| 5,123,911 | A | 6/1992 | Granger et al. |
| 5,123,913 | A | 6/1992 | Wilk et al. |
| 5,123,919 | A | 6/1992 | Sauter et al. |
| 5,127,413 | A | 7/1992 | Ebert |
| 5,133,738 | A | 7/1992 | Korthoff et al. |
| 5,141,520 | A | 8/1992 | Goble et al. |
| 5,147,382 | A | 9/1992 | Gertzman et al. |
| 5,156,615 | A | 10/1992 | Korthoff et al. |
| 5,156,788 | A | 10/1992 | Chesterfield et al. |
| 5,176,692 | A | 1/1993 | Wilk et al. |
| 5,179,964 | A | 1/1993 | Cook |
| 5,192,274 | A | 3/1993 | Bierman |
| 5,192,302 | A | 3/1993 | Kensey et al. |
| 5,192,303 | A | 3/1993 | Gatturna et al. |
| 5,197,597 | A | 3/1993 | Leary et al. |
| 5,201,326 | A | 4/1993 | Kubicki et al. |
| 5,207,679 | A | 5/1993 | Li |
| 5,207,694 | A | 5/1993 | Broome |
| 5,217,486 | A | 6/1993 | Rice et al. |
| 5,217,494 | A | 6/1993 | Coggins et al. |
| 5,222,508 | A | 6/1993 | Contarini |
| 5,222,976 | A | 6/1993 | Yoon |
| 5,224,946 | A | 7/1993 | Hayhurst et al. |
| 5,234,006 | A | 8/1993 | Eaton et al. |
| 5,242,457 | A | 9/1993 | Akopov et al. |
| 5,246,441 | A | 9/1993 | Ross et al. |
| 5,259,846 | A | 11/1993 | Granger et al. |
| 5,263,973 | A | 11/1993 | Cook |
| 5,269,783 | A | 12/1993 | Sander |
| 5,282,832 | A | 2/1994 | Toso et al. |
| 5,292,326 | A | 3/1994 | Green |
| 5,306,288 | A | 4/1994 | Granger et al. |
| 5,306,290 | A | 4/1994 | Martins et al. |
| 5,320,629 | A | 6/1994 | Noda et al. |
| 5,330,488 | A | 7/1994 | Goldrath |
| 5,330,503 | A | 7/1994 | Yoon |
| 5,342,376 | A | 8/1994 | Ruff |
| 5,342,395 | A | 8/1994 | Jarrett et al. |
| 5,350,385 | A | 9/1994 | Christy |
| 5,352,515 | A | 10/1994 | Jarrett et al. |
| 5,354,271 | A | 10/1994 | Voda |
| 5,354,298 | A | 10/1994 | Lee et al. |
| 5,358,511 | A | 10/1994 | Gatturna et al. |
| 5,363,556 | A | 11/1994 | Banholzer et al. |
| 5,372,146 | A | 12/1994 | Branch |
| 5,374,268 | A | 12/1994 | Sander |
| 5,374,278 | A | 12/1994 | Chesterfield et al. |
| 5,380,334 | A | 1/1995 | Torrie et al. |
| 5,391,173 | A | 2/1995 | Wilk |
| 5,403,346 | A | 4/1995 | Loeser |
| 5,411,523 | A | 5/1995 | Goble |
| 5,414,988 | A | 5/1995 | DiPalma et al. |
| 5,417,691 | A | 5/1995 | Hayhurst |
| 5,425,746 | A | 6/1995 | Proto et al. |
| 5,425,747 | A | 6/1995 | Brotz |
| 5,437,680 | A | 8/1995 | Yoon et al. |
| 5,450,860 | A | 9/1995 | O'Connor |
| 5,451,461 | A | 9/1995 | Broyer |
| 5,462,561 | A | 10/1995 | Voda |
| 5,464,426 | A | 11/1995 | Bonutti |
| 5,464,427 | A | 11/1995 | Curtis et al. |
| 5,472,452 | A | 12/1995 | Trott |
| 5,478,353 | A | 12/1995 | Yoon |
| 5,480,403 | A | 1/1996 | Lee et al. |
| 5,480,411 | A | 1/1996 | Liu et al. |
| 5,484,451 | A | 1/1996 | Akopov et al. |
| 5,486,197 | A | 1/1996 | Le et al. |
| 5,500,000 | A | 3/1996 | Feagin et al. |
| 5,500,991 | A | 3/1996 | Demarest et al. |
| 5,520,084 | A | 5/1996 | Chesterfield et al. |
| 5,520,691 | A | 5/1996 | Branch |
| 5,522,845 | A | 6/1996 | Wenstrom, Jr. |
| 5,527,342 | A | 6/1996 | Pietrzak et al. |
| 5,531,760 | A | 7/1996 | Alwafaie |
| 5,531,761 | A | 7/1996 | Yoon |
| 5,531,790 | A | 7/1996 | Frechet et al. |
| 5,536,582 | A | 7/1996 | Prasad et al. |
| 5,540,705 | A | 7/1996 | Meade et al. |
| 5,540,718 | A | 7/1996 | Bartlett |
| 5,545,148 | A | 8/1996 | Wurster |
| 5,549,631 | A | 8/1996 | Bonutti |
| 5,554,171 | A | 9/1996 | Gatturna et al. |
| 5,569,272 | A | 10/1996 | Reed et al. |
| 5,571,139 | A | 11/1996 | Jenkins, Jr. |
| 5,571,175 | A | 11/1996 | Vanney et al. |
| 5,571,216 | A | 11/1996 | Anderson |
| 5,573,543 | A | 11/1996 | Akopov et al. |
| 5,584,859 | A | 12/1996 | Brotz |
| 5,593,424 | A | 1/1997 | Northrup III et al. |
| 5,601,557 | A | 2/1997 | Hayhurst |
| 5,626,590 | A | 5/1997 | Wilk |
| 5,626,611 | A | 5/1997 | Liu et al. |
| 5,632,753 | A | 5/1997 | Loeser |
| 5,643,288 | A | 7/1997 | Thompson |
| 5,643,295 | A | 7/1997 | Yoon |
| 5,643,319 | A | 7/1997 | Green et al. |
| 5,645,568 | A | 7/1997 | Chervitz et al. |
| 5,647,874 | A | 7/1997 | Hayhurst |
| 5,649,939 | A | 7/1997 | Reddick |
| 5,653,716 | A | 8/1997 | Malo et al. |
| 5,662,654 | A | 9/1997 | Thompson |
| 5,662,714 | A | 9/1997 | Charvin et al. |
| 5,669,935 | A | 9/1997 | Rosenman et al. |
| 5,676,675 | A | 10/1997 | Grice |
| D386,583 | S | 11/1997 | Ferragamo et al. |
| 5,683,417 | A | 11/1997 | Cooper |
| D387,161 | S | 12/1997 | Ferragamo et al. |
| 5,695,879 | A | 12/1997 | Goldmann et al. |
| 5,697,976 | A | 12/1997 | Chesterfield et al. |
| 5,702,397 | A | 12/1997 | Goble et al. |
| 5,702,462 | A | 12/1997 | Oberlander |
| 5,709,692 | A | 1/1998 | Mollenauer et al. |
| 5,716,358 | A | 2/1998 | Ochoa et al. |
| 5,716,376 | A | 2/1998 | Roby et al. |
| 5,722,991 | A | 3/1998 | Colligan |
| 5,723,008 | A | 3/1998 | Gordon |
| 5,725,557 | A | 3/1998 | Gatturna et al. |
| 5,728,114 | A | 3/1998 | Evans et al. |
| 5,731,855 | A | 3/1998 | Koyama et al. |
| 5,741,277 | A | 4/1998 | Gordon et al. |
| 5,744,151 | A | 4/1998 | Capelli |
| 5,763,411 | A | 6/1998 | Edwardson et al. |
| 5,765,560 | A | 6/1998 | Verkerke et al. |
| 5,766,246 | A | 6/1998 | Mulhauser et al. |
| 5,779,719 | A | 7/1998 | Klein et al. |
| 5,782,864 | A | 7/1998 | Lizardi |
| 5,807,403 | A | 9/1998 | Beyar et al. |
| 5,807,406 | A | 9/1998 | Brauker et al. |
| 5,810,853 | A | 9/1998 | Yoon |
| 5,814,051 | A | 9/1998 | Wenstrom, Jr. |
| 5,843,087 | A | 12/1998 | Jensen et al. |

(56) References Cited

U.S. PATENT DOCUMENTS

| | | |
|---|---|---|
| 5,843,178 A | 12/1998 | Vanney et al. |
| 5,855,619 A | 1/1999 | Caplan et al. |
| 5,863,360 A | 1/1999 | Wood et al. |
| 5,887,594 A | 3/1999 | LoCicero, III |
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,899,911 A | 5/1999 | Carter |
| 5,916,224 A | 6/1999 | Esplin |
| 5,919,234 A | 7/1999 | Lemperle et al. |
| 5,925,078 A | 7/1999 | Anderson |
| 5,931,855 A * | 8/1999 | Buncke ............ 606/228 |
| 5,938,668 A | 8/1999 | Scirica et al. |
| 5,950,633 A | 9/1999 | Lynch et al. |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 5,997,554 A | 12/1999 | Thompson |
| 6,001,111 A | 12/1999 | Sepetka et al. |
| 6,012,216 A | 1/2000 | Esteves et al. |
| 6,015,410 A | 1/2000 | Tormala et al. |
| 6,024,757 A | 2/2000 | Haase et al. |
| 6,027,523 A | 2/2000 | Schmieding |
| 6,039,741 A | 3/2000 | Meislin |
| 6,042,583 A | 3/2000 | Thompson et al. |
| 6,045,571 A | 4/2000 | Hill et al. |
| 5,320,629 B1 | 5/2000 | Noda et al. |
| 6,056,778 A | 5/2000 | Grafton et al. |
| 6,063,105 A | 5/2000 | Totakura |
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| D433,753 S | 11/2000 | Weiss |
| 6,146,406 A | 11/2000 | Shluzas et al. |
| 6,146,407 A | 11/2000 | Krebs |
| 6,149,660 A | 11/2000 | Laufer et al. |
| 6,159,234 A | 12/2000 | Bonutti et al. |
| 6,160,084 A | 12/2000 | Langer et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,187,095 B1 | 2/2001 | Labrecque et al. |
| 6,203,565 B1 | 3/2001 | Bonutti et al. |
| 6,206,908 B1 | 3/2001 | Roby |
| 6,231,911 B1 | 5/2001 | Steinback et al. |
| 6,235,869 B1 | 5/2001 | Roby et al. |
| 6,241,747 B1 | 6/2001 | Ruff |
| 6,251,143 B1 | 6/2001 | Schwartz et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,788 B1 | 11/2001 | Roby |
| 6,319,231 B1 | 11/2001 | Andrulitis |
| 6,334,865 B1 | 1/2002 | Redmond et al. |
| 6,383,201 B1 | 5/2002 | Dong |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,471,715 B1 | 10/2002 | Weiss |
| 6,478,809 B1 | 11/2002 | Brotz |
| 6,485,503 B2 | 11/2002 | Jacobs et al. |
| 6,491,701 B2 | 12/2002 | Tierney et al. |
| 6,491,714 B1 | 12/2002 | Bennett |
| 6,494,898 B1 | 12/2002 | Roby et al. |
| 6,495,127 B1 | 12/2002 | Wallace et al. |
| RE37,963 E | 1/2003 | Thal |
| 6,506,190 B1 | 1/2003 | Walshe |
| 6,506,197 B1 | 1/2003 | Rollero et al. |
| 6,511,488 B1 | 1/2003 | Marshall et al. |
| 6,514,265 B2 | 2/2003 | Ho et al. |
| 6,527,795 B1 | 3/2003 | Lizardi |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |
| 6,565,597 B1 | 5/2003 | Fearnot et al. |
| 6,592,609 B1 | 7/2003 | Bonutti |
| 6,596,296 B1 | 7/2003 | Nelson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 | 10/2003 | Kim |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,648,921 B2 | 11/2003 | Anderson et al. |
| 6,656,182 B1 | 12/2003 | Hayhurst |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,712,859 B2 | 3/2004 | Rousseau et al. |
| 6,716,234 B2 | 4/2004 | Grafton et al. |
| 6,720,402 B2 | 4/2004 | Langer et al. |
| 6,726,705 B2 | 4/2004 | Peterson et al. |
| 6,746,443 B1 | 6/2004 | Morley et al. |
| 6,746,458 B1 | 6/2004 | Cloud |
| 6,749,616 B1 | 6/2004 | Nath |
| 6,773,450 B2 | 8/2004 | Leung et al. |
| 6,783,554 B2 | 8/2004 | Amara et al. |
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Genova et al. |
| 6,852,825 B2 | 2/2005 | Lendlein et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,921,811 B2 | 7/2005 | Zamora et al. |
| 6,923,819 B2 | 8/2005 | Meade et al. |
| 6,945,021 B2 | 9/2005 | Michel |
| 6,945,980 B2 | 9/2005 | Nguyen et al. |
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. |
| 7,021,316 B2 | 4/2006 | Leiboff |
| 7,033,379 B2 | 4/2006 | Peterson |
| 7,037,984 B2 | 5/2006 | Lediein et al. |
| 7,048,748 B1 | 5/2006 | Ustuner |
| 7,056,331 B2 | 6/2006 | Kaplan et al. |
| 7,056,333 B2 | 6/2006 | Walshe |
| 7,057,135 B2 | 6/2006 | Li |

(56) References Cited

U.S. PATENT DOCUMENTS

| | | |
|---|---|---|
| 7,070,610 B2 | 7/2006 | Im et al. |
| 7,081,135 B2 | 7/2006 | Smith et al. |
| 7,083,637 B1 | 8/2006 | Tannhauser |
| 7,083,648 B2 | 8/2006 | Yu et al. |
| 7,107,090 B2 | 9/2006 | Salisbury, Jr. et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | Del Rio et al. |
| 7,150,757 B2 | 12/2006 | Fallin et al. |
| 7,156,858 B2 | 1/2007 | Schuldt-Hempe et al. |
| 7,156,862 B2 | 1/2007 | Jacobs et al. |
| 7,160,312 B2 | 1/2007 | Saadat |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et al. |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,297,142 B2 | 11/2007 | Brock |
| 7,322,105 B2 | 1/2008 | Lewis |
| 7,329,271 B2 | 2/2008 | Koyfman et al. |
| 7,371,253 B2 | 5/2008 | Leung et al. |
| 7,513,904 B2 | 4/2009 | Sulamanidze et al. |
| 7,582,105 B2 | 9/2009 | Kolster |
| 7,601,164 B2 | 10/2009 | Wu |
| 7,624,487 B2 | 12/2009 | Trull et al. |
| 7,645,293 B2 | 1/2010 | Martinek et al. |
| 7,806,908 B2 | 10/2010 | Ruff |
| 7,845,356 B2 | 12/2010 | Paraschac et al. |
| 7,857,829 B2 | 12/2010 | Kaplan et al. |
| 7,879,072 B2 | 2/2011 | Bonutti et al. |
| 7,919,112 B2 | 4/2011 | Pathak et al. |
| 8,118,834 B1 * | 2/2012 | Goraltchouk et al. ......... 606/228 |
| 8,216,273 B1 | 7/2012 | Goraltchouk et al. |
| 8,226,684 B2 | 7/2012 | Nawrocki et al. |
| 8,308,761 B2 | 11/2012 | Brailovski et al. |
| 8,615,856 B1 | 12/2013 | Gelbart |
| 8,641,732 B1 | 2/2014 | Goraltchouk et al. |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |
| 2001/0039450 A1 | 11/2001 | Pavcnik et al. |
| 2001/0051807 A1 | 12/2001 | Grafton |
| 2002/0007218 A1 | 1/2002 | Cauthen |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0077448 A1 | 6/2002 | Antal et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0138009 A1 | 9/2002 | Brockway et al. |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0165555 A1 | 11/2002 | Stein et al. |
| 2002/0173822 A1 | 11/2002 | Justin et al. |
| 2002/0179718 A1 | 12/2002 | Murokh et al. |
| 2002/0198544 A1 | 12/2002 | Uflacker |
| 2003/0040795 A1 | 2/2003 | Elson et al. |
| 2003/0069602 A1 | 4/2003 | Jacobs et al. |
| 2003/0088270 A1 | 5/2003 | Lubbers et al. |
| 2003/0149447 A1 | 8/2003 | Morency |
| 2003/0158604 A1 | 8/2003 | Cauthen, III et al. |
| 2003/0167072 A1 | 9/2003 | Oberlander |
| 2003/0199923 A1 | 10/2003 | Khairkhahan et al. |
| 2003/0203003 A1 | 10/2003 | Nelson et al. |
| 2003/0204193 A1 | 10/2003 | Gabriel et al. |
| 2003/0204195 A1 | 10/2003 | Keane et al. |
| 2003/0225424 A1 | 12/2003 | Benderev |
| 2003/0229361 A1 | 12/2003 | Jackson |
| 2003/0236551 A1 | 12/2003 | Peterson |
| 2004/0006353 A1 | 1/2004 | Bosley, Jr. et al. |
| 2004/0010275 A1 | 1/2004 | Jacobs et al. |
| 2004/0010276 A1 | 1/2004 | Jacobs et al. |
| 2004/0015187 A1 | 1/2004 | Lendlein et al. |
| 2004/0024169 A1 | 2/2004 | Shalaby et al. |
| 2004/0024420 A1 | 2/2004 | Lubbers et al. |
| 2004/0030354 A1 | 2/2004 | Leung et al. |
| 2004/0039415 A1 | 2/2004 | Zamierowski |
| 2004/0049224 A1 | 3/2004 | Buehlmann et al. |
| 2004/0059370 A1 | 3/2004 | Greene, Jr. et al. |
| 2004/0059377 A1 | 3/2004 | Peterson et al. |
| 2004/0060409 A1 | 4/2004 | Leung et al. |
| 2004/0060410 A1 | 4/2004 | Leung et al. |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0093023 A1 | 5/2004 | Allen et al. |
| 2004/0098051 A1 | 5/2004 | Fallin et al. |
| 2004/0106949 A1 | 6/2004 | Cohn et al. |
| 2004/0116620 A1 | 6/2004 | Shalaby et al. |
| 2004/0138683 A1 | 7/2004 | Shelton et al. |
| 2004/0153153 A1 | 8/2004 | Elson et al. |
| 2004/0167572 A1 | 8/2004 | Roth et al. |
| 2004/0167575 A1 | 8/2004 | Roby |
| 2004/0186487 A1 | 9/2004 | Klein et al. |
| 2004/0193191 A1 | 9/2004 | Starksen et al. |
| 2004/0193217 A1 | 9/2004 | Lubbers et al. |
| 2004/0193257 A1 | 9/2004 | Wu et al. |
| 2004/0230223 A1 | 11/2004 | Bonutti et al. |
| 2004/0260340 A1 | 12/2004 | Jacobs et al. |
| 2004/0265282 A1 | 12/2004 | Wright et al. |
| 2004/0267309 A1 | 12/2004 | Garvin |
| 2005/0004601 A1 | 1/2005 | Kong et al. |
| 2005/0004602 A1 | 1/2005 | Hart et al. |
| 2005/0033324 A1 | 2/2005 | Phan |
| 2005/0034431 A1 | 2/2005 | Dey et al. |
| 2005/0038472 A1 | 2/2005 | Furst |
| 2005/0049636 A1 | 3/2005 | Leiboff |
| 2005/0055051 A1 | 3/2005 | Grafton |
| 2005/0059984 A1 | 3/2005 | Chanduszko et al. |
| 2005/0065533 A1 | 3/2005 | Magen et al. |
| 2005/0070959 A1 | 3/2005 | Cichocki, Jr. |
| 2005/0080455 A1 | 4/2005 | Schmieding et al. |
| 2005/0085857 A1 | 4/2005 | Peterson et al. |
| 2005/0096698 A1 | 5/2005 | Lederman |
| 2005/0113936 A1 | 5/2005 | Brustad et al. |
| 2005/0119694 A1 | 6/2005 | Jacobs et al. |
| 2005/0125020 A1 | 6/2005 | Meade et al. |
| 2005/0125034 A1 | 6/2005 | Cichocki, Jr. |
| 2005/0125035 A1 | 6/2005 | Cichocki, Jr. |
| 2005/0149064 A1 | 7/2005 | Peterson et al. |
| 2005/0149118 A1 | 7/2005 | Koyfman et al. |
| 2005/0154255 A1 | 7/2005 | Jacobs |
| 2005/0171561 A1 | 8/2005 | Songer et al. |
| 2005/0177190 A1 | 8/2005 | Zamierowski |
| 2005/0181009 A1 | 8/2005 | Hunter et al. |
| 2005/0182444 A1 | 8/2005 | Peterson et al. |
| 2005/0182445 A1 | 8/2005 | Zamierowski |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1 | 9/2005 | Sulamanidze et al. |
| 2005/0209542 A1 | 9/2005 | Jacobs et al. |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0267531 A1 | 12/2005 | Ruff et al. |
| 2005/0267532 A1 | 12/2005 | Wu |
| 2005/0277984 A1 | 12/2005 | Long |

(56) References Cited

U.S. PATENT DOCUMENTS

| | | |
|---|---|---|
| 2005/0283246 A1 | 12/2005 | Cauthen, III et al. |
| 2006/0020272 A1 | 1/2006 | Gildenberg |
| 2006/0030884 A1 | 2/2006 | Young et al. |
| 2006/0036266 A1 | 2/2006 | Sulamanidze et al. |
| 2006/0058470 A1 | 3/2006 | Rizk |
| 2006/0058574 A1 | 3/2006 | Priewe et al. |
| 2006/0058799 A1 | 3/2006 | Elson et al. |
| 2006/0058844 A1 | 3/2006 | White et al. |
| 2006/0063476 A1 | 3/2006 | Dore |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079935 A1 | 4/2006 | Kolster |
| 2006/0085016 A1 | 4/2006 | Eremia |
| 2006/0089525 A1 | 4/2006 | Mamo et al. |
| 2006/0089672 A1 | 4/2006 | Martinek |
| 2006/0111734 A1 | 5/2006 | Kaplan et al. |
| 2006/0111742 A1 | 5/2006 | Kaplan et al. |
| 2006/0116503 A1 | 6/2006 | Lendlein et al. |
| 2006/0122608 A1 | 6/2006 | Fallin et al. |
| 2006/0135994 A1 | 6/2006 | Ruff |
| 2006/0135995 A1 | 6/2006 | Ruff |
| 2006/0140999 A1 | 6/2006 | Lendlein et al. |
| 2006/0142784 A1 | 6/2006 | Kontos |
| 2006/0193769 A1 | 8/2006 | Nelson et al. |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235445 A1 | 10/2006 | Birk et al. |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin et al. |
| 2006/0253126 A1 | 11/2006 | Bjerken et al. |
| 2006/0257629 A1 | 11/2006 | Lendlein et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0282099 A1 | 12/2006 | Stokes et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2006/0293710 A1 | 12/2006 | Foerster et al. |
| 2007/0005109 A1 | 1/2007 | Popadiuk et al. |
| 2007/0005110 A1* | 1/2007 | Collier et al. ................ 606/228 |
| 2007/0016251 A1 | 1/2007 | Roby |
| 2007/0021779 A1 | 1/2007 | Garvin et al. |
| 2007/0027475 A1 | 2/2007 | Pagedas |
| 2007/0038249 A1 | 2/2007 | Kolster |
| 2007/0065663 A1* | 3/2007 | Trull et al. .................... 428/357 |
| 2007/0088135 A1 | 4/2007 | Lendlein et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0135843 A1 | 6/2007 | Burkhart |
| 2007/0151961 A1 | 7/2007 | Kleine et al. |
| 2007/0156175 A1 | 7/2007 | Weadock et al. |
| 2007/0167958 A1 | 7/2007 | Sulamanidze et al. |
| 2007/0187861 A1 | 8/2007 | Geneva et al. |
| 2007/0208355 A1 | 9/2007 | Ruff |
| 2007/0208377 A1 | 9/2007 | Kaplan et al. |
| 2007/0213770 A1 | 9/2007 | Dreyfuss |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0225763 A1 | 9/2007 | Zwolinski et al. |
| 2007/0233188 A1 | 10/2007 | Hunt et al. |
| 2007/0239206 A1 | 10/2007 | Shelton, IV et al. |
| 2007/0239207 A1 | 10/2007 | Beramendi |
| 2007/0257395 A1 | 11/2007 | Lindh et al. |
| 2007/0282247 A1 | 12/2007 | Desai et al. |
| 2007/0293892 A1* | 12/2007 | Takasu ......................... 606/228 |
| 2008/0004490 A1 | 1/2008 | Bosley, Jr. et al. |
| 2008/0004603 A1 | 1/2008 | Larkin et al. |
| 2008/0009838 A1 | 1/2008 | Schena et al. |
| 2008/0009888 A1 | 1/2008 | Ewers et al. |
| 2008/0009902 A1 | 1/2008 | Hunter et al. |
| 2008/0027273 A1 | 1/2008 | Gutterman |
| 2008/0027486 A1 | 1/2008 | Jones et al. |
| 2008/0046094 A1 | 2/2008 | Han et al. |
| 2008/0058869 A1 | 3/2008 | Stopek et al. |
| 2008/0064839 A1 | 3/2008 | Hadba et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0077181 A1 | 3/2008 | Jones et al. |
| 2008/0082113 A1 | 4/2008 | Bishop et al. |
| 2008/0082129 A1 | 4/2008 | Jones et al. |
| 2008/0086169 A1 | 4/2008 | Jones et al. |
| 2008/0086170 A1 | 4/2008 | Jones et al. |
| 2008/0109036 A1 | 5/2008 | Stopek et al. |
| 2008/0131692 A1 | 6/2008 | Rolland et al. |
| 2008/0132943 A1 | 6/2008 | Maiorino et al. |
| 2008/0169059 A1 | 7/2008 | Messersmith et al. |
| 2008/0195147 A1 | 8/2008 | Stopek |
| 2008/0208358 A1 | 8/2008 | Bellamkonda et al. |
| 2008/0215072 A1 | 9/2008 | Kelly |
| 2008/0221618 A1 | 9/2008 | Chen et al. |
| 2008/0234731 A1 | 9/2008 | Leung et al. |
| 2008/0248216 A1 | 10/2008 | Yeung et al. |
| 2008/0255611 A1 | 10/2008 | Hunter |
| 2008/0255612 A1 | 10/2008 | Hunter |
| 2008/0262542 A1 | 10/2008 | Sulamanidze et al. |
| 2008/0281338 A1 | 11/2008 | Wohlert et al. |
| 2008/0281357 A1 | 11/2008 | Sung et al. |
| 2008/0312688 A1 | 12/2008 | Naworocki et al. |
| 2009/0012560 A1 | 1/2009 | Hunter et al. |
| 2009/0018577 A1 | 1/2009 | Leung et al. |
| 2009/0043336 A1 | 2/2009 | Yuan et al. |
| 2009/0076543 A1 | 3/2009 | Maiorino et al. |
| 2009/0082856 A1 | 3/2009 | Flanagan |
| 2009/0088835 A1 | 4/2009 | Wang |
| 2009/0099597 A1 | 4/2009 | Isse |
| 2009/0105753 A1 | 4/2009 | Greenhalgh et al. |
| 2009/0107965 A1 | 4/2009 | D'Agostino |
| 2009/0112236 A1 | 4/2009 | Stopek |
| 2009/0112259 A1 | 4/2009 | D'Agostino |
| 2009/0143819 A1 | 6/2009 | D'Agostino |
| 2009/0200487 A1 | 8/2009 | Maiorino et al. |
| 2009/0210006 A1 | 8/2009 | Cohen et al. |
| 2009/0216253 A1 | 8/2009 | Bell et al. |
| 2009/0226500 A1 | 9/2009 | Avelar et al. |
| 2009/0228021 A1 | 9/2009 | Leung |
| 2009/0248066 A1 | 10/2009 | Wilkie |
| 2009/0248067 A1 | 10/2009 | Maiorino |
| 2009/0248070 A1 | 10/2009 | Kosa et al. |
| 2009/0250588 A1 | 10/2009 | Robeson et al. |
| 2009/0259233 A1 | 10/2009 | Bogart et al. |
| 2009/0259251 A1 | 10/2009 | Cohen |
| 2009/0287245 A1 | 11/2009 | Ostrovsky et al. |
| 2009/0299407 A1 | 12/2009 | Yuan et al. |
| 2009/0299408 A1 | 12/2009 | Schuldt-Hempe et al. |
| 2009/0306710 A1 | 12/2009 | Lindh et al. |
| 2009/0318958 A1 | 12/2009 | Ochiai |
| 2010/0021516 A1 | 1/2010 | McKay |
| 2010/0023055 A1 | 1/2010 | Rousseau |
| 2010/0057123 A1 | 3/2010 | D'Agostino et al. |
| 2010/0063540 A1 | 3/2010 | Maiorino |
| 2010/0071833 A1 | 3/2010 | Maiorino |
| 2010/0087855 A1 | 4/2010 | Leung et al. |
| 2010/0101707 A1 | 4/2010 | Maiorino et al. |
| 2010/0160961 A1 | 6/2010 | Nawrocki et al. |
| 2010/0163056 A1 | 7/2010 | Tschopp et al. |
| 2010/0198257 A1 | 8/2010 | Stopek et al. |
| 2010/0211097 A1 | 8/2010 | Hadba et al. |
| 2010/0211098 A1 | 8/2010 | Hadba et al. |
| 2010/0230300 A1 | 9/2010 | Hunter et al. |
| 2010/0239635 A1 | 9/2010 | McClain et al. |
| 2010/0292718 A1 | 11/2010 | Sholev et al. |
| 2010/0294103 A1 | 11/2010 | Genova et al. |
| 2010/0294104 A1 | 11/2010 | Genova et al. |

(56) References Cited

U.S. PATENT DOCUMENTS

| | | | |
|---|---|---|---|
| 2010/0294105 | A1 | 11/2010 | Genova et al. |
| 2010/0294106 | A1 | 11/2010 | Genova et al. |
| 2010/0294107 | A1 | 11/2010 | Genova et al. |
| 2010/0298637 | A1 | 11/2010 | Ruff |
| 2010/0298639 | A1 | 11/2010 | Leung et al. |
| 2010/0298848 | A1 | 11/2010 | Leung et al. |
| 2010/0298867 | A1 | 11/2010 | Ruff |
| 2010/0298868 | A1 | 11/2010 | Ruff |
| 2010/0298871 | A1 | 11/2010 | Ruff et al. |
| 2010/0298878 | A1 | 11/2010 | Leung et al. |
| 2010/0298879 | A1 | 11/2010 | Leung et al. |
| 2010/0298880 | A1 | 11/2010 | Leung et al. |
| 2010/0313723 | A1 | 12/2010 | Genova et al. |
| 2010/0313729 | A1 | 12/2010 | Genova et al. |
| 2010/0313730 | A1 | 12/2010 | Genova et al. |
| 2010/0318122 | A1 | 12/2010 | Leung et al. |
| 2010/0318123 | A1 | 12/2010 | Leung et al. |
| 2010/0318124 | A1 | 12/2010 | Leung et al. |
| 2011/0009902 | A1 | 1/2011 | Leung et al. |
| 2011/0022086 | A1 | 1/2011 | D'Agostino et al. |
| 2011/0046668 | A1 | 2/2011 | Goraltchouk et al. |
| 2011/0046669 | A1 | 2/2011 | Goraltchouk et al. |
| 2011/0106152 | A1 | 5/2011 | Kozlowski |
| 2011/0125188 | A1 | 5/2011 | Goraltchouk et al. |
| 2011/0130774 | A1 | 6/2011 | Criscuolo et al. |
| 2011/0166597 | A1 | 7/2011 | Herrmann et al. |
| 2011/0288583 | A1 | 11/2011 | Goraltchouk et al. |
| 2012/0101522 | A1 | 4/2012 | Megaro et al. |
| 2012/0109188 | A1 | 5/2012 | Viola |

FOREIGN PATENT DOCUMENTS

| | | |
|---|---|---|
| CN | 2640420 | 9/2004 |
| DE | 01810800 | 6/1970 |
| DE | 03227984 | 2/1984 |
| DE | 04302895 | 8/1994 |
| DE | 19618891 | 4/1997 |
| DE | 19833703 | 2/2000 |
| DE | 10245025 | 4/2004 |
| DE | 102005004317 | 6/2006 |
| EP | 0121362 | 9/1987 |
| EP | 0329787 | 8/1989 |
| EP | 0513713 | 5/1992 |
| EP | 0428253 | 7/1994 |
| EP | 0632999 | 1/1995 |
| EP | 0513736 | 2/1995 |
| EP | 0464479 | 3/1995 |
| EP | 0464480 | 3/1995 |
| EP | 0576337 | 3/1997 |
| EP | 0574707 | 8/1997 |
| EP | 0612504 | 11/1997 |
| EP | 0558993 | 4/1998 |
| EP | 0913123 | 5/1999 |
| EP | 0916310 | 5/1999 |
| EP | 0664198 | 6/1999 |
| EP | 0960600 | 12/1999 |
| EP | 0705567 | 3/2002 |
| EP | 0673624 | 8/2002 |
| EP | 0839499 | 9/2003 |
| EP | 0755656 | 12/2003 |
| EP | 1075843 | 2/2005 |
| EP | 1525851 | 4/2005 |
| EP | 1532942 | 5/2005 |
| EP | 0826337 | 12/2005 |
| EP | 0991359 | 11/2007 |
| EP | 2036502 | 3/2009 |
| EP | 1948261 | 11/2010 |
| EP | 2245992 | 11/2010 |
| EP | 1726317 | 7/2012 |
| EP | 2338421 | 11/2012 |
| FR | 2619129 | 2/1989 |
| FR | 2693108 | 1/1994 |
| GB | 0267007 | 3/1927 |
| GB | 1091282 | 11/1967 |
| GB | 1428560 | 7/1973 |
| GB | 1506362 | 4/1978 |
| GB | 1508627 | 4/1978 |
| JP | 1506362 | 4/1978 |
| JP | 54-116419 | 9/1979 |
| JP | 63-288146 | 11/1988 |
| JP | 001113091 | 5/1989 |
| JP | 3-165751 | 7/1991 |
| JP | 4-096758 | 3/1992 |
| JP | 4-266749 | 9/1992 |
| JP | 9-103477 | 4/1997 |
| JP | 410085225 | 4/1998 |
| JP | 11-313826 | 11/1999 |
| JP | 011332828 | 12/1999 |
| JP | 2002-059235 | 2/2002 |
| JP | 2003-275217 | 9/2003 |
| JP | 2009-118967 | 6/2009 |
| KR | 10-2005-0072908 A | 7/2005 |
| KR | 6013299 | 2/2006 |
| NZ | 501224 | 3/2002 |
| NZ | 531262 | 12/2005 |
| RU | 2139690 | 10/1999 |
| RU | 2175855 | 11/2001 |
| RU | 2241389 | 12/2004 |
| RU | 2268752 | 1/2006 |
| SU | 1745214 | 7/1992 |
| SU | 1752358 | 8/1992 |
| WO | WO 86/00020 | 1/1986 |
| WO | WO 87/01270 | 3/1987 |
| WO | WO 88/09157 | 12/1988 |
| WO | WO 89/05618 | 6/1989 |
| WO | WO 90/09149 | 8/1990 |
| WO | WO 90/14795 | 12/1990 |
| WO | WO 92/22336 | 12/1992 |
| WO | WO 95/16399 | 6/1995 |
| WO | WO 95/29637 | 11/1995 |
| WO | WO 96/06565 | 3/1996 |
| WO | WO 98/52473 | 11/1998 |
| WO | WO 98/55031 | 12/1998 |
| WO | WO 99/21488 | 5/1999 |
| WO | WO 99/33401 | 7/1999 |
| WO | WO 99/52478 | 10/1999 |
| WO | WO 99/59477 | 11/1999 |
| WO | WO 99/62431 | 12/1999 |
| WO | WO 00/51658 | 9/2000 |
| WO | WO 00/51685 | 9/2000 |
| WO | WO 01/06952 | 2/2001 |
| WO | WO 01/56626 | 8/2001 |
| WO | WO 03/001979 | 1/2003 |
| WO | WO 03/003925 | 1/2003 |
| WO | WO 03/045255 | 6/2003 |
| WO | WO 03/077772 | 9/2003 |
| WO | WO 03/092758 | 11/2003 |
| WO | WO 03/103733 | 12/2003 |
| WO | WO 03/103972 | 12/2003 |
| WO | WO 03/105703 | 12/2003 |
| WO | WO 2004/014236 | 2/2004 |
| WO | WO 2004/030517 | 4/2004 |
| WO | WO 2004/030520 | 4/2004 |
| WO | WO 2004/030704 | 4/2004 |
| WO | WO 2004/030705 | 4/2004 |
| WO | WO 2004/062459 | 7/2004 |
| WO | WO 2004/100801 | 11/2004 |
| WO | WO 2004/112853 | 12/2004 |
| WO | WO 2005/016176 | 2/2005 |
| WO | WO 2005/074913 | 8/2005 |
| WO | WO 2005/096955 | 10/2005 |
| WO | WO 2005/096956 | 10/2005 |
| WO | WO 2005/112787 | 12/2005 |
| WO | WO 2006/005144 | 1/2006 |
| WO | WO 2006/012128 | 2/2006 |
| WO | WO 2006/037399 | 4/2006 |
| WO | WO 2006/061868 | 6/2006 |
| WO | WO 2006/079469 | 8/2006 |
| WO | WO 2006/082060 | 8/2006 |
| WO | WO 2006/099703 | 9/2006 |
| WO | WO 2006/138300 | 12/2006 |
| WO | WO 2007/005291 | 1/2007 |
| WO | WO 2007/005296 | 1/2007 |

(56) References Cited

FOREIGN PATENT DOCUMENTS

| | | |
|---|---|---|
| WO | WO 2007/038837 | 4/2007 |
| WO | WO 2007/053812 | 5/2007 |
| WO | WO 2007/089864 | 8/2007 |
| WO | WO 2007/112024 | 10/2007 |
| WO | WO 2007/133103 | 11/2007 |
| WO | WO 2007/145614 | 12/2007 |
| WO | WO 2008/128113 | 10/2008 |
| WO | WO 2009/042841 | 4/2009 |
| WO | WO 2009/068252 | 6/2009 |
| WO | WO 2009/087105 | 7/2009 |
| WO | WO 2009/097556 | 8/2009 |
| WO | WO 2009/151876 | 12/2009 |
| WO | WO 2010/052007 | 5/2010 |
| WO | WO 2011/053375 | 5/2011 |
| WO | WO 2011/139916 | 11/2011 |
| WO | WO 2011/140283 | 11/2011 |

OTHER PUBLICATIONS

Behl, Marc et al., "Shape-Memory Polymers", Materials Today Apr. 2007; 10(4); 20-28.
Belkas, J. S. et al., "Peripheral nerve regeneration through a synthetic hydrogel nerve tube", Restorative Neurology and Neuroscience 23 (2005) 19-29.
Bellin, I. et al., "Polymeric triple-shape materials", Proceedings of the National Academy of Sciences of the United States of America Nov. 28, 2006; 2103(48):18043-18047.
Boenisch, U.W. et al 'Pull-Out strength and stiffness of meniscal repair using absorbable arrows or Ti-Cron vertical and horizontal loop sutures' American Journal of Sports Medicine, Sep.-Oct. (1999) vol. 27, Issue 5, pp. 626-631.
Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.
Buncke, Jr., H.J. et al 'The Suture Repair of One-Millimeter Vessels, microvascular surgery' (1966) Report of First Conference; Oct. 6-7 pp. 24-35.
Bunnell, S. 'Gig pull-out suture for tendons' J Bone Joint Surg. Am (1954) vol. 36A, No. 4 pp. 850-851.
CCPR Centro De Cirurgia Plastica e Reabilitacao Up Lifting (Aptos Threads) http://ccpr.com.br/upl-l.htm, Aug. 19, 2002 pp. 1-2.
Dahlin, Lars, "Techniques of Peripheral Nerve Repair", Scandinavian Journal of Surgery 97: 310-316, 2008.
Datillo, Jr., P.P. 'Knotless Bi-directional Barbed Absorbable Surgical Suture' Dissertation submitted to the Graduate Faculty of North Carolina State University Textile Management and Technology Nov. 2002, 75 pages.
Datillo, Jr. P.P. et al 'Medical Textiles: Application of an Absorbable Barbed Bi-Directional Surgical Suture' (2002) The Journal of Textile and Apparel Technology and Management vol. 2, Issue 2, pp. 1-5.
Datillo, Jr., P. et al 'Tissue holding performance of knotless absorbable sutures' Society for Biomaterials 29th Annual Meeting Transactions (2003) p. 101.
Declaration of Dr. Gregory L. Ruff, dated Aug. 19, 2005, 8 pages, with Exhibits A-E.
De Persia, Raúl et al., "Mechanics of Biomaterials: Sutures After the Surgery", Applications of Engineering Mechanics in Medicine, GED-University of Puerto Rico, Mayaguez May 2005, p. F1-F27.
Delorenzi, C.L., "Barbed Sutures: Rationale and Technique", Aesthetic Surg. J. Mar 26, 2006(2): 223-229.
Demyttenaere, Sebastian V. et al., "Barbed Suture for Gastrointestinal Closure: A Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Gross, Alex, "Physician perspective on thread lifts", Dermatology Times Feb 27, 2006(2): 2 pages.

Gross, R.A. et al 'Biodegradable Polymers for the Environment' Science (2002) vol. 297, Issue 5582 pp. 803.
Han, H. et al 'Mating and Piercing Micromechanical Suture for Surface Bonding Applications' (1991) Proceedings of the 1991 Micro Electro Mechanical Systems (MEMS>91), An Investigation of Micro Structures, Sensors, Actuators, Machines and Robots pp. 253-258.
Ingle, N. P. et al 'Barbed Suture Anchoring Strength: Applicability to Dissimilar Polymeric Materials' College of Textiles, North Carolina State University, 7th World Biomaterials Congress 2004, 1 page.
Ingle, N. P. et al 'Mechanical Performance and Finite Element Analysis of Bi-directional Barbed Sutures' Master of Science in Textile Technology & Management at North Carolina State University Aug. 2003, 126 pages.
Ingle, N. P. et al., "Optimizing the tissue anchoring performance of barbed sutures in skin and tendon tissues", Journal of Biomechanics 43 (2010); pp. 302-309.
Ingle, Nilesh P et al., "Testing the Tissue-holding Capacity of Barbed Sutures", College of Textiles, North Carolina State University, Fiber Science, the Next Generation Oct. 17-19, 2005, New Jersey Institute of Technology, Newark, NJ, 4 pages.
Jennings et al 'A New Technique in primary tendon repair' Surg. Gynecol. Obstet. (1952) vol. 95, No. 5 pp. 597-600.
Jeong, H.E. et al 'A nontransferring dry adhesive with hierarchial polymer nanohairs' PNAS 106 (14) pp. 5639-5644 (2009).
Kaminer, M. et al., "ContourLift™: A New Method of Minimally Invasive Facial Rejuvenation", Cosmetic Dermatology Jan. 2007; 20(1): 29-35.
Kelch et al., "Shape-memory Polymer Networks from Olio [($\epsilon$-hydroxycaproate)-co-glycolate]dimethacrylates and Butyl Acrylate with Adjustable Hydrolytic Degradation Rate", Biomacromolecules 2007;8(3):1018-1027.
Khademhosseini, Ali et al., "Nanobiotechnology Drug Delivery and Tissue Engineering", Chemical Engineering Progress 102:38-42 (2006).
Kuniholm J.F. et al 'Automated Knot Tying for Fixation in Minimally Invasive, Robot Assisted Cardiac Surgery' Master of Science in Mechanical & Aerospace Engineering at North Carolina State University May 2003, 71 pages.
Lendlein, A. et al 'Biodegradable, Elastic Shape-Memory Polymers for Potential Biomedical Applications' (2002) Science vol. 296 pp. 1673-1676.
Lendlein, A. et al 'Shape-Memory Polymers' Agnew Chem. Int. Ed. (2002) vol. 41 pp. 2034-2057.
Leung, J. et al 'Barbed, Bi-directional Medical Sutures: Biomechanical Properties and Wound Closure Efficacy Study' 2002 Society for Biomaterials 28th Annual Meeting Transactions 1 page.
Leung, J. et al 'Barbed, Bi-directional Surgical Sutures' International Conference & Exhibition on Healthcare & Medical Textiles, Jul. 8-9, 2003 pp. 1-8.
Leung, J. et al 'Barbed, Bi-directional Surgical Sutures: in Vivo Strength and Histopathology Evaluations' 2003 Society for Biomaterials 29th Annual Meeting Transactions pp. 100.
Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.
Leung, J. et al 'Performance Enhancement of a Knotless Suture via Barb Geometry Modifications' 7th World Biomaterials Congress 2004, 1 page.
Li, Y.Y. et al 'Polymer Replicas of Photonic Porous Silicon for Sensing and Drug Delivery Applications' (2003) Science vol. 299 pp. 2045-2047.
Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.
Madduri, Srinivas, et al., "Neurotrophic factors release from nerve conduits for peripheral axonal regeneration", European Cells and Materials vol. 16; Suppl. 1 (2008), p. 14.
Madhave et al 'A biodegradable and biocompatible gecko-inspired tissue adhesive' PNAS 105(7) pp. 2307-2312 (2008).

(56) References Cited

OTHER PUBLICATIONS

Maitland et al., "Prototype laser-activated shape memory polymer foam device for embolic treatment of aneurysms", Journal of Biomedical Optics May/Jun. 2007;12(3): pp. 030504-1 to 030504-3.
Malina, M. et al 'Endovascular AAA Exclusion: Will Stents with Hooks and Barbs Prevent Stent-Graft Migration' Journal Endovascular Surgery (1998) vol. 5 pp. 310-317.
Mansberger et al 'A New Type Pull-Out Wire for Tendon Surgery: A Preliminary Report' Department of Surgery, University Hospital and University of Maryland School of Medicine, Baltimore, Maryland, Received for Publication May 10, 1951 pp. 119-121.
Martin, D.P. et al 'Medical applications of poly-4-hydroxybutyrate: a strong flexible absorbable biomaterial' Biochemical Engineering Journal vol. 16 (2003) pp. 97-105.
Mason, M.L. 'Primary and Secondary Tendon Suture. A discussion of the significance of technique in tendon surgery' (1940) Surg Gynecol Obstet 70.
McKee, GK 'Metal anastomosis tubes in tendon suture' The Lancet (1945) pp. 659-660.
McKenzie 'An Experimental Multiple Barbed Suture for the Long Flexor Tendons of the Palm and Fingers' The Journal of Bone and Joint Surgery (1967) vol. 49B, No. 3 pp. 440-447.
Middleton and Tipton 'Synthetic Biodegradable Polymers as Medical Devices' (1998) Medical Plastics and Biomaterials Magazine, 9 pages.
Moran et al., "Bidirectional-Barbed Sutured Knotless Running Anastomosis v Classic van Velthovan in a Model System", Journal of Endourology Oct. 2007; 21(10); 1175-1177.
Mullner, "Metal Foam Has a Good Memory", Dec. 18, 2007 Original story at <http://www.physorg.com/news117214996.html>.
Murtha et al., "Evaluation of a Novel Technique for Wound Closure Using a Barbed Suture", Journal of the American Society of Plastic Surgeons 2006; 117(6); 1769-1780.
Nie, Zhihong and Kumacheva, Eugenia, "Patterning surfaces with functional polymers", Nature Materials vol. 7(2008): 277-290.
Paul, Malcolm D., "Bidirectional Barbed Sutures for Wound Closure: Evolution and Applications", Journal of the American College of Certified Wound Specialists (2009) 1, 51-57.
Paul, Malcolm D. and Rui Avelar, "Quill™ SRS Techniques & Procedures a Novel Approach to Soft Tissue Approximation", Canada, Angiotech Pharmaceuticals, Inc., First Edition Aug. 2007: 20 pages.
Paul, Malcolm D. and Rui Avelar, "Quill™ SRS Techniques & Procedures a Novel Approach to Soft Tissue Approximation", Canada, Angiotech Pharmaceuticals, Inc., Second Edition Aug. 2008: 20 pages.
Paul, Malcolm D. and Rui Avelar, "Quill™ SRS Techniques & Procedures a Novel Approach to Soft Tissue Approximation", Canada, Angiotech Pharmaceuticals, Inc., Third Edition 2009, 8 2007-2009: 27 pages.
Paul, Malcolm D. and Rui Avelar, "Quill™ SRS Techniques & Procedures a Novel Approach to Soft Tissue Approximation", Canada, Angiotech Pharmaceuticals, Inc., Fourth Edition 2010, 8 2007-2010: 27 pages.
Paul, Malcolm D., "Using Barbed Sutures in Open/Subperiosteal Midface Lifting", Aesthetic Surgery Journal 2006(26): 725-732.
Potenza, A. 'Tendon Healing Within the Flexor Digital Sheath in the Dog: An Experimental Study' Journal of Bone & Joint Surgery (1962) vol. 44A No. 1 pp. 49-64.
Pulvertaft 'Suture Materials and Tendon Junctures' American Journal of Surgery (1965) vol. 109 pp. 346-352.
Quill Medical, Inc. 'Barbed Sutures, wrinkle filters give patients more innovative, non-surgical options' Press Release of Program presented at American Society of Plastic Surgeons annual scientific meeting; Philadelphia, Oct. 9, 2004 3 pages.
Quill Medical, Inc. 'Quill Medical's Novel-Self-Anchoring Surgical Suture Approved for Sale in Europe' Press Release; Research Triangle Park, N.C. May 10, 2004, 1 page.
Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.
Richert, Ludovic, et al., "Surface Nanopatterning to Control Cell Growth", Advanced Materials 2008(15): 1-5.
Rodeheaver, G.T. et al., "Barbed Sutures for Wound Closure: in Vivo Wound Security, Tissue Compatibility and Cosmesis Measurements", Society for Biomaterials 30th Annual Meeting Transactions, 2005, 2 pages.
Rofin-Baasel 'Laser Marking on Plastic Materials' (2001) RB50.0, Rofin-Baasel Inc. 2 pages.
Ruff, Gregory, "Technique and Uses for Absorbable Barbed Sutures", Aesthetic Surgery Journal Sep./Oct. 2006; 26:620-628.
Scherman, Peter et al., "Sutures as longitudinal guides for the repair of nerve defects—Influence of suture numbers and reconstruction of nerve bifurcations", Restorative Neurology and Neuroscience 23 (2005) 79-85.
Schmid A. et al 'The outspreading anchor cord. A material for arthroscopic suturing of a fresh anterior cruciate ligament rupture' Surgical Clinic of the University of Gottingen (1987) pp. 417-426.
Semenov, G.M. et al 'Surgical Suture' (2001) Piter, Saint Petersburg, pp. 12-13 and 92-98.
Serafetinides, AA 'Short pulse laser beam interactions with polymers biocompatible materials and tissue' Proce SPIE vol. 3052 (1996) pp. 111-123.
Sulamanidze, M. et al., "APTOS Suture Lifting Methods: 10 Years of Experience", Clin Plastic Surg 36 (2009); pp. 281-306.
Sulamanidze, M.A. et al 'Clinical aspects of bloodless facelift using APTOS filaments' A.V. Vishnevsky Institute of Surgery, Bol'shaya Serpukhovskaya ul, 7, 113811, Moscow, Russia (2002) pp. 24-34.
Sulamanidze, M.A. et al 'Facial lifting with Aptos threads' International Journal of Cosmetic Surgery and Aesthetic Dermatology (2001) No. 4 pp. 1-8.
Sulamanidze, M.A. et al 'Management of Facial Rhytids by Subcutaneous Soft Tissue Dissection' (2000) International Journal of Cosmetic Surgery and Aesthetic Dermatology vol. 2 No. 4 pp. 255-259.
Sulamanidze, M.A. et al 'Morphological foundations of facelift using APTOS filaments' Bolshaya Serpukhovskaya ul 27, 113811 Moscow, Russia (2002) pp. 19-26.
Sulamanidze, M.A. et al 'Removal of Facial Soft Tissue Ptosis with Special Threads' Dermatol Surg (2002) vol. 28 pp. 367-371.
Sulamanidze, MD, M.A., et al., "Soft tissue lifting in the mid-face: old philosophy, new approach—internal stitching technique (APTOS Needle)", Plastic and Aesthetic Surgery Clinic TOTAL SHARM, Moscow, Russia, (2005):15-29.
Sulzle, Inc. B.G. et al Drilled End Surgical Needles Jul. 2002 Syracuse, New York.
Surgical Specialties Corporation, "Wound Closure Catalog"; Summer 2005, 5 pages.
Szarmach, R. et al 'An Expanded Surgical Suture and Needle Evaluation and Selection Program by a Healthcare Resource Management Group Purchasing Organization' Journal of Long-Term Effects of Medical Implants (2003) vol. 13 No. 3 pp. 155-170.
Verdan, C. 'Primary Repair of Flexor Tendons' Journal of Bone and Joint Surgery (1960) vol. 42, No. 4 pp. 647-657.
Villa, Mark T. et al., "Barbed Sutures: A Review of Literature", Plastic and Reconstructive Surgery; Mar. 2008; vol. 121, No. 3; pp. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.
International Search Report for PCT/US2009/034703 dated Sep. 28, 2009.
International Preliminary Report on Patentability for PCT/US2009/034703, dated Aug. 24, 2010.
Communication from EPO re: 10000486 dated Apr. 4, 2011, 4 pages.
European Search Report re: EP05025816 dated Jun. 23, 2006.
European Search Report for EP07006258.3 dated May 4, 2007, 4 pages.
European Search Report for EP07015905.8 dated Oct. 2, 2007, 2 pages.
European Search Report for EP07015906 dated Oct. 2, 2007.
European Search Report for EP07016222 dated Jan. 7, 2008.
European Search Report for EP09014651 dated Jan. 12, 2010.

(56) References Cited

OTHER PUBLICATIONS

European Search Report for EP10000629.5 dated Mar. 10, 2010, 4 pages.
European Search Report re: EP10000486 dated Apr. 23, 2010.
European Search Report re: 10004453 dated Jun. 15, 2010.
European Search Report for EP10011868.6 dated Dec. 6, 2010, 2 pages.
European Search Report for EP10011869 dated Jan. 20, 2011.
European Search Report for EP10011871.0 dated Dec. 3, 2010, 2 pages.
European Search Report for EP10011872 dated Apr. 20, 2011.
European Search Report for EP10012437 dated Apr. 28, 2011.
European Search Report for EP10186592.1 dated Jan. 19, 2011, 2 pages.
European Search Report for EP10184766 dated Apr. 20, 2011.
Extended European Search Report re: 07015905.8 dated Oct. 23, 2007.
Extended European Search Report re: 07016222.7 dated Jan. 30, 2008.
International Preliminary Examination Report re: PCT/US1998/10478 dated Dec. 11, 1999.
International Preliminary Report re: PCT/US2007/002688 dated Aug. 14, 2008.
International Preliminary Report re: PCT/US2008/060127 dated Oct. 13, 2009.
International Preliminary Report on Patentability re: PCT/US2008/064921 dated Dec. 1, 2009.
International Preliminary Report on Patentability re: PCT/US2008/0075849 dated Mar. 16, 2010.
International Preliminary Report re: PCT/US2008/087788 dated Jun. 22, 2010.
International Preliminary Report re: PCT/US2009/032693 dated Aug. 3, 2010.
International Preliminary Report re: PCT/US2009/040545 dated Oct. 19, 2010.
International Preliminary Report re: PCT/US2009/041685 dated Oct. 26, 2010.
International Preliminary Report re: PCT/US2011/035431 dated Nov. 6, 2012.
International Preliminary Report on Patentability re: PCT/US2011/040014 dated Dec. 14, 2012.
International Preliminary Report re: PCT/US2011/059238 dated May 7, 2013.
International Search Report for PCT/US1994/09631 dated Dec. 9, 1994.
International Search Report for PCT/US1998/10478 dated Sep. 23, 1998.
International Search Report for PCT/US2002/027525 dated Dec. 9, 2002, 3 pages.
International Search Report for PCT/US2003/030664 dated May 25, 2004.
International Search Report for PCT/2003/030666 dated Dec. 15, 2004.
International Search Report for PCT/US2003/025088 dated Dec. 29, 2003.
International Search Report re: PCT/US2003/030674 dated Sep. 2, 2004.
International Search Report re: PCT/US2004/014962 dated Feb. 24, 2005.
International Search Report for PCT/US2007/002688 dated Oct. 22, 2007.
International Search Report for PCT/US2007/074658 dated Jun. 12, 2007, 3 pages.
International Search Report for PCT/US2008/060127 dated Sep. 23, 2008, 5 pages.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/040545 dated Oct. 29, 2009.
International Search Report for PCT/US2009/041685 dated Dec. 22, 2009.
International Search Report for PCT/US2010/056898 dated Aug. 2, 2011.
International Search Report for PCT/US2010/060889 dated Oct. 11, 2011.
International Search Report for PCT/US2011/034660 dated Feb. 8, 2012.
International Search Report for PCT/US2011/035270 dated Jan. 12, 2012.
International Search Report for PCT/US2011/035271 dated Jan. 12, 2012.
International Search Report re: PCT/US2011/035431 dated Jan. 12, 2012.
International Search Report for PCT/US2011/059238 dated May 21, 2012.
Partial European Search Report re: EP05025816 dated Mar. 20, 2006.
Singapore Search Report for Singapore Patent Application No. 200702625-5 dated Nov. 26, 2008, 7 pages.
Singapore Search Report for Singapore Patent Application No. 200702350-0 dated Nov. 26, 2008, 6 pages.
Singapore Search Report for Singapore Patent Application No. 200703688-2 dated Nov. 26, 2008, 7 pages.
Supplementary European Search Report re: EP98923664 dated Jun. 12, 2001.
Supplementary European Search Report re: EP03752630 dated Nov. 17, 2005.
Supplementary European Search Report re: 03770556 dated Nov. 17, 2005.
Supplementary European Search Report re: 03754965 dated Nov. 18, 2005.
Supplementary European Search Report re: EP03785177 dated May 19, 2009.
Supplementary European Search Report re: 07017663 dated Nov. 7, 2007.

* cited by examiner

METHOD AND APPARATUS FOR ELEVATING RETAINERS ON SELF-RETAINING SUTURES

FIELD OF THE INVENTION

The present invention relates generally to methods of manufacturing self-retaining sutures and devices for elevating retainers on self-retaining sutures for surgical procedures, and their uses.

BACKGROUND

Sutures are commonly used for closing or binding together wounds in human or animal tissue, such as skin, muscles, tendons, internal organs, nerves, and blood vessels. Sutures can be formed from non-absorbable material such as silk, nylon, polypropylene, or cotton, or alternatively sutures can be formed from bio-absorbable material such as, but not limited to, homopolymers and/or copolymers of glycolide, lactide, p-dioxanone and ε-caprolactone.

A suture can include retainers protruding from the suture periphery. These retainers are arranged to allow passage of the self-retaining suture when drawn in one direction (with respect to the direction of protrusion of the retainer) through tissue. Such retainers, however, resist movement when the self-retaining suture is drawn in the opposite direction. Self-retaining sutures can reduce slippage of the suture and can optionally obviate knotting of the suture.

Sutures typically consist of a filamentous suture thread with a needle with a sharp point (attachment of sutures and surgical needles is described in U.S. Pat. Nos. 3,981,307, 5,084,063, 5,102,418, 5,123,911, 5,500,991, 5,722,991, 6,012,216, and 6,163,948, and U.S. Patent Application Publication No. 2004/0088003).

Self-retaining sutures (often referred to as "self-retaining sutures") differ from conventional sutures in that they possess numerous tiny retainers (often barbs) which anchor into the surrounding tissue following deployment, thereby eliminating the need to tie knots to affix adjacent tissues together, and have been described in, for example, U.S. Pat. No. 6,848,152 and European Patent 1 075 843. Such retainers protrude from the suture periphery and are arranged to allow passage of the self-retaining suture when drawn in one direction (with respect to the direction of protrusion of the retainer) through tissue but resist movement of the self-retaining suture when drawn in the opposite direction. Retainers can reduce slippage of the suture at least in a direction along the suture and can optionally obviate knotting of the suture.

A self-retaining suture may be unidirectional, having one or more retainers oriented in one direction along the length of the suture thread; or bidirectional, typically having one or more retainers oriented in one direction along a portion of the thread, followed by one or more retainers oriented in another (often opposite) direction over the remainder of the thread (as described in the context of barbed retainers in U.S. Pat. Nos. 5,931,855 and 6,241,747). Although any number of sequential or intermittent configurations of retainers are possible, the most common form involves a needle at one end, followed by barbs projecting "away" from the needle until the transition point (often the midpoint) of the suture is reached; at the transition point the configuration of barbs reverses itself 180° (i.e., the barbs are now facing in the opposite direction) along the remaining length of the suture thread before attaching to a second needle at the opposite end. The disclosures of all patents and patent applications mentioned herein are incorporated by reference.

Single-directional self-retaining sutures can include an end that is pointed or has a needle to allow penetration and passage through tissue when drawn by the end and, if desired, an opposite end that includes an anchor for engaging tissue at the initial insertion point to limit movement of the suture. Alternatively, bi-directional self-retaining sutures can include retainers grouped and extending in one direction along one portion of the suture and opposing retainers grouped and extending in an opposing direction along another portion of the suture. When implanted, so that both groups of retainers are engaging tissue, the retainers can resist movement of the suture through tissue in either direction.

A surgeon may use a surgical needle with an attached suture to pierce the tissue alternately on opposing faces of a wound to sew the wound closed. Techniques for placement of self-retaining sutures in tissue to close or bind together wounds can include threading the self-retaining suture in straight-line patterns such as a zig-zag pattern as well as threading the suture in curvilinear patterns such as alpha, sinusoidal, and corkscrew patterns. A surgeon may also use self-retaining sutures to position and support tissue where there is no wound in procedures such as cosmetic surgery of the face, neck, abdominal or thoracic region among others.

More specifically, self-retaining sutures can be used in superficial and deep surgical procedures in humans and animals for closing wounds, repairing traumatic injuries or defects, joining tissues together [bringing severed tissues into approximation, closing an anatomical space, affixing single or multiple tissue layers together, creating anastomoses between two hollow (luminal) structures, adjoining tissues, attaching or reattaching tissues to their proper anatomical location], attaching foreign elements to tissues (affixing medical implants, devices, prostheses and other functional or supportive devices), and for repositioning tissues to new anatomical locations (repairs, tissue elevations, tissue grafting and related procedures) to name but a few examples.

Sutures typically consist of a filamentous suture thread attached to a needle with a sharp point (attachment of sutures and surgical needles is described in U.S. Pat. Nos. 3,981,307, 5,084,063, 5,102,418, 5,123,911, 5,500,991, 5,722,991, 6,012,216, and 6,163,948, and U.S. Patent Application Publication No. U.S. 2004/0088003). Classically, the needle is advanced through the desired tissue on one side of the wound and then through the adjacent side of the wound to form a "loop" which is then completed by tying a knot in the suture.

Sutures materials are broadly classified as being degradable or bioabsorbable (i.e., they break down completely in the body over time), such as those composed of catgut, glycolic acid polymers and copolymers, lactic acid polymers and copolymers, and polyether-esters based copolymers such as polyglycolide or lactide copolymers with polyglycols or polyethers; or as being non-absorbable (permanent; nondegradable), such as those made of polyamide, polytetrafluoroethylene, polyethylene terephthalate, polyurethane, polyether-esters based copolymers such as polybutylene or polyethylene terephthalate with polyglycols or polyethers, metal alloys, metal (e.g., stainless steel wire), polypropylene, polyethelene, silk, and cotton. Degradable (bioabsorbable) sutures have been found to be particularly useful in situations where suture removal might jeopardize the repair or where the natural healing process renders the support provided by the suture material unnecessary after wound healing has been completed; as in, for example, completing an uncomplicated skin closure. Nondegradable (non-absorbable) sutures are used in wounds where healing may be expected to be protracted or where the suture material is needed to provide physical support to the wound for long periods of time; as in, for example, deep tissue repairs, high tension wounds, many orthopedic repairs and some types of surgical anastomoses.

Bioabsorbable sutures can be made of materials which are broken down in tissue after a given period of time, which depending on the material can be from ten days to eight weeks. The sutures are used therefore in many of the internal tissues of the body. In most cases, three weeks is sufficient for the wound to close firmly. At that time the suture is not needed any more, and the fact that it disappears is an advantage, as there is no foreign material left inside the body and no need for the patient to have the sutures removed. In rare cases, bioabsorbable sutures can cause inflammation and be rejected by the body rather than absorbed. Bioabsorbable sutures were first made from the intestines of mammals. For example, gut sutures can be made of specially prepared bovine or ovine intestine, and can be untreated (plain catgut), tanned with chromium salts to increase the suture persistence in the body (chromic catgut), or heat-treated to give more rapid absorption (fast catgut). Concern about transmitting diseases such as bovine spongiform encephalopathy, has resulted in the gut being harvested from stock which have been tested to determine that the natural polymers used as suture materials do not carry viral diseases. Bioabsorbable sutures can be made of synthetic polymer fibers, which can be monofilaments or braided.

Self-retaining sutures are designed for engaging tissue when the suture is pulled in a direction other than that in which it was originally deployed in the tissue. Knotless tissue-approximating devices having barbs have been previously described in, for example, U.S. Pat. No. 5,374,268, disclosing armed anchors having barb-like projections, while suture assemblies having barbed lateral members have been described in U.S. Pat. Nos. 5,584,859 and 6,264,675. One of the earlier patents describing a self-retaining suture is U.S. Pat. No. 3,716,058, which discloses a suture having one or more relatively rigid barbs at its opposite ends; the presence of the barbs just at the ends of the suture would limit the barbs' effectiveness. Sutures having a plurality of barbs positioned along a greater portion of the suture are described in U.S. Pat. No. 5,931,855, which discloses a unidirectional self-retaining suture, and U.S. Pat. No. 6,241,747, which discloses a bidirectional self-retaining suture. Methods and apparatus for forming barbs on sutures by cutting barbs into a suture body have been described in, for example, U.S. Pat. Nos. 6,848,152 and 7,225,512. Methods of manufacturing sutures with frusto-conical retainers have also been described, for example, in European Patent 1 075 843 and U.S. Patent Publication No. 2007/0038429.

Despite the advantages of existing self-retaining sutures, there still remains a need and desire for new and preferably improved self-retaining sutures, and methods of making the same. For example, retainers formed by cutting into a suture body have a tendency to sometimes lie flat, i.e., not stand up or fan out as desired. Additionally, many existing techniques (e.g., cutting techniques) for manufacturing self-retaining sutures result in retainers having elevation angles that are less than desired.

SUMMARY

Provided herein are sutures to be used in a procedure applied to tissue, and methods for forming such sutures. A suture can include an elongated suture body with a plurality of retainers formed along at least a portion of the elongated suture body. In accordance with embodiments of the present invention, the retainers are elevated from original elevation angles to increased elevation angles, relative to a longitudinal axis of the elongated suture body. The details of such embodiments are set forth in the description below.

Other features, objects and advantages will be apparent from the description, the drawings, and the claims. In addition, the disclosures of all patents, patent applications, patent publications and other publications referenced herein are incorporated by reference in their entirety.

BRIEF DESCRIPTION OF THE DRAWINGS

The accompanying drawings, which are incorporated into and constitute a part of this specification, illustrate one or more embodiments and, together with the detailed description, serve to explain the principles and implementations of the invention. In the drawings.

DETAILED DESCRIPTION

Figure 1A:
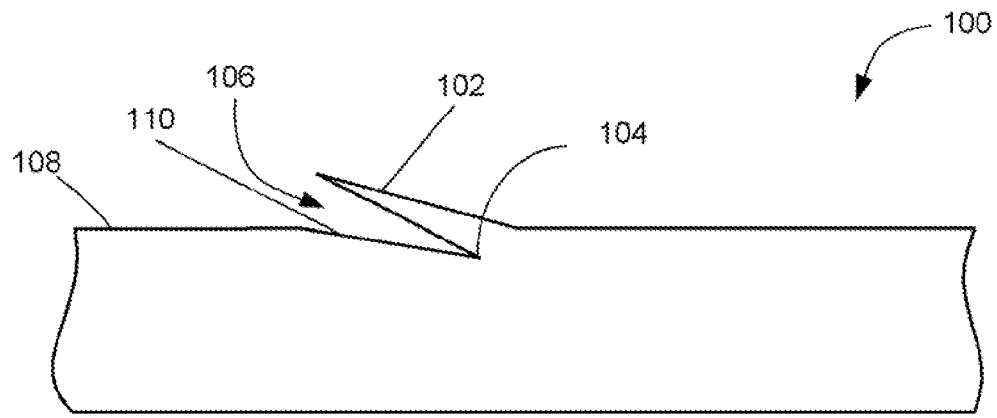
FIG. 1A illustrates a side view of a suture including a retainer in accordance with the prior art.

Definitions of certain terms that are used hereinafter are set forth below.

"Self-retaining system" refers to a self-retaining suture together with devices for deploying the suture into tissue. Such deployment devices include, without limitation, suture needles and other deployment devices as well as sufficiently rigid and sharp ends on the suture itself to penetrate tissue.

"Self-retaining suture" refers to a suture that comprises features on the suture filament for engaging tissue without the need for a knot or suture anchor at its end in order to maintain its position into which it is deployed during a surgical procedure. These may be monofilament sutures or braided sutures, and are positioned in tissue in two stages, namely deployment and affixation, and include at least one tissue retainer.

"Tissue retainer" (or simply "retainer") refers to a physical feature of a suture filament which is adapted to mechanically engage tissue and resist movement of the suture in at least one axial direction. By way of example only, tissue retainer or retainers can include hooks, projections, barbs, darts, extensions, bulges, anchors, protuberances, spurs, bumps, points, cogs, tissue engagers, traction devices, surface roughness, surface irregularities, surface defects, edges, facets and the like. In certain configurations, tissue retainers are adapted to engage tissue to resist movement of the suture in a direction other than the direction in which the suture is deployed into the tissue by the surgeon, by being oriented to substantially face the deployment direction. In some embodiments the retainers lie flat when pulled in the deployment direction and open or "fan out" when pulled in a direction contrary to the deployment direction. As the tissue-penetrating end of each retainer faces away from the deployment direction when moving through tissue during deployment, the tissue retainers should not catch or grab tissue during this phase. Once the self-retaining suture has been deployed, a force exerted in another direction (often substantially opposite to the deployment direction) causes the retainers to be displaced from the deployment position (i.e. resting substantially along the suture body), forces the retainer ends to open (or "fan out") from the suture body in a manner that catches and penetrates into the surrounding tissue, and results in tissue being caught between the retainer and the suture body; thereby "anchoring" or affixing the self-retaining suture in place. In certain other embodiments, the tissue retainers may be configured to permit motion of the suture in one direction and resist movement of the suture in another direction without fanning out or deploying. In certain other configurations, the tissue retainer may be configured or combined with other tissue retainers to resist motion of the suture filament in both directions. Typically a suture having such retainers is deployed through a device such as a cannula which prevents contact between the retainers and the tissue until the suture is in the desired location.

"Retainer configurations" refers to configurations of tissue retainers and can include features such as size, shape, flexibility, surface characteristics, and so forth.

"Bidirectional suture" refers to a self-retaining suture having retainers oriented in one direction at one end and retainers oriented in the other direction at the other end. A bidirectional suture is typically armed with a needle at each end of the suture thread. Many bidirectional sutures have a transition segment located between the two retainer orientations.

"Transition segment" refers to a retainer-free portion of a bidirectional suture located between a first set of retainers oriented in one direction and a second set of retainers oriented in another direction. The transition segment can be at about the midpoint of the self-retaining suture, or closer to one end of the self-retaining suture to form an asymmetrical self-retaining suture system.

"Suture thread" refers to the filamentary body component of the suture. The suture thread may be a monofilament, or comprise multiple filaments as in a braided suture. The suture thread may be made of any suitable biocompatible material, and may be further treated with any suitable biocompatible material, whether to enhance the sutures' strength, resilience, longevity, or other qualities, or to equip the sutures to fulfill additional functions besides joining tissues together, repositioning tissues, or attaching foreign elements to tissues.

"Monofilament suture" refers to a suture comprising a monofilamentary suture thread.

"Braided suture" refers to a suture comprising a multifilamentary suture thread. The filaments in such suture threads are typically braided, twisted, or woven together.

"Degradable (also referred to as "biodegradable" or "bioabsorbable") suture" refers to a suture which, after introduction into a tissue is broken down and absorbed by the body. Typically, the degradation process is at least partially performed in a biological system. "Degradation" refers to a chain scission process by which a polymer chain is cleaved into oligomers and monomers. Chain scission may occur through various mechanisms, including, for example, by chemical reaction (e.g., hydrolysis, oxidation/reduction, enzymatic mechanisms or a combination or these) or by a thermal or photolytic process. Polymer degradation may be characterized, for example, using gel permeation chromatography (GPC), which monitors the polymer molecular mass changes during erosion and breakdown. Degradable suture material may include polymers such as catgut, polyglycolic acid, lactic acid polymers, polyether-esters (e.g., copolymers of polyglycolide with polyglycols, polyglycolide with polyethers, polylactic acid with polyglycols or polylactic acid with polyethers), copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™ [glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). These sutures can be in either a braided multifilament form or a monofilament form. The polymers used in the present invention can be linear polymers, branched polymers or multi-axial polymers. Examples of multi-axial polymers used in sutures are described in U.S. Patent Application Publication Nos. 20020161168, 20040024169, and 20040116620. Degradable sutures can also include dissolvable sutures made of a dissolvable polymer, such as a polyvinyl alcohol partly deacetylated polymer, but not limited thereto. Sutures made from degradable suture material lose tensile strength as the material degrades. Absorbable sutures are defined by the loss of most of their tensile strength within 60 days after placement. Absorbable sutures are used primarily as buried sutures to close the dermis and subcutaneous tissue and reduce wound tension. The only natural absorbable suture available is surgical catgut. Synthetic multifilamentous absorbable materials include polyglycolic acid and polyglactin. Monofilamentous absorbable forms include polydioxanone, polytrimethylene carbonate, and polycaprone.

"Non-degradable (also referred to as "non-absorbable") suture" refers to a suture comprising material that is not degraded by chain scission such as chemical reaction processes (e.g., hydrolysis, oxidation/reduction, enzymatic mechanisms or a combination or these) or by a thermal or photolytic process. Non-degradable suture material includes polyamide (also known as nylon, such as nylon 6 and nylon 6.6), polyethylene terephthlate, polytetrafluoroethylene, polyether-ester (such as polybutylene or polyethylene terepthalate based copolymers with polyglycols or polyethers), polyurethane, metal alloys, metal (e.g., stainless steel wire), polypropylene, polyethelene, silk, and cotton. Sutures made of non-degradable suture material are suitable for applications in which the suture is meant to remain permanently or is meant to be physically removed from the body. Nonabsorbable sutures are defined by the resistance of the suture to degradation by living tissues. Nonabsorbable sutures are most useful in percutaneous closures. Silk, cotton, and linen are natural nonabsorbable materials. Synthetic monofilament nonabsorbable sutures including nylon, polypropylene, and polybutester, are used in cutaneous procedures. Synthetic multifilament nonabsorbable suture include nylon and polyester.

Sutures materials are broadly classified as being degradable or bioabsorbable (i.e., they break down completely in the body over time), such as those composed of catgut, glycolic acid polymers and copolymers, lactic acid polymers and copolymers, and polyether-esters based copolymers such as polyglycolide or lactide copolymers with polyglycols or polyethers; or as being non-absorbable (permanent; nondegradable), such as those made of polyamide, polytetrafluoroethylene, polyethylene terephthalate, polyurethane, polyether-esters based copolymers such as polybutylene or polyethylene terephthalate with polyglycols or polyethers, metal alloys, metal (e.g., stainless steel wire), polypropylene, polyethelene, silk, and cotton. Degradable (bioabsorbable) sutures have been found to be particularly useful in situations where suture removal might jeopardize the repair or where the natural healing process renders the support provided by the suture material unnecessary after wound healing has been completed; as in, for example, completing an uncomplicated skin closure. Nondegradable (non-absorbable) sutures are used in wounds where healing may be expected to be protracted or where the suture material is needed to provide physical support to the wound for long periods of time; as in, for example, deep tissue repairs, high tension wounds, many orthopedic repairs and some types of surgical anastomoses.

It is important to understand that the classification of bioabsorbable and non-degradable or non-bioabsorbable sutures is not absolute. For example, most polyesters are non-bioabsorbable (such as polyethylene terephthalate) except that some polyesters (such as those made from polyglycolic acid, polylactic acid, or polyhydroxyalkanoates) are bioabsorbable. Similarly, silk is generally considered as a non-bioabsorbable material, but over a long period of time (e.g., 10 to 25 years), the body can break-down silk sutures implanted in the body.

Bioabsorbable sutures can be made of materials which are broken down in tissue after a given period of time, which depending on the material can be from ten days to eight weeks. The sutures are used therefore in many of the internal tissues of the body. In most cases, three weeks is sufficient for the wound to close firmly. At that time the suture is not needed any more, and the fact that it disappears is an advantage, as there is no foreign material left inside the body and no need for the patient to have the sutures removed. In rare cases, bioabsorbable sutures can cause inflammation and be rejected by the body rather than absorbed. Bioabsorbable sutures were first made from the intestines of mammals. For example, gut sutures can be made of specially prepared bovine or ovine intestine, and can be untreated (plain catgut), tanned with chromium salts to increase the suture persistence in the body (chromic catgut), or heat-treated to give more rapid absorption (fast catgut). Concern about transmitting diseases such as bovine spongiform encephalopathy, has resulted in the gut being harvested from stock which have been tested to determine that the natural polymers used as suture materials do not carry viral diseases. Bioabsorbable sutures can be made of synthetic polymer fibers, which can be monofilaments or braided.

"Suture diameter" refers to the diameter of the body of the suture. It is to be understood that a variety of suture lengths may be used with the sutures described herein and that while the term "diameter" is often associated with a circular periphery, it is to be understood herein to indicate a cross-sectional dimension associated with a periphery of any shape. Suture sizing is based upon diameter. United States Pharmacopeia ("USP") designation of suture size runs from 0 to 7 in the larger range and 1-0 to 11-0 in the smaller range; in the smaller range, the higher the value preceding the hyphenated zero, the smaller the suture diameter. The actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures may be more easily manipulated through tight surgical sites and are associated with less scarring, the tensile strength of a suture manufactured from a given material tends to decrease with decreasing size. It is to be understood that the sutures and methods of manufacturing sutures disclosed herein are suited to a variety of diameters, including without limitation 7, 6, 5, 4, 3, 2, 1, 0, 1-0, 2-0, 3-0, 4-0, 5-0, 6-0, 7-0, 8-0, 9-0, 10-0 and 11-0.

"Suture deployment end" refers to an end of the suture to be deployed into tissue; one or both ends of the suture may be suture deployment ends. The suture deployment end may be attached to a deployment device such as a suture needle, or may be sufficiently sharp and rigid to penetrate tissue on its own.

"Armed suture" refers to a suture having a suture needle on at least one suture deployment end.

"Needle attachment" refers to the attachment of a needle to a suture requiring same for deployment into tissue, and can include methods such as crimping, swaging, using adhesives, and so forth. The suture thread is attached to the suture needle using methods such as crimping, swaging and adhesives. Attachment of sutures and surgical needles is described in U.S. Pat. Nos. 3,981,307, 5,084,063, 5,102,418, 5,123,911, 5,500,991, 5,722,991, 6,012,216, and 6,163,948, and U.S. Patent Application Publication No. US 2004/0088003). The point of attachment of the suture to the needle is known as the swage.

"Suture needle" refers to needles used to deploy sutures into tissue, which come in many different shapes, forms and compositions. There are two main types of needles, traumatic needles and atraumatic needles. Traumatic needles have channels or drilled ends (that is, holes or eyes) and are supplied separate from the suture thread and are threaded on site. Atraumatic needles are eyeless and are attached to the suture at the factory by swaging or other methods whereby the suture material is inserted into a channel at the blunt end of the needle which is then deformed to a final shape to hold the suture and needle together. As such, atraumatic needles do not require extra time on site for threading and the suture end at the needle attachment site is generally smaller than the needle body. In the traumatic needle, the thread comes out of the needle's hole on both sides and often the suture rips the tissues to a certain extent as it passes through. Most modern sutures are swaged atraumatic needles. Atraumatic needles may be permanently swaged to the suture or may be designed to come off the suture with a sharp straight tug. These "pop-offs" are commonly used for interrupted sutures, where each suture is only passed once and then tied. For self-retaining sutures that are uninterrupted, these atraumatic needles are preferred.

Suture needles may also be classified according to the geometry of the tip or point of the needle. For example, needles may be (i) "tapered" whereby the needle body is round and tapers smoothly to a point; (ii) "cutting" whereby the needle body is triangular and has a sharpened cutting edge on the inside; (iii) "reverse cutting" whereby the cutting edge is on the outside; (iv) "trocar point" or "taper cut" whereby the needle body is round and tapered, but ends in a small triangular cutting point; (v) "blunt" points for sewing friable tissues; (vi) "side cutting" or "spatula points" whereby the needle is flat on top and bottom with a cutting edge along the front to one side (these are typically used for eye surgery).

Suture needles may also be of several shapes including, (i) straight, (ii) half curved or ski, (iii) ¼ circle, (iv) ⅜ circle, (v) ½ circle, (vi) ⅝ circle, (v) and compound curve.

Suturing needles are described, for example, in U.S. Pat. Nos. 6,322,581 and 6,214,030 (Mani, Inc., Japan); and U.S. Pat. No. 5,464,422 (W. L. Gore, Newark, Del.); and U.S. Pat. Nos. 5,941,899; 5,425,746; 5,306,288 and 5,156,615 (US Surgical Corp., Norwalk, Conn.); and U.S. Pat. No. 5,312,422 (Linvatec Corp., Largo, Fla.); and U.S. Pat. No. 7,063,716 (Tyco Healthcare, North Haven, Conn.). Other suturing needles are described, for example, in U.S. Pat. Nos. 6,129, 741; 5,897,572; 5,676,675; and 5,693,072. The sutures described herein may be deployed with a variety of needle types (including without limitation curved, straight, long, short, micro, and so forth), needle cutting surfaces (including without limitation, cutting, tapered, and so forth), and needle attachment techniques (including without limitation, drilled end, crimped, and so forth). Moreover, the sutures described herein may themselves include sufficiently rigid and sharp ends so as to dispense with the requirement for deployment needles altogether.

"Needle diameter" refers to the diameter of a suture deployment needle at the widest point of that needle. While the term "diameter" is often associated with a circular periphery, it is to be understood herein to indicate a cross-sectional dimension associated with a periphery of any shape.

"Wound closure" refers to a surgical procedure for closing of a wound. An injury, especially one in which the skin or another external or internal surface is cut, torn, pierced, or otherwise broken is known as a wound. A wound commonly occurs when the integrity of any tissue is compromised (e.g., skin breaks or burns, muscle tears, or bone fractures). A wound may be caused by an act, such as a puncture, fall, or surgical procedure; by an infectious disease; or by an underlying medical condition. Surgical wound closure facilitates the biological event of healing by joining, or closely approximating, the edges of those wounds where the tissue has been torn, cut, or otherwise separated. Surgical wound closure directly apposes or approximates the tissue layers, which serves to minimize the volume new tissue formation required to bridge the gap between the two edges of the wound. Closure can serve both functional and aesthetic purposes. These purposes include elimination of dead space by approximating the subcutaneous tissues, minimization of scar formation by careful epidermal alignment, and avoidance of a depressed scar by precise eversion of skin edges.

"Tissue elevation procedure" refers to a surgical procedure for repositioning tissue from a lower elevation to a higher elevation (i.e. moving the tissue in a direction opposite to the direction of gravity). The retaining ligaments of the face support facial soft tissue in the normal anatomic position. However, with age, gravitational effects and loss of tissue volume effect downward migration of tissue, and fat descends into the plane between the superficial and deep facial fascia, thus causing facial tissue to sag. Face-lift procedures are designed to lift these sagging tissues, and are one example of a more general class of medical procedure known as a tissue elevation procedure. More generally, a tissue elevation procedure reverses the appearance change that results from effects of aging and gravity over time, and other temporal effects that cause tissue to sag, such as genetic effects. It should be noted that tissue can also be repositioned without elevation; in some procedures tissues are repositioned laterally (away from the midline), medially (towards the midline) or inferiorly (lowered) in order to restore symmetry (i.e. repositioned such that the left and right sides of the body "match").

"Medical device" or "implant" refers to any object placed in the body for the purpose of restoring physiological function, reducing/alleviating symptoms associated with disease, and/or repairing and/or replacing damaged or diseased organs and tissues. While normally composed of biologically compatible synthetic materials (e.g., medical-grade stainless steel, titanium and other metals or polymers such as polyurethane, silicon, PLA, PLGA and other materials) that are exogenous, some medical devices and implants include materials derived from animals (e.g., "xenografts" such as whole animal organs; animal tissues such as heart valves; naturally occurring or chemically-modified molecules such as collagen, hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants). Medical devices that can be used in procedures in conjunction with the present invention include, but are not restricted to, orthopedic implants (artificial joints, ligaments and tendons; screws, plates, and other implantable hardware), dental implants, intravascular implants (arterial and venous vascular bypass grafts, hemodialysis access grafts; both autologous and synthetic), skin grafts (autologous, synthetic), tubes, drains, implantable tissue bulking agents, pumps, shunts, sealants, surgical meshes (e.g., hernia repair meshes, tissue scaffolds), fistula treatments, spinal implants (e.g., artificial intervertebral discs, spinal fusion devices, etc.) and the like.

Self-retaining sutures (including self-retaining sutures) differ from conventional sutures in that they possess numerous tiny tissue retainers (such as barbs) which anchor into the tissue following deployment and resist movement of the suture in a direction opposite to that in which the retainers face, thereby eliminating the need to tie knots to affix adjacent tissues together (a "knotless" closure). By eliminating knot tying, associated complications are eliminated, including, but not limited to (i) spitting (a condition where the suture, usually a knot) pushes through the skin after a subcutaneous closure), (ii) infection (bacteria are often able to attach and grow in the spaces created by a knot), (iii) bulk/mass (a significant amount of suture material left in a wound is the portion that comprises the knot), (iv) slippage (knots can slip or come untied), and (v) irritation (knots serve as a bulk "foreign body" in a wound). Suture loops associated with knot tying may lead to ischemia (they create tension points that can strangulate tissue and limit blood flow to the region) and increased risk of dehiscence or rupture at the surgical wound. Knot tying is also labor intensive and can comprise a significant percentage of the time spent closing a surgical wound. Additional operative procedure time is not only bad for the patient (complication rates rise with time spent under anesthesia), but it also adds to the overall cost of the operation (many surgical procedures are estimated to cost between $15 and $30 per minute of operating time). Thus, knotless sutures not only allow patients to experience an improved clinical outcome, but they also save time and costs associated with extended surgeries and follow-up treatments.

Self-retaining systems for wound closure also result in better approximation of the wound edges, evenly distribute the tension along the length of the wound (reducing areas of tension that can break or lead to ischemia), decrease the bulk of suture material remaining in the wound (by eliminating knots) and reduce spitting (the extrusion of suture material—typically knots—through the surface of the skin. All of these features are thought to reduce scarring, improve cosmesis, and increase wound strength relative to wound closures effected with plain sutures or staples.

The ability of self-retaining sutures to anchor and hold tissues in place even in the absence of tension applied to the suture is a feature that also provides superiority over plain sutures. When closing a wound that is under tension, this advantage manifests itself in several ways: (i) a multiplicity of retainers can dissipate tension along the entire length of the suture (providing hundreds of "anchor" points as opposed to knotted interrupted sutures which concentrate the tension at discrete points; this produces a superior cosmetic result and lessens the chance that the suture will "slip" or pull through); (ii) complicated wound geometries can be closed (circles, arcs, jagged edges) in a uniform manner with more precision and accuracy than can be achieved with interrupted sutures;

(iii) they eliminate the need for a "third hand" which is often required for maintaining tension across the wound during traditional suturing and knot tying (to prevent "slippage" when tension is momentarily released during tying); (iv) they are superior in procedures where knot tying is technically difficult, such as in deep wounds or laparoscopic procedures; and (v) they can be used to approximate and hold the wound prior to definitive closure. As a result, self-retaining sutures provide easier handling in anatomically tight or deep places (such as the pelvis, abdomen and thorax) and make it easier to approximate tissues in laparoscopic and minimally invasive procedures; all without having to secure the closure via a knot. Greater accuracy allows self-retaining sutures to be used for more complex closures (such as those with diameter mismatches, larger defects or purse string suturing) than can be accomplished with plain sutures.

Self-retaining sutures also lend themselves to a variety of specialized indications; for example, they are suitable for tissue elevation procedures where tissue is moved from its previous location and repositioned into a new anatomical location (this is typically performed in cosmetic procedures where "drooping" tissue is elevated and fixed in a more "youthful" position; or where "out-of-position" tissue is moved back to its correct anatomical location). Such procedures include facelifts, brow lifts, breast lifts, buttocks lifts, and so forth.

A self-retaining suture may be unidirectional, having one or more retainers oriented in one direction along the length of the suture thread; or bidirectional, typically having one or more retainers oriented in one direction along a portion of the thread, followed by one or more retainers oriented in another (often opposite) direction over the remainder of the thread (as described with barbed retainers in U.S. Pat. Nos. 5,931,855 and. 6,241,747).

Although any number of sequential or intermittent configurations of retainers are possible, a common form involves a needle at one end, followed by retainers projecting "away" from the needle until the transition point (often the midpoint) of the suture is reached; at the transition point the configuration of retainers reverses itself about 180° (such that the retainers are now facing in the opposite direction) along the remaining length of the suture thread before attaching to a second needle at the opposite end (with the result that the retainers on this portion of the suture also face away from the nearest needle). Put another way, the retainers on both "halves" of a bidirectional self-retaining suture point towards the middle, with a transition segment (lacking retainers) interspersed between them, and with a needle attached to either end.

As mentioned above, despite the multitude of advantages of self-retaining sutures, there remains a need and desire to improve upon the design of such sutures so that a variety of common limitations can be eliminated. For example, retainers formed by cutting into a suture body have a tendency to sometimes lie flat, i.e., not stand up or fan out as desired. Additionally, many existing techniques (e.g., cutting techniques) for manufacturing self-retaining sutures result in retainers having elevation angles that are less than desired. Embodiments of the present invention, described below, can be used to increase the elevation angles of retainers. Additionally, embodiments of the present invention, described below, can be used to reduce the tendency that retainers have to lie flat.

As set forth in the background, sutures are commonly used for closing or binding together wounds in human or animal tissue, such as skin, muscles, tendons, internal organs, nerves, and blood vessels. Nevertheless, a number of problems can arise when using current wound closure systems to augment the healing process. In suture wound closure systems, ideally the suture distributes stress along the entire suture length. Most suture systems require a knot to secure the suture in the wound. However, the knot decreases the tensile strength of the entire suture. Once a knotted suture breaks, the suture can pullout resulting in wound dehiscence. Knotted sutures can also lead to inflammation.

In suture systems that incorporate retainers to retain the suture in the wound, a knot is not required. The self-retaining suture distributes the load required to keep the suture in place, along the length of the suture, and thereby keeps the wound securely closed. The polymer used to make the self-retaining suture can also be chosen to maintain the required strength for the duration of the healing process.

While the benefits of using self-retaining sutures are readily apparent, the goal of obtaining elevated retainers is often made difficult by various factors such as cutting conditions and/or material properties. For example, barbs cut and bent into a certain angle of elevation may relax to a less prone position post-manufacturing (during sterilization, attachment, etc.) and prior to implantation due to the residual stresses in the suture material and/or viscoelastic effects. This may decrease the effectiveness of the self-retaining suture when used to close a wound. Accordingly, the current invention includes methods and apparatuses for permanently elevating retainers to a desired angle and imposing a desired geometry to obtain maximum self-retaining suture engagement force in tissues. The mechanism uses mechanical bending of retainers post cutting to achieve an optimal angle of retainer elevation and retainer geometry.

Figure 1B:
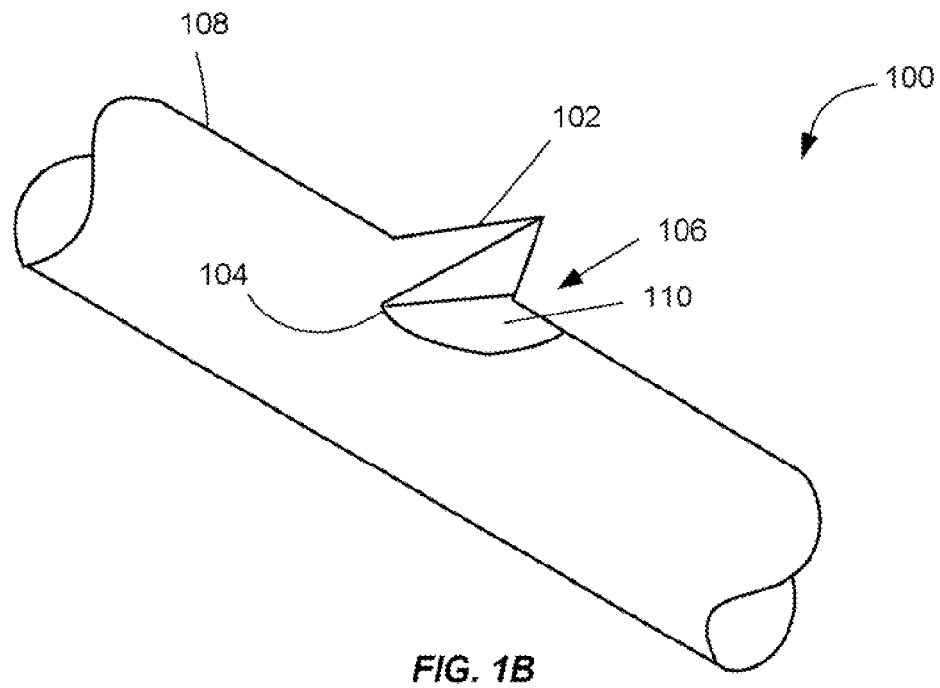
FIG. 1B illustrates a perspective view of a suture including a retainer in accordance with the prior art.

FIGS. 1A to 10D:

FIG. 1A is a side view and FIG. 1B is a perspective view of a suture 100 including a retainer 102 protruding from a periphery 108 of the suture 100 in accordance with the prior art. Retainers can have a variety of geometric shapes, for example pyramidal and conical. The retainer 102 can be formed when a cutting edge (not shown) is brought into contact with the suture 100 so that the cutting edge penetrates the periphery of the suture 100. The cutting edge forms a wedge cut 104 having an apex 106 at a termination point of the cutting edge's penetration. The retainer 102 is urged apart from the suture 100 so that the retainer 102 is gapped to form a retainer channel 110 opening from the periphery 108 of the suture 100 from which the retainer 102 is separated. The apex 106 likely includes a small radius of curvature defined largely by a rounding of the cutting edge. For example, the cutting edge may be a knife blade including a rounded edge or, for example, the cutting edge may be a wire having a circular cross-section with a diameter.

A multiplicity of retainers 102 can also be formed along the entire length of the suture 100 using a cutting edge. One method of forming multiple retainers along the length of the suture involves cutting the suture 100 along one side thereof while the suture 100 is in a twisted configuration. Once the cuts have been made, the suture 100 can be untwisted, leaving the retainers 102 to spiral around the circumference 108 of the suture 102.

The retainers 102 depicted in FIGS. 1A and 1B can be formed by a number of methods and systems, and these retainers can be formed with a number of materials that are suitable for sutures. These retainer formation methods and systems and materials are described throughout. For example, cutting wheels, and grinding wheels can be used instead of knives and blades. In addition to the cutting techniques that use physical blades or knives to cut retainer, lasers can also be used to form the retainers. Such lasers include for example vaporizing lasers that include UV lasers and cutting lasers that include carbon dioxide lasers. The cutting or forming of retainers could also be accomplished by ion beam cutters, plasma or plasma torch cutters, mechanical blade cutters with heating elements, water jet cutters, air or gas jet cutters, microwave cutters, ultrasound cutters, and other formation methods and systems. U.S. Pat. No. 5,931,855, issued Aug. 3, 1999, entitled Surgical Methods Using One-Way Suture and listing Harry J. Buncke as an inventor, which is incorporated herein by reference in its entirety, describes a retainer cutting technique using a laser. In this method and system the laser is directed to the surface of the suture in order to remove material to form and define retainers between the sections of removed material. The retainers can be formed on opposite sides of the suture or staggered. Also the retainers can be formed in a spiral pattern by twisting the suture prior to the cutting process or moving the laser around the suture during the cutting process or the material removing process. Industrial lasers can be focused very sharply, down to the dimensions needed for forming such retainers.

Embodiments herein are directed to the elevation of retainers by any of the number of methods and systems described. Elevation is preferably imparted to the retainers in such a way that the retainers stay elevated so that when deployed into tissue the retainers engage the tissue in order to retain suture position. For many of the embodiments the retainers are elevated due to the imparting of energy to the retainer that caused the retainer to become and stay elevated. The energy imparted can, for example, be through the use of thermal energy, mechanical energy, chemical energy, elastic energy, electrostatic energy and/or electrical energy. Further combinations of these types of energy can be used to elevate retainers. Some or all of the cutting techniques described, such as, for example, the water jet, air or gas jet and sound wave methods as well as the beam methods, can also be used to elevate the retainers by, for example, applying a physical force to the retainers.

As described herein, one embodiment for retainer elevation places the suture under stress during retainer formation. Stress can be imparted to the filament of the suture by, for example, bending the suture around a radius or capstan or twisting the suture along the longitudinal axis of the suture. During the retainer formation process, such as by cutting, the process can relieve the stress and the retainer can elevate. Certain materials can be beneficially placed in stress using the above technique of running the suture over a radius or capstan in order to promote retainer elevation. Such materials can for example include, polypropylene, nylon, polydioxanone, and polybutester. Retainer elevation can be caused by the differential stress between the retainer and the rest of the suture. Further as described herein, the retainer can be formed, without the suture being initially placed in stress and post retainer formation, by using a wiper or brush or bending bar or roller or other elevation device to mechanically move the retainer into an elevated position by the application of mechanical stress or force to the retainer.

Alternatively, as described herein, a coating could be applied to the retainer, after retainer formation, in order to cause a differential contraction between the retainer and the rest of the suture to cause retainer elevation. Still alternatively, the suture itself can be initially formed of different materials and once the retainer is formed the materials act differently by contraction or other mechanisms in order to cause the retainer to become elevated. It is to be understood that these methods and systems can be used in different combinations and sequences. By way of example a retainer can be formed, then post processed using an embodiment described herein to elevate the retainer. In another sequence, prior to the retainer formation process, different materials can be used to make the suture, or the suture can be placed in stress, or heated or cooled, for example, before the retainer is formed in order to provide for retainer elevation after the formation of the retainer.

Embodiments can use thermal energy to elevate retainers. For example, a suture, preferably cold, could be processed with a laser to form retainers. The local application of heat to cut the retainer, could cause the retainer to elevate. A further embodiment that can be used in combination with a retainer formation step, can include using a stream 205 (FIG. 2B) of air or other gas or a fluid that is blown along the suture to mechanically raise the retainer to cause retainer elevation. A stream of a fluid, such as gas, which can be air, can be used to mechanically elevate retainers after a retainer formation step. Additionally, a strong and concentrated stream of a gas could cool the surface of the retainer at a different rate than the rest of the suture to cause retainer elevation. Further the mechanical force of the gas could cause retainer elevation. A stream of a gas could be used to cause the surface of the retainers to be coated with a chemical that could cause retainer elevation. Various types of chemical coatings or sprays are described herein that could cause retainer elevation.

Another method and system to elevate a retainer can be to initially cut a retainer and then to draw or pull the suture. The retainers, during the drawing process, would not be placed under stress as would the rest of the suture, and thus the retainers would tend to cool or be cooler than the rest of the suture. Further a process by differentially heating or cooling the retainers and the rest of the suture could cause retainer elevation. Also, cooling the suture, cutting the retainer and then heating the suture, could cause retainer elevation. Reversing the sequence, with the initially heating of the suture, the cutting of the retainer and the cooling of the suture, could also cause retainer elevation. Applying heat to the base of the retainer or to the underside of the retainer and then cooling the same location, with for example a stream of a gas, can also cause retainer elevation. Reversing the sequence and cooling and then heating the base of the retainer or the underside of the retainer could also cause retainer elevation.

Using a laser or other heating method or system can cause retainer elevation by changing the physical form of the suture material itself. Thus causing the suture material to have a crystalline structure can be used to induce retainer elevation. This method could cause a change in stress, which change can be used for retainer elevation as described herein.

With respect to sutures comprised of several materials, one embodiment can include a core of polypropylene which is covered or coated with a layer of polybutester. Forming or cutting a retainer in the polybutester would cause the retainer to elevate due to the different properties of the materials. In this case, the polybutester would lift away from the core of polypropylene.

Other techniques for causing retainers to become proud or remain proud are described in PCT Patent Application No. PCT/US2008/077813, filed on Sep. 26, 2008, entitled SELF-RETAINING SUTURES INCLUDING TISSUE RETAINERS HAVING IMPROVED STRENGTH and listing Robert A. Herrmann, Alexei Goraltchouk and Lev Drubetsky as inventors and which claims priority to U.S. Provisional Application No. 60/975,758, filed Sep. 27, 2007, which applications are also incorporated by reference herein in their entirety.

Figure 2A:
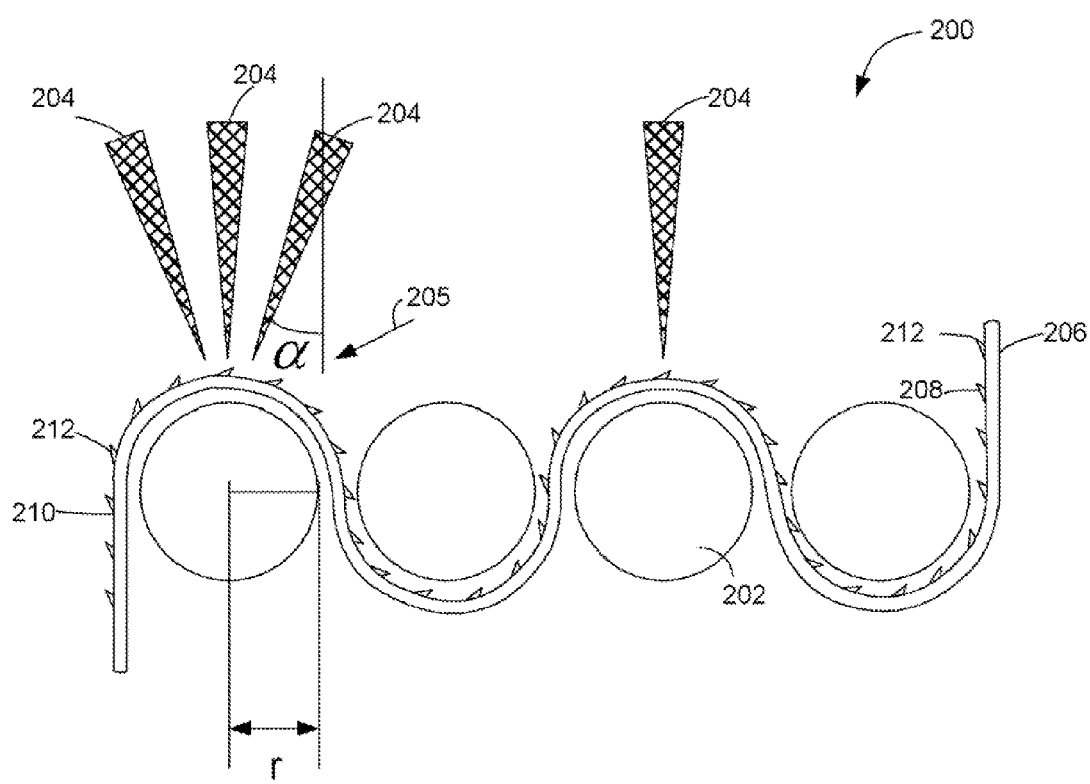
FIG. 2A illustrates a side view of an embodiment of an apparatus for elevating barbs to a desired angle according to the present invention including rollers and bending bars.

Referring now to FIG. 2A, an embodiment of an apparatus 200 for elevating retainers to a desired angle of the present invention is illustrated. Apparatus 200 includes rollers 202 and bending bars 204 used to elevate retainers 208 on a suture thread 206 to a desired angle. Apparatus 200 can be used after the retainers 208 have been created by a retainer-forming machine. In an embodiment, the apparatus 200 can be built into a retainer-forming machine immediately after the retainer-forming head, wherein the apparatus 200 accepts the suture while the suture thread 206 is still maintained in its twisted configuration to allow the retainers 208 in all directions to be elevated by the bending bars 204.

In the embodiment of the invention shown in FIG. 2A, the suture thread 206 is passed over rollers 202 to bend the suture thread 206 which causes the retainers 208 to elevate from the suture thread 206. As the retainers 208 are elevated from the suture thread 206, the retainers 208 can be bent further back by successive mechanical forces applied to the retainers 208 by the bending bars 204 to achieve an optimal angle of barb elevation. Mechanically applying a force to the retainers 208 through the use of bending bars 204 allows the retainers 208 to be bent back to a higher degree, as well as for a longer period of time, than would normally occur during cutting. Continuous deformation of the retainers 208 can promote their memorization of the elevated position by: (1) fatiguing the base adjoining the retainers 208, (2) causing creep of the retainer base, and (3) imposing a greater amount of plastic deformation. Permanent plastic deformation allows the retainers 208 on the suture 206 to memorize the upward positions of the retainers 208. It is noted that for some materials, it is essential to deform the retainers 208 after cutting, otherwise, the retainers 208 will relax back to their original configuration immediately after cutting if the suture is straightened out.

In an embodiment, rollers 202 and bending bars 204 can be used alone, or in a series, to facilitate the plastic deformation of the retainers 208 on a suture thread 206. Generally, deformation is a change in an object's shape due to an applied force. An object which undergoes elastic deformation will return to its original shape once a force is no longer applied to the object. An object which undergoes plastic deformation will not return to its original shape even when a force is no longer applied to the object as this type of deformation is not reversible. By using a combination of rollers 202 and bending bars 204 in a series as shown in FIG. 2A, mechanical forces can be cyclically applied to the retainers 208 until plastic deformation, fatigue and/or creep of the retainers 208 occurs. The specific number of rollers 202 and/or bending bars 204 used within the apparatus 200 can depend on, among other things, the physical characteristics of the suture 206, the temperature within the apparatus 200 including the temperature of the rollers 202, as well as the characteristics of the bending bars 204 used to apply the force.

Referring still to FIG. 2A, the number of bending bars 204 can effectively control the amount of times the retainers 208 are bent backwards. Accordingly, more bending bars 204 may be used for sutures having retainers 208 that have a strong tendency to relax back to the downward position. In an embodiment, the bending bars 204 can be flexible, and thereby bend back, as the bending bars 204 contact the retainers 208. This action allows for passage of the last portion of the retainer 208 with less stress to the tip 214 of the retainer 208. In another embodiment, the bending bars 204 can be configured at various angles with respect to the suture thread 206. A bending bar 204 which is positioned at a greater angle alpha, $\alpha$, may apply a greater force to the bulk of the retainers 208 as opposed to a bending bar 204 which is positioned at a lesser angle. In another embodiment, the proximity of the bending bars 204 relative to the suture thread may be varied. A bending bar 204 which is placed closer to the suture thread 206 near the base 210 of the retainers 208 will apply a greater force to the bulk of the retainers 208 as opposed to a bending bar 204 which is positioned further away from the suture thread 206 near the tip 212 of the retainers 208. In another embodiment, the bending bars 204 can be mechanically moved up and down during the bending process. For example, the bending bar 204 can be positioned adjacent to the base 210 of a retainer 208 as retainer 208 initially contacts the bending bar 204, and then the bending bar 204 can be withdrawn (moved up away from the suture thread 206) as the retainer 208 is being bent back by the bending bar 204. This action can prevent the retainer 208 from bending backwards at an undesirable angle to alleviate damaging the retainer 208. In another embodiment, the bending bar 204 can be moved back and forth along a retainer 208 to place an even greater force on the retainer 208. In yet another embodiment, the speed with which the suture thread 206 is pulled through the apparatus 200 may be varied to affect the duration of contact between the bending bars 204 and the retainers 208. The slower the speed with which the suture thread 206 is pulled through the apparatus 200, the greater the duration of contact between the bending bars 204 and the retainers 208, thereby resulting in increased creep and a decrease in the counteracting viscoelastic effect. It is noted that if more than one bending bar 204 is employed, decreasing the speed with which the suture thread 206 is pulled through the apparatus 200 will increase the duration of contact with respect to each individual bending bar 204, thereby non-linearly amplifying the overall mechanical force placed on a particular retainer 208 after it has passed through the apparatus 200.

In other embodiments of the invention, the geometry of a bending bar 204 can be varied to affect the aggressiveness of the deflection applied to a retainer 208 by the bending bar 204. For example, the geometry of a bending bar 204 can be configured to vary the initial point of contact between the bending bar 204 and a retainer 208. A bending bar 204 having a geometry which causes the bending bar 204 to have its initial point of contact closer to the base 210 of a retainer 208 is more aggressive, and thus can cause a greater amount of deflection, than a bending bar 204 having a geometry which causes the bending bar 204 to have its initial point of contact closer to the tip 212 of the retainer 208. In another example, the geometry of a bending bar 204 can be configured to increase the duration of contact between a bending bar 204 and a retainer 208. Increasing the duration of contact can increase the amount of deflection that a retainer 208 experiences. In yet another example, the geometry of the bending bar 204 can be configured to either contact a retainer 208 at a single point of contact or along a flat plane, the configuration resulting in contact at a single point being considered the more aggressive configuration, producing more deflection.

In the current embodiment of the invention, the suture 206 is passed over rollers 202, effectively bending the suture fiber and causing retainers 208 to elevate from the suture, bending the retainers 208 further back by successive mechanical force applied by the bending bars 204. This action allows the retainers 208 to bend to a higher degree than during cutting as well as allowing the retainer to bend backwards for a longer time (which may allow for annealing if an elevated temperature is used). Bending of retainers 208 to a higher degree than during cutting may allow the base of the retainer to undergo permanent plastic deformation, more readily causing the retainer to stay in an upward position. Because the time that the retainers 208 spend in an elevated position is increased, creep may onset allowing the retainers 208 to stay elevated, or relax downward to a lesser extent. The current apparatus 200 can be built into a retainer-forming machine after the retainer-forming head, while the suture 206 is in the twisted form to allow retainers 208 in all directions to be elevated by the bending bars 204. The number of bending bars 204 effectively control the amount each retainer is bent backwards (more bending bars are required for materials where retainers have a strong tendency to relax back to the down position). The bending bars 204 can themselves be flexible to allow for passage of the last portion of the retainer with less stress to the retainer tip 212. The bending bars 204 can be positioned at various angles α with respect to the suture strand. Retainers 208 that are positioned at a greater angle, may apply a higher force to the bulk of the retainers while bars that are positioned at a lower angle may apply a smaller force and tend to work on elevating the tip 212 of the retainer. In the same fashion, the geometry of the retainer 208 may be controlled (for example, retainers which are curled backward may also be produced). The geometry of the bending bar 204 can also be varied. The diameter of the roller controls the extent with which the retainers 208 protrude from the suture 206. Smaller diameter rolls will cause the retainers 208 to elevate further, while larger diameter rolls will cause the retainers to elevate less.

Figure 3A:
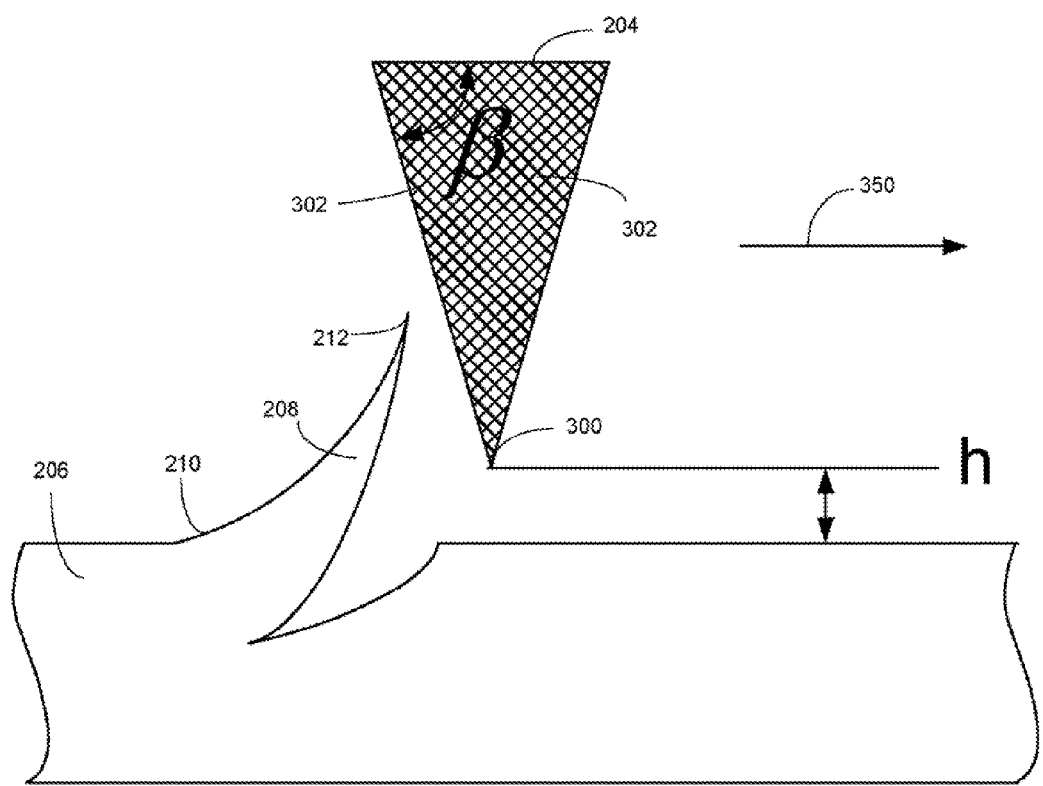
FIG. 3A illustrates a side view of an embodiment of an apparatus for elevating barbs to a desired angle according to the present invention including a triangle-shaped bending bar and a suture thread.

FIGS. 3A-3F illustrate various embodiments of the bending bars having different configurations. FIG. 3A illustrates an embodiment of a bending bar 204 having the shape of triangle with a base angle beta, β. This particular triangle is an isosceles triangle, but triangles of different shapes can also be used. In this embodiment, the bending bar 204 is positioned about perpendicular to the suture thread 206, the tip 300 of the triangle formed by the sides 302 of the bending bar 204 pointing down toward the suture thread. The tip 212 of a retainer 208 initially contacts the side 302 of the bending bar 204 and can remain in contact with the side 302 of the bending bar 204 until the tip 212 passes the tip 300 of the triangle-shaped bending bar 204 and is finally released. Since the initial point of contact involves the tip 212 of the retainer 208 and a flat side 302 along the bending bar 204, this bending bar configuration can be considered as being relatively non-aggressive as far as plastically deforming the retainer 208. A larger angle beta, β, may cause greater plastic deformation. Additionally, the closer the tip 300 of the bending bar 204 comes to the suture 206 (i.e. height, h, above the suture thread), the more aggressive the bending can become, with more plastic deformation. It is noted that in these embodiments, the suture 206 is moving in direction 350 toward the bending bar 204 with generally the distal portion or the tip portion of the retainer contacting the bending bar initially.

Figure 3B:
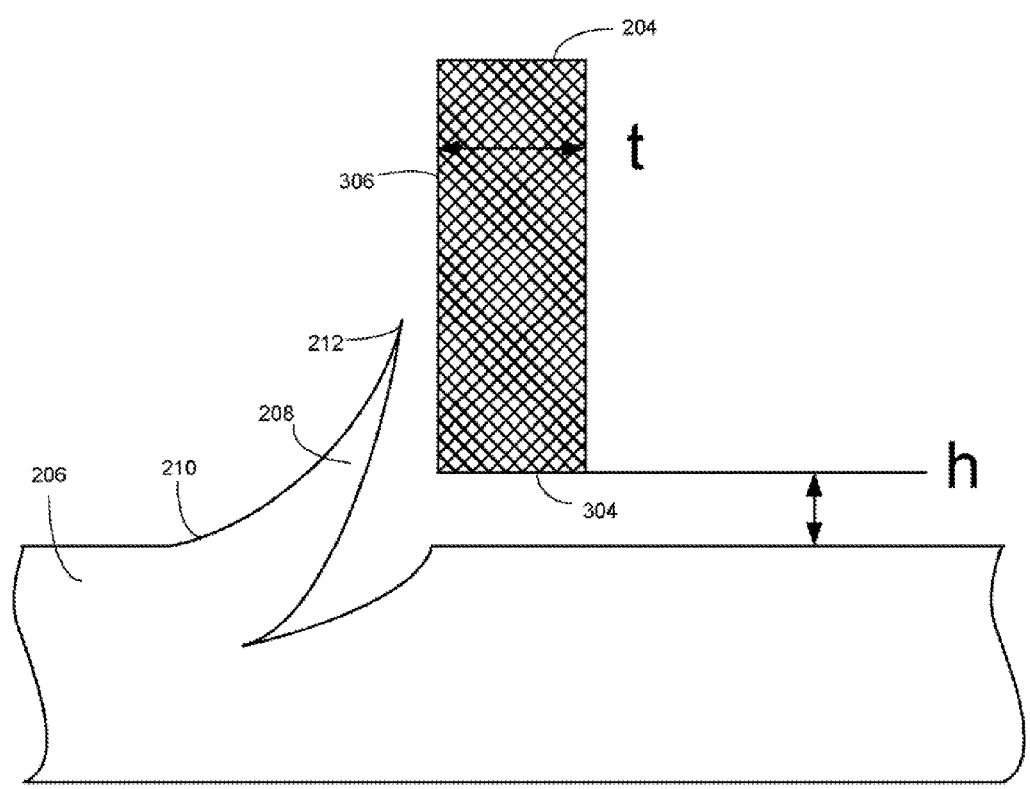
FIG. 3B illustrates a side view of an embodiment of an apparatus for elevating barbs to a desired angle according to the present invention including a rectangle-shaped bending bar and a suture thread.

FIG. 3B illustrates an embodiment of a bending bar 204 having a rectangular shape wherein the bending bar 204 is positioned about perpendicular to the suture thread 206, with the bottom surface 304 of the rectangular-shaped bending bar 204 being about parallel to the suture thread 206. In this embodiment, the tip 212 of a retainer 208 initially contacts the front surface 306 of the bending bar 204. The tip 212 of the retainer 208 can remain in contact with the front surface 306 as well as the bottom surface 304 of the bending bar 204 before the tip 212 is finally released. Since the initial point of contact involves the tip 212 of the retainer 208 and the flat front surface 306 of the bending bar 204, this bending bar 204 configuration can be considered as being relatively non-aggressive. It is noted that this configuration can be slightly more aggressive than the embodiment of the bending bar 204 illustrated in FIG. 3A since the retainer 208 can remain in contact with both the front surface 306 as well as the bottom surface 304 of the bending bar 204, thereby increasing the duration of contact between the bending bar 204 and the retainer 208. Again, the closer the bottom surface 304 comes to the suture 206, the more aggressive the bending can become with more plastic deformation.

Figure 3C:
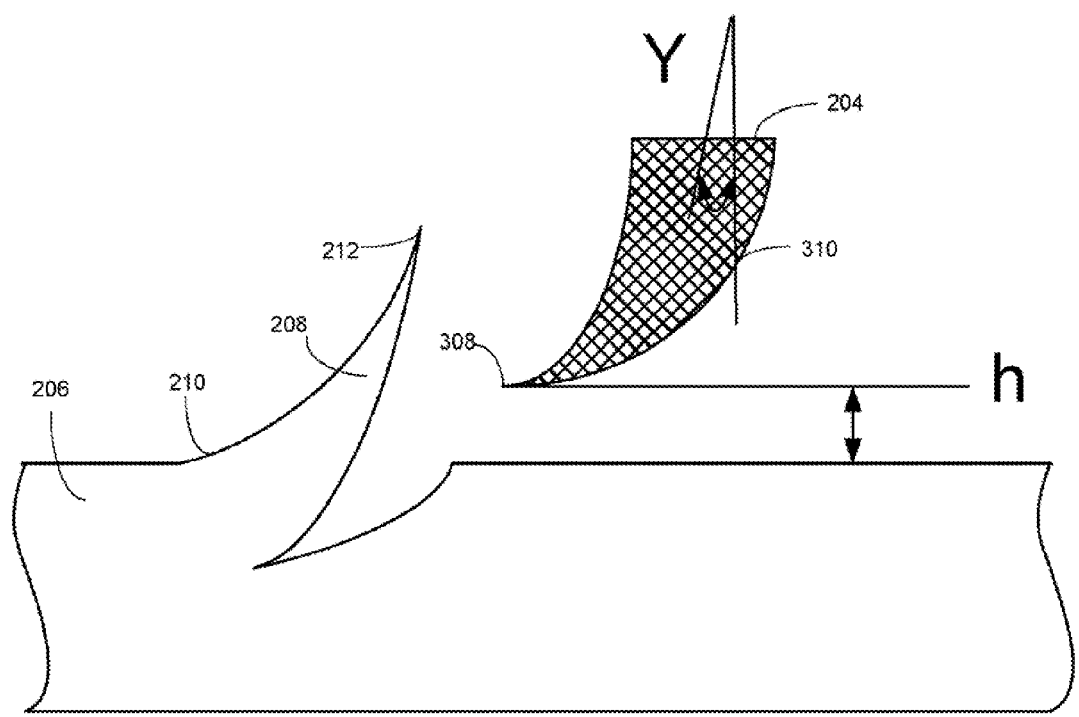
FIG. 3C illustrates a side view of an embodiment of an apparatus for elevating barbs to a desired angle according to the present invention including a horn-shaped bending bar and a suture thread.

FIG. 3C illustrates an embodiment of a bending bar 204 having a tapered horn or J shape. In this embodiment, the tip 308 of the horn-shaped or J-shaped bending bar 204 can be oriented at an angle of attack gamma, γ, to contact the retainer 208 as the suture is passed through the apparatus. As a retainer 208 passes the bending bar 204, the tip 308 of the horn-shaped bending bar 204 initially contacts the retainer 208 adjacent to the base 210 of the retainer 208. The retainer 208 can then remain in contact with the bottom surface 310 of the bending bar 204 before finally being released. A greater angle gamma, γ, may result in a greater plastic deformation. Since the initial point of contact includes a single point which contacts the retainer 208 adjacent to the base 210 of the retainer 208, this bending bar configuration can be considered as being relatively aggressive, resulting in enhanced plastic deformation of the retainer 208. The further away the tip 308 of the bending bar 204 is from the base 210 of the retainer 208 or from the body of the suture thread 206, the less aggressive the process is.

Figure 3D:
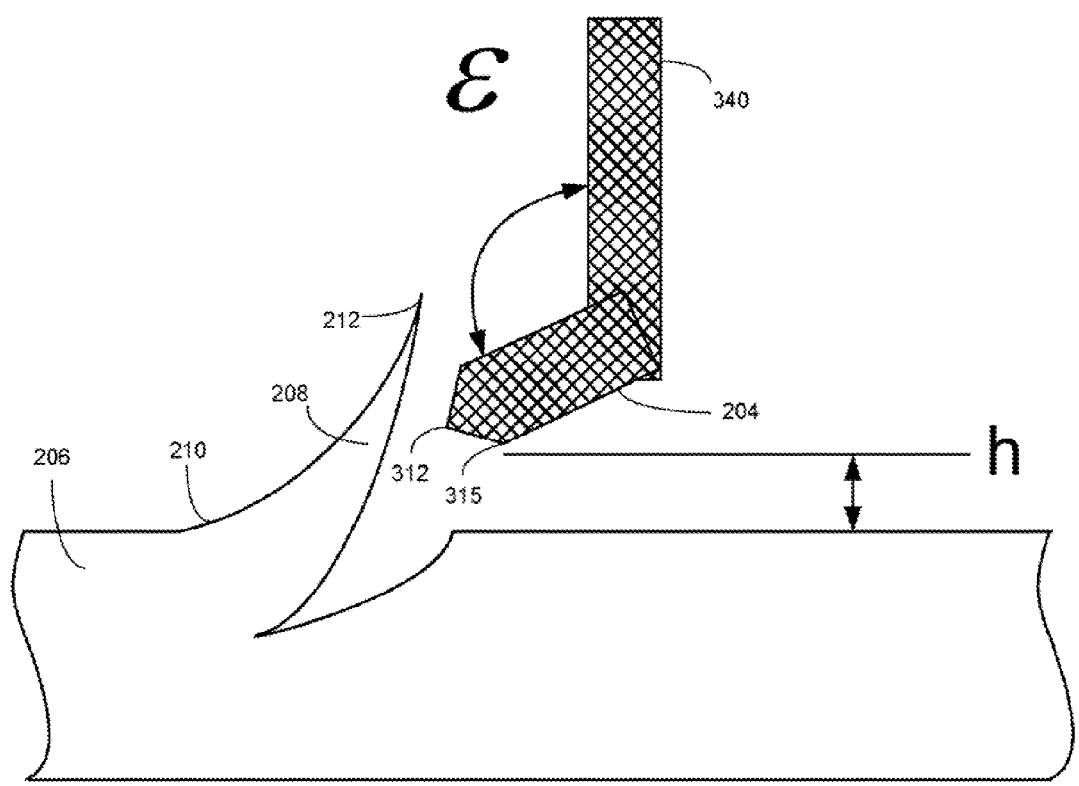
FIG. 3D illustrates a side view of an embodiment of an apparatus for elevating barbs to a desired angle according to the present invention including a pentagon-shaped bending bar and a suture thread.

FIG. 3D illustrates an embodiment of a bending bar 204 having an elongated pentagon shape. In this embodiment, the tip 312 of the pentagon-shaped bending bar 204 can be oriented to contact the retainer 208 as the suture thread 206 is passed through the apparatus 200. As a retainer 208 passes by the bending bar 204, the tip 312 of the pentagon-shaped bending bar 204 initially contacts the retainer 208 adjacent to the base 210 of the retainer 208. The retainer 208 can then remain in contact with the bottom surface 315 of the tip 312 of the bending bar 204 before finally being released. Since the initial point of contact includes a single point which contacts the retainer 208 adjacent to the base 210 of the retainer 208, this bending bar configuration can be considered as being relatively aggressive. Again, a less aggressive process, resulting in less plastic deformation would occur with the tip 312 contacting the retainer 208 further away from the base 210 or further away from the body of the suture thread 206. In FIG. 3D, the bending bar 204 can be movably mounted on mount 340 such that the angle epsilon, ϵ, can be selectively adjusted to vary where and how the tip 312 initially contacts the retainer 208 in order to adjust the amount of bending of the retainer 208.

Figure 3E:
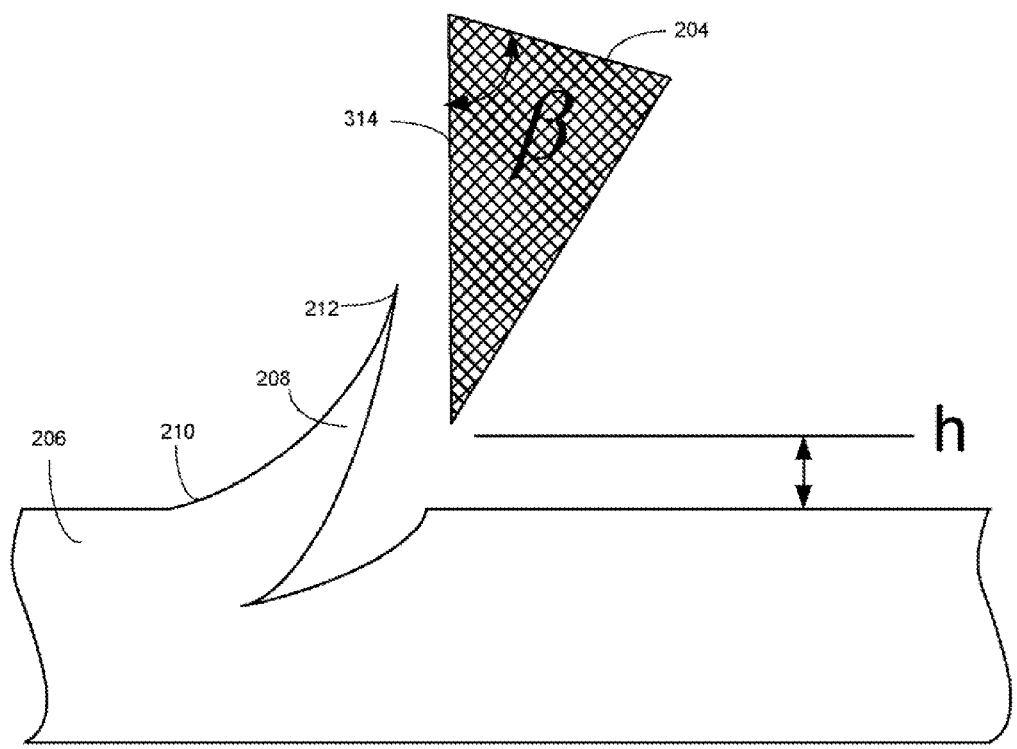
FIG. 3E illustrates a side view of an embodiment of an apparatus for elevating barbs to a desired angle according to the present invention including a triangle-shaped bending bar and a suture thread.

FIG. 3E illustrates an embodiment of a bending bar 204 having the shape of an isosceles triangle similar to the bending bar 204 illustrated in FIG. 3A. In this embodiment, however, the bending bar 204 is angled to allow the front face of the retainer 208 to make flat contact with the front face 314 of the bending bar 204. This configuration can be considered slightly more aggressive than the configuration illustrated in FIG. 3A since the initial point of contact between the bending bar 204 and the retainer 208 is closer to the base 210 of the retainer 208.

Figure 3F:
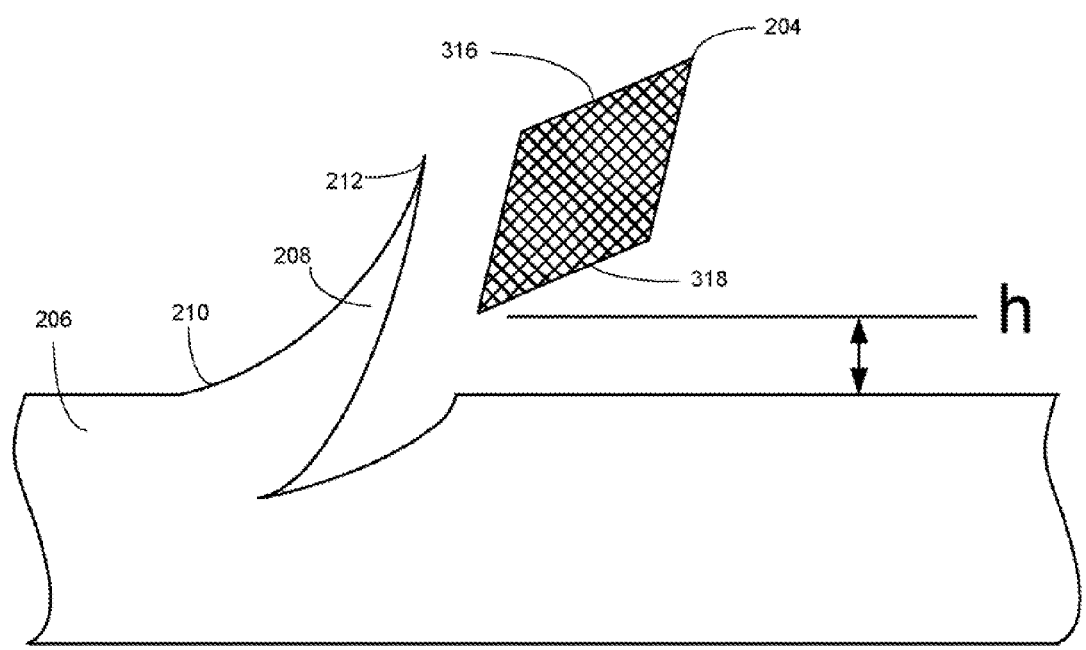
FIG. 3F illustrates a side view of an embodiment of an apparatus for elevating barbs to a desired angle according to the present invention including a rhombus-shaped bending bar and a suture thread.

FIG. 3F illustrates an embodiment of a bending bar 204 having a shape of a rhombus. In this embodiment, similar to the embodiment illustrated in FIG. 3E, the bending bar 204 is angled to allow the front face of the retainer 208 to make flat contact with the front face 316 of the rhombus-shaped bending bar 204. Depending on the size and width of the bending bar 204, the retainer 208 may remain in contact along the front face 316 as well as the bottom face 318 (with the bottom face 318 more parallel to the body of the suture thread 206) of the rhombus-shaped bending bar 204, thereby increasing the duration of contact between the bending bar 204 and the retainer 208, and also increasing plastic deformation of the retainer 208. Generally, in all of these embodiments, the closer the bending bar 204 is to the base of the retainer 208, the more likely that the retainer 208 will be more plastically deformed, as the retainer 208 will be in contact with a bottom face or surface 304, 310, 315, 318 for a longer time due to the fact that the retainer 208 is bent over or back to a greater degree. It is also noted that an increased amount of deformation to the retainer 208 translates to more creep and fatigue over the same time, which can attribute to a decrease in viscoelastic recoil for the retainer 208.

Figure 3G:
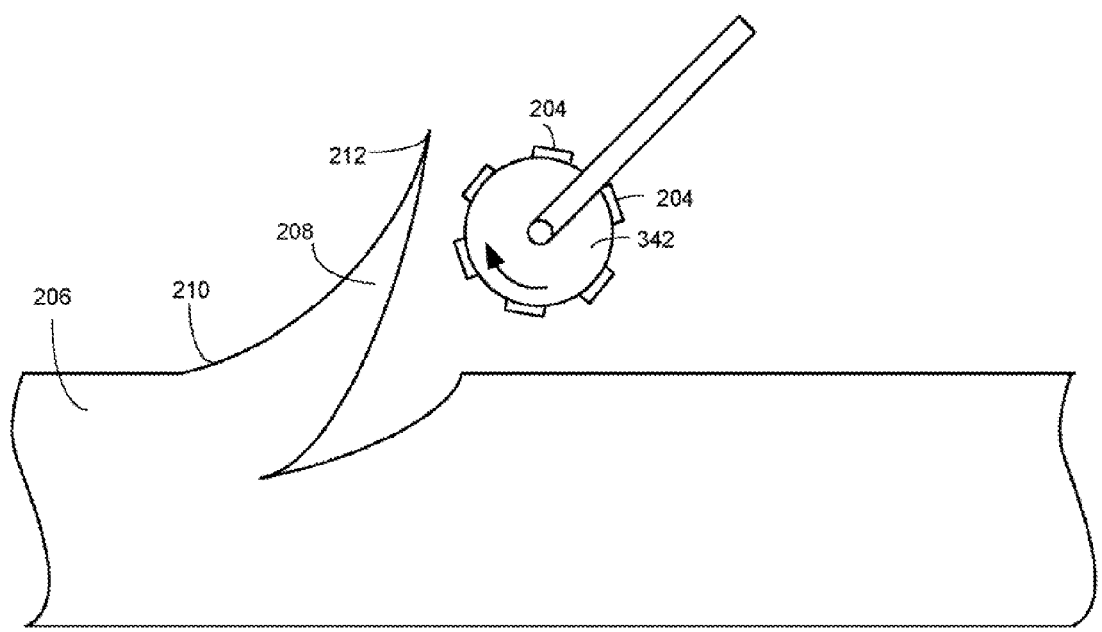
FIG. 3G illustrates a side view of an embodiment of an apparatus for elevating barbs to a desired angle according to the present invention including a plurality of bending bars mounted on a rotatable wheel and a suture thread.

FIG. 3G illustrates yet another embodiment of the bending bar system. In this embodiment, a plurality of rectangular shaped bending bars 204 (as shown in FIG. 3B) are mounted on a rotatable wheel 342, which can be used to deform the retainer 208. As the wheel 342 rotates in direction 344, a plurality of individual bending bars 204 can contact the retainer 208, thereby increasing the deformation of the retainer 208. It is noted that the speed of rotation for the wheel 342 can be increased to increase the aggressiveness of the retainer 208 bending process. As with the embodiments set forth above, the location of initial contact between the bending bars 204 and the retainer 208 can also be varied to affect the aggressiveness of the retainer 208 bending process. Bending bars, as shown in the other embodiments, can also be used in this embodiment.

It is to be understood that the bending bar 204 used within the apparatus 200 can have any shape, any thickness, and/or contact the retainers 208 at any angle and still fall within the scope of this invention. It is also to be understood that regardless of the geometry of the bending bar 204, the aggressiveness of the bending bar 204 configuration can be significantly affected by adjusting the height of the bending bar 204 relative to the suture thread 206 and the amount of time the bending bar 204 is in contact with the retainer 208. A bending bar 204 set at a height that only contacts a retainer 208 at the tip 212 of the retainer 208 will be significantly less aggressive, and thereby result in less plastic deformation, than a bending bar 204 set at a height that contacts a retainer 208 adjacent to the base 210 of the retainer 208. It is further noted that bending bars 204 having different heights and/or geometries can be used in sequence to affect the retainers 208 in a desired manner. In an embodiment, a plurality of bending bars 204 can be configured around a single roller 202 as shown in FIG. 2A.

Referring again to FIG. 2A, the rollers 202 of the apparatus 200 can be varied and/or altered and yet still accomplish the purpose of the invention. In an embodiment, as set forth above, any combination of one or more rollers 202 can be used within the apparatus 200. In an embodiment, rollers 202 having other diameters, including the same or different diameters with respect to the other rollers 202, may be used. The diameter of the rollers 202 can control the extent with which the retainers 208 protrude from the back of the suture thread 206 as the retainers 208 pass by the bending bars 204. Accordingly, smaller diameter rollers 202 will cause the retainers 208 to elevate to a greater extent than larger diameter rollers 202. In another embodiment, the rollers 202 used in a series within the apparatus 200 may have identical or differing diameters. In another embodiment, the rollers 202 may include a grooves or channels to help keep the suture thread 206 in place during the bending process. In yet another embodiment, the rollers 202 may be configured to have a stationary configuration.

In an embodiment, the temperature used during the bending process within the apparatus may also be varied. It is noted that material fatigue, creep, and/or shape memorization is more severe in objects which are subjected to heat. Accordingly, the operating temperature of the bending process can be elevated to facilitate plastic deformation of the retainers. During the process, the operating temperature can be elevated to near or above the crystallization temperature of the suture polymer, but below the melting point of the polymer of the suture. The temperature of the bending process may also be affected by elevating the temperature of the entire apparatus, the bending bars 204 and/or the rollers 202 during the bending process. With elevated temperatures and a longer retainer bending time, as provided by the more aggressive bending bar configurations described above, more retainer annealing can occur with more plastic deformation resulting.

It is noted that to anneal a polymer, the polymer is heated to a temperature above a crystallization temperature for an amount of time to change its microstructure, and then cooled at a given rate to retain or obtain a different microstructure. For example, the crystallization temperature for polydioxanone is about 40° C., while a crystallization temperature for a copolymer of glycolide $\epsilon$-caprolactone in a 72/28 ratio is about 75° C. Sutures are typically formed from extruded polymer and are annealed after extrusion to relieve some of the alignment of polymer chains, to recover some elongation, and to drive out residual solvents. The sutures can subsequently be heated over a period of time to sterilize the sutures. Some annealing can occur during sterilization; although where sutures are sterilized using techniques employing relatively low temperatures (such as sterilization by ethylene oxide) the annealing is typically not effective in reducing internal stresses. The semi-crystalline structure that results from processing provides a suture with mixed properties including high yield strength and acceptable malleability.

Annealing of a retainer can achieved by local heating of the retainer at the base of the retainer while the retainer is protruding to a generally desired degree. Local heating of the retainer can be achieved by elevating the temperature of the entire apparatus 200, the bending bars 204 and/or the rollers 202 during the bending process. It is proposed that bending a retainer 208 at a sufficient temperature (e.g., 200° C.) for 4-5 milliseconds, and then cooling by ambient temperature, can be used to help permanently affect the retainer 208. Alternatively, the retainer 208 can be actively cooled to a temperature below the ambient temperature. For example, cooling can be accomplished using a Peltier device, which is a device for electrically controlling temperature that can be miniaturized to suit small features.

Generally, as described herein and depicted in the Figures, the amount of bending of the retainer and the plastic deformation can be affected by:
1. a triangular bending bar with a pointed tip with a base angle beta, $\beta$, as a variable,
2. a flat bending bar with a thickness t, as a variable,
3. a semicircular bending bar with an angle of attack gamma, $\gamma$, as a variable,
4. a tipped bending bar with an angle or orientation of the tip epsilon, $\epsilon$, as a variable,
5. an angled version of the triangular bending bar,
6. a rhombi bending bar shape and other shapes of the bending bar,
7. a number of bending bars greater than one,
8. the position of the bending bars around the rollers,
9. the number of rollers,
10. the temperature during the process (preferably, near or above the crystallization temperature of the polymer or it may also be below that for cold drawing of the polymer, and not above the onset of melting),
11. the temperature of the retainer after the process (e.g., cooling the retainer by blowing cold air onto the retainer after it has been heated within the apparatus),
12. the temperature of the bending bars, 13. the temperature of the rollers,
14. the speed with which the self-retaining suture is pulled through the rollers,
15. the angle α as a variable,
16. the height (h) between the suture and the tip of the bending bar,
17. the radius of the roller,
18. the flexibility of the bending bar, and
19. quenching by blowing cold air on the last set of retainers so that the retainers keep their shape.

The bending bar 204 can be made to withdraw with a frequency such that the stress in the retainer 208 is optimized (effectively changing the height) during the passing of the retainer relative the tip of the bending bar 204. For example, the bending bar 204 can be withdrawn (effectively increasing the height) as the retainer 208 approaches an undesirable angle (bending backwards, for example) to alleviate damage to the retainer.

Rollers 202 of increasing or decreasing diameter, bending bars 204 of decreasing height, geometry, or flexibility, and/or altering the temperature of the rollers 202 may all be used and/or varied in sequence.

The bending bars 204 may also be moved back and forth along the suture to create an even greater force on the retainers 208.

Figure 2B:
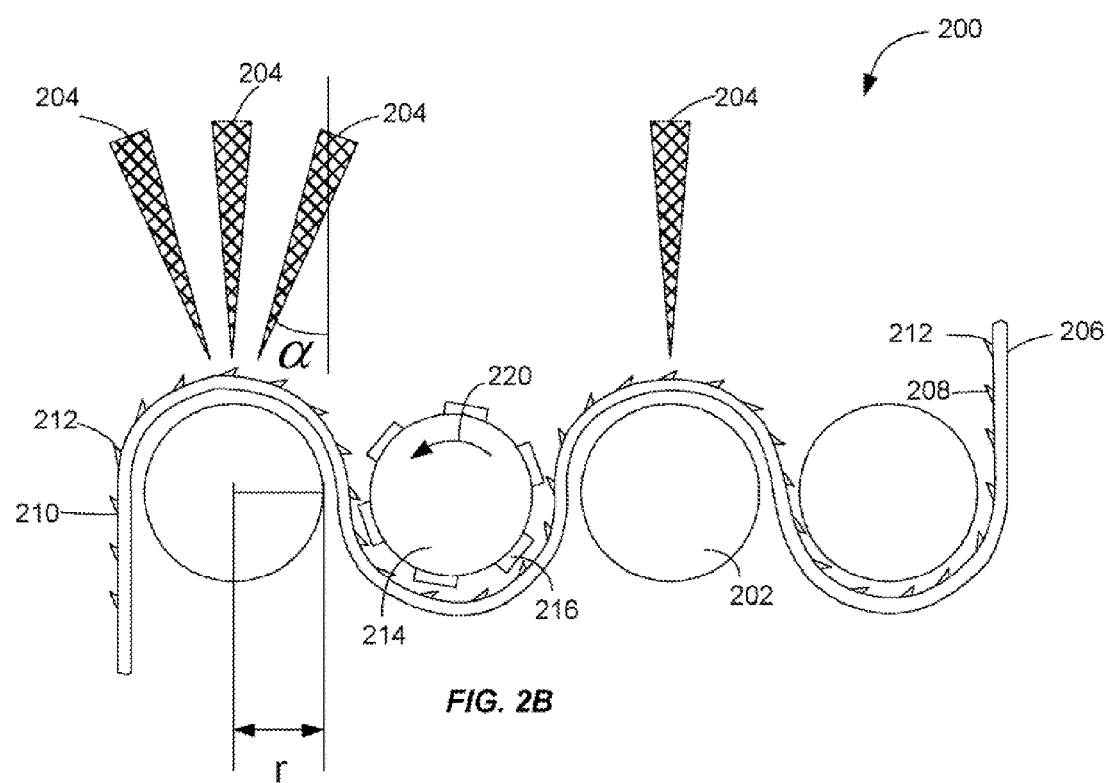
FIG. 2B illustrates a side view of an embodiment of an apparatus for elevating barbs to a desired angle according to the present invention including rollers and bending bars and intermediate rollers having cogs.

Referring now to FIG. 2B, another embodiment of an apparatus 200 for elevating retainers to a desired angle of the present invention is illustrated. As with the embodiment of the invention shown in FIG. 2A, this embodiment of the invention also includes a suture thread 206 that is passed through a series of rollers 202, 214 while bending bars 204 are used to apply a mechanical force to the retainers 208 of the suture thread 206 to deform the retainers 208. In this embodiment, however, the intermediate rollers 214, which act as pivot points within the apparatus 200, include cogs 216 that can be used to accept and bend the retainers 208 on the suture thread 206 as the suture thread 206 is pulled through the apparatus 200. In an embodiment, the intermediate rollers 214 do not rotate. In this configuration, as the suture thread 206 is pulled through the apparatus 200 in direction 218, the retainers 208 are bent back by the cogs 216 on the intermediate rollers 214. In another embodiment, the intermediate rollers 214 are allowed to rotate in direction 220 within the apparatus 200. In this configuration, the retainers 208 can catch or snag on the cogs 216, thereby causing the intermediate rollers 214 to rotate in direction 220 as the suture thread 206 is pulled through the apparatus 200. The intermediate rollers 214 can also resist rotation in varying degrees, which can affect the amount of force placed on the retainers 208 by the cogs 216 of the intermediate rollers 214. Accordingly, a greater amount of force can be placed on the retainers 208 by increasing the resistance to rotation by the intermediate rollers 214. In another embodiment, the intermediate rollers with the cogs can rotate in synchronization with the other roller so that the retainers are located between the cogs to prevent the intermediate rollers from flattening the retainers. In an embodiment, the intermediate rollers 214 can also be mechanically rotated in a direction converse to the direction that the suture thread 206 is being pulled (direction 222 in FIG. 2B) to create an even greater force on the retainers 208 by increasing the amount of contact between the retainers 208 and the cogs 216.

Figure 2C:
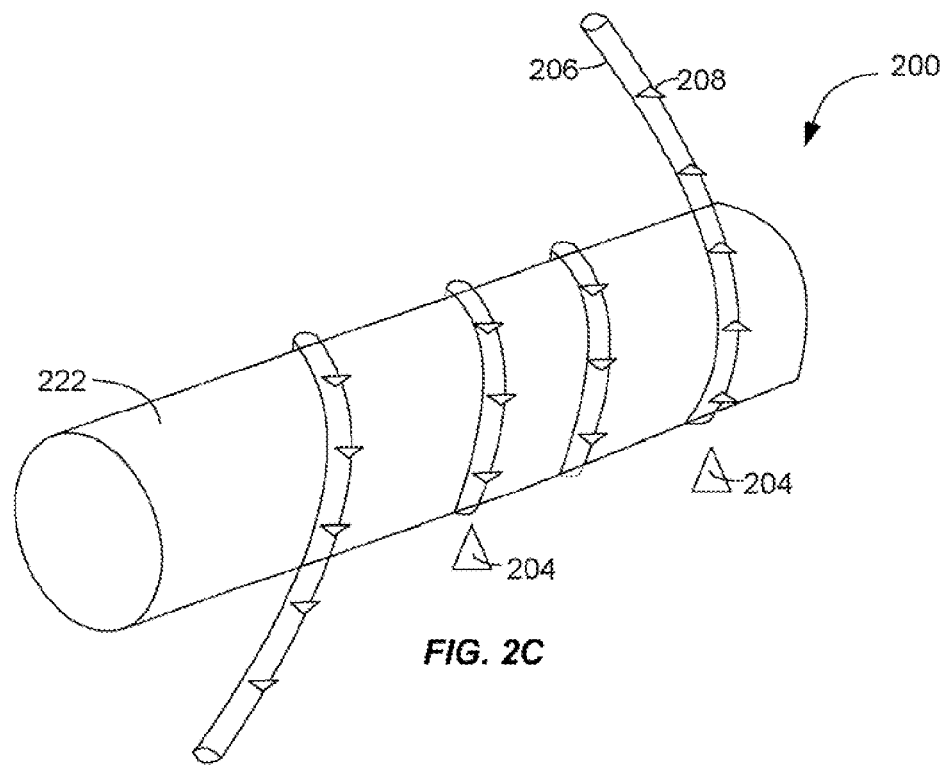
FIG. 2C illustrates a perspective view of an embodiment of an apparatus for elevating barbs to a desired angle according to the present invention including a cylindrical roller having a suture thread wrapped around it and bending bars.
Figure 2D:
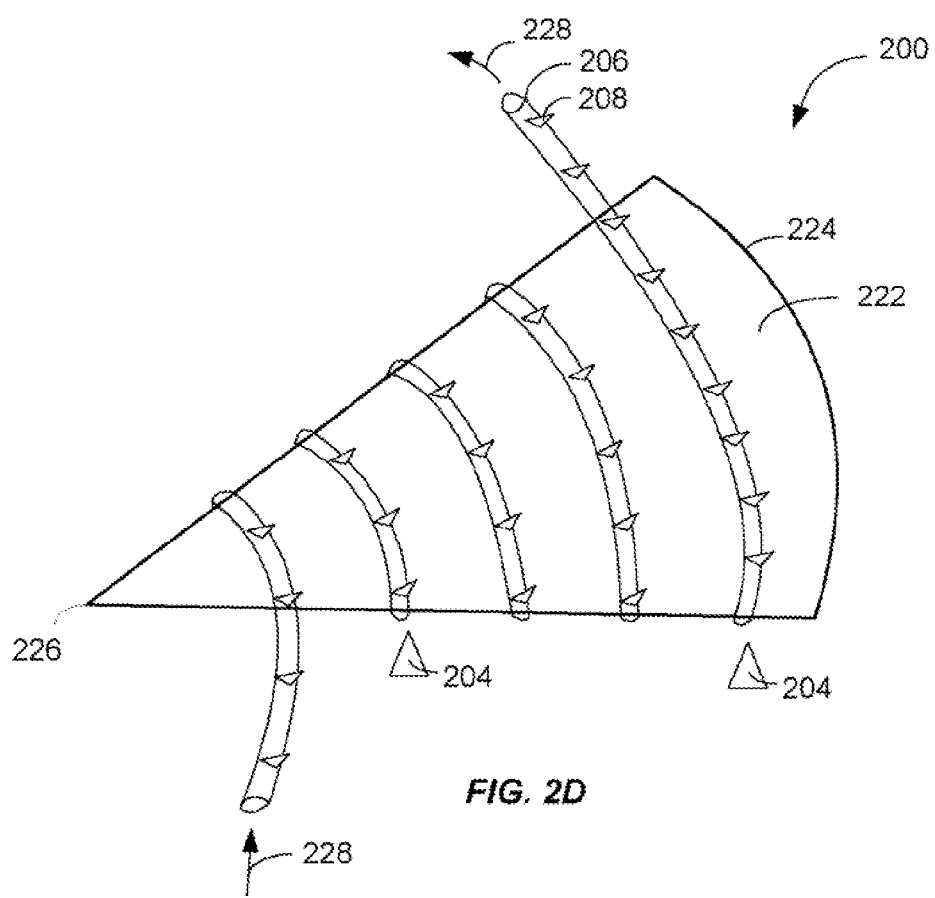
FIG. 2D illustrates a perspective view of an embodiment of an apparatus for elevating barbs to a desired angle according to the present invention including a cone-shaped roller having a suture thread wrapped around it and bending bars.

Referring now to FIG. 2C, yet another embodiment of an apparatus 200 for elevating retainers to a desired angle of the present invention is illustrated. In this embodiment, a suture thread 206 having retainers 208 is wrapped around a single cylindrical roller or tube 222 in a helical pattern, wherein one or more bending bars 204 can be placed around the periphery of the tube 222 to apply a force to the retainers 208. The suture thread 206 of this embodiment is maintained in a twisted configuration (which can correspond to the configuration of the suture thread 206 as it leaves a retainer-forming machine) to allow all of the retainers 208 to face away from the tube 222 and toward the bending bars 204. In an embodiment, the tube 222 can include a groove or channel that spirals along the surface of the tube 222 for accepting the suture thread 206 in order to keep the suture thread 206 in place during the bending process. It is noted that the bending bars 204 of this embodiment can include any shape or configuration as set forth in the Figures and described above. The diameter of the tube can be varied to control the extent with which the retainers 208 protrude from the back of the suture thread 206 as the retainers 208 pass by the bending bars 204. Accordingly, a tube 222 with a smaller diameter will cause the retainers 208 to elevate to a greater extent than a tube 222 having a larger diameter. In an embodiment, the diameter of the tube 222 can be varied to affect the bending characteristics of the apparatus 200 along the tube 222. For example, as shown in FIG. 2D, the tube 222 can be cone-shaped wherein the diameter of the tube 222 is greater on the first end 224 than the second end 226. Accordingly, for a suture thread 206 being pulled in direction 228, the retainers 208 can initially be elevated to a greater extent near the second end 226 of the tube 222 than the first end 224 of the tube 222 depending on the characteristics of the particular retainers 208 being deformed. Other characteristics of the apparatus 200 can also be changed consistent with the disclosures set forth above (e.g., the operating temperature, the proximity of the bending bar 204 to the suture thread 206 during the bending process, the bending bar 204 shapes, etc.) without deviation from the scope of this invention.

Figure 4:
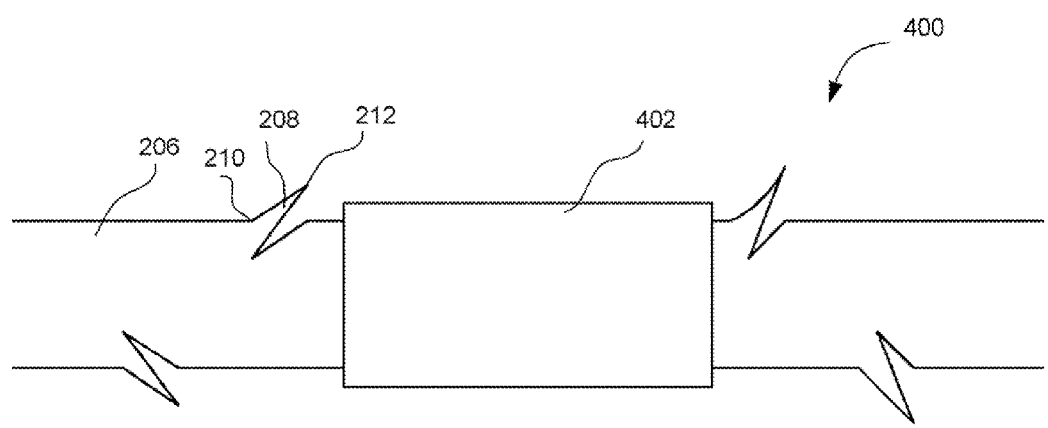
FIG. 4 illustrates a side view of an embodiment of an apparatus for elevating barbs to a desired angle according to the present invention including a hollow tube.

Referring now to FIG. 4, an alternative apparatus for elevating retainers to a desired angle, generally numbered 400, of the present invention is illustrated. In this embodiment of the invention, instead of using a series of bars and rollers to bend the retainers 208, a hollow tube 402 having an inner diameter slightly larger than the diameter of the suture thread, and slightly smaller than the outermost protrusion of the retainers 208 to catch the retainers 208, can be used to bend the retainers 208. Accordingly, as the suture thread 206 is fed into the tube 402, the retainers 208 can contact the inner surface of the tube 402, thereby being bent back within the tube 402. As the retainers 208 emerge from the tube 402, the retainers 208 will have an elevated configuration. As with the apparatus 200 illustrated in FIG. 2A, the embodiment of the apparatus 400 shown in FIG. 4 can be used after the retainers 208 have been cut and/or otherwise created by a retainer-forming machine. The suture thread 206 can be in a twisted configuration or untwisted configuration as it passes through the hollow tube 402.

In an embodiment, the diameter of the inner surface of the tube 402 can be adjusted to affect the aggressiveness of the bending process within the tube 402. The aggressiveness of the bending process can be increased by reducing the inner diameter of the tube 402, thereby causing the inner surface of the tube 402 to contact the retainers 208 at a location closer to the base 210 of the retainers 208. In another embodiment, the speed with which the suture thread 206 is pulled through the tube 402 can be decreased, thereby increasing the duration of contact between the retainers 208 and the tube 402. In yet another embodiment, the temperature of the tube 402 and/or within the tube 402 can be elevated to promote creep and fatigue as set forth above.

Figure 5:
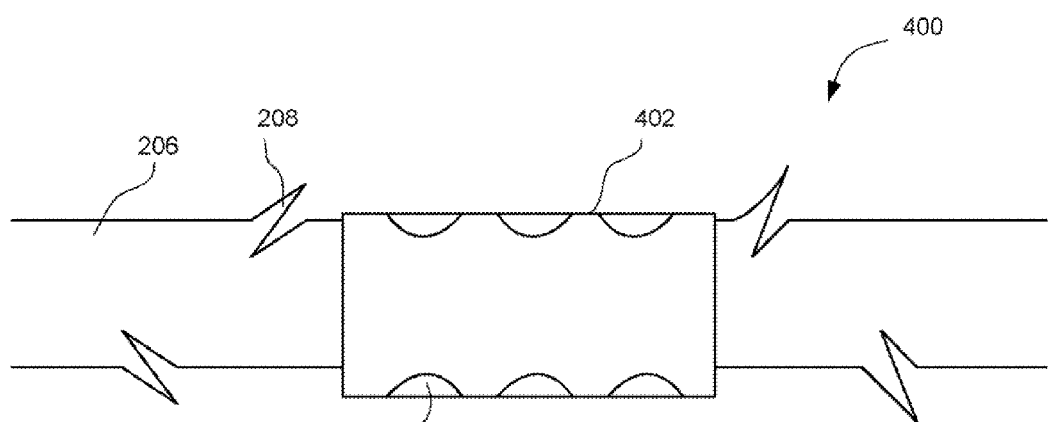
FIG. 5 illustrates a sectional view of an embodiment of an apparatus for elevating barbs to a desired angle according to the present invention including a hollow tube with dimples.

FIG. 5 illustrates a sectional view of another embodiment of the tube 402. In this embodiment, the inner surface of the tube 402 includes round dimples 404 to contact the retainers 208 as the suture thread 206 moves through the tube 402. The dimples 404 facilitate the bending of the retainers 208 within the tube 402. In another embodiment of this invention, the inner surface of the tube 402 may include grooves or bars or projections having any other shape and may include objects resembling the bending bars 204 illustrated in FIGS. 3A-3F. In an embodiment, the size of the dimples 404 or bar or grooves or projections within the tube 402 can be varied.

Figure 6:
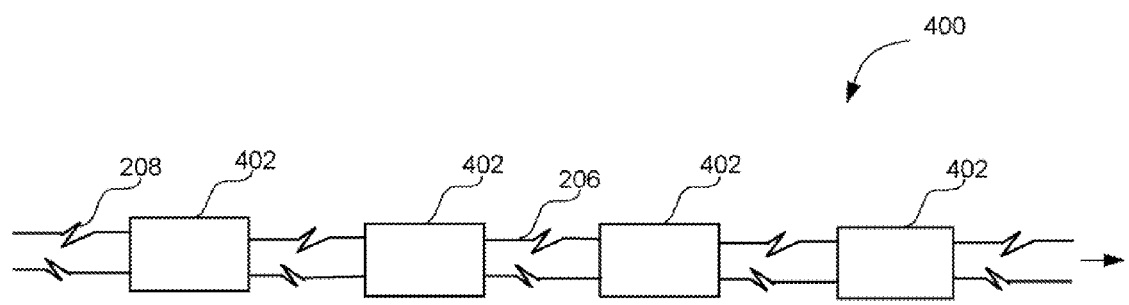
FIG. 6 illustrates a side view of an embodiment of an apparatus for elevating barbs to a desired angle according to the present invention including a plurality of hollow tubes in a series.

FIG. 6 illustrates another embodiment of the apparatus 400. In this embodiment, the suture thread 206 is fed into a series of tubes 402, as opposed to a single tube 402, to bend the retainers 208. It is noted that any number of tubes 402 may be used and still fall within the scope of this invention.

Figure 7:
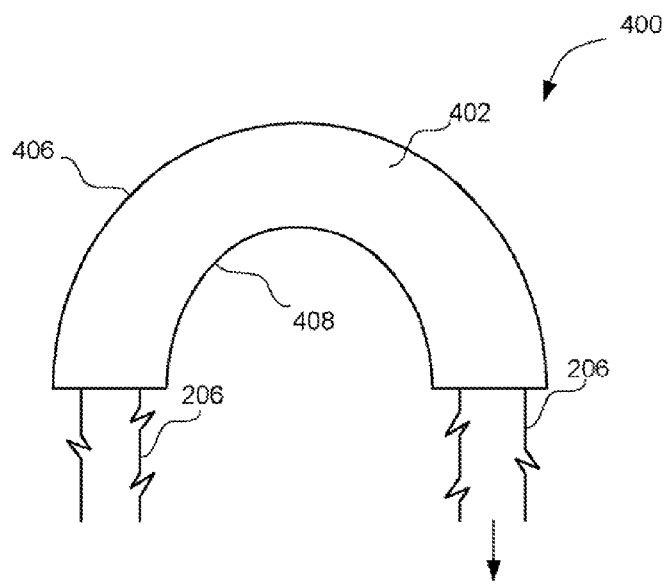
FIG. 7 illustrates a side view of an embodiment of an apparatus for elevating barbs to a desired angle according to the present invention including a U-shaped hollow tube.
Figure 8:
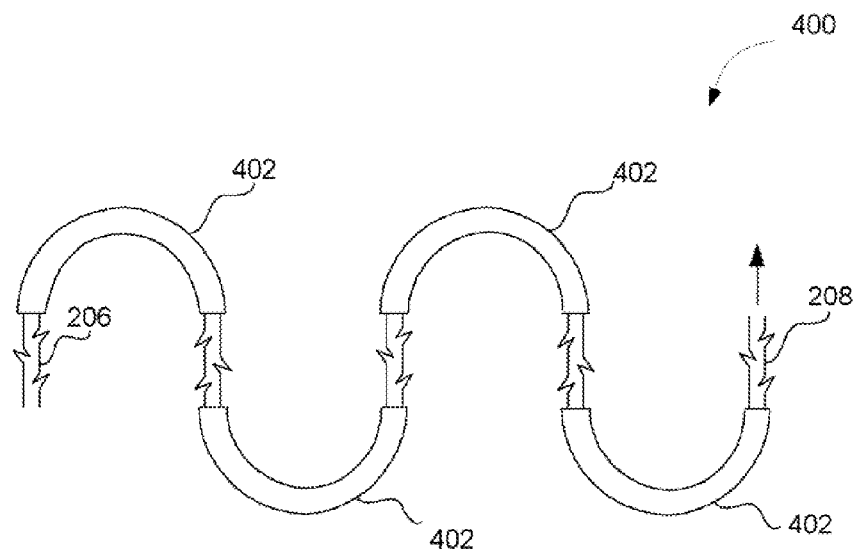
FIG. 8 illustrates a side view of an embodiment of an apparatus for elevating barbs to a desired angle according to the present invention including a series of U-shaped hollow tubes in a series.

FIG. 7 illustrates another embodiment of the tube 402. In this embodiment, the tube 402 includes a bent configuration. In this configuration, the suture thread 206 is bent going through the tube 402 to allow the retainers 208 to elevate from the suture thread 206 within the tube. In an embodiment, the suture thread 206 can be in a twisted configuration as the suture thread 206 passes through the tube 402 whereby all of the retainers 208 are positioned to be adjacent to the top surface 406 of the tube 402 and the portion of the suture thread 206 opposing the retainers 208 is located adjacent to the bottom surface 408 of the tube 402. In another embodiment, the apparatus 400 can include a series of tubes 402 having a bent configuration as shown in FIG. 8. In yet another embodiment, a single tube 402 being bent in multiple different locations can be used to elevate the retainers 208 from the suture thread 206.

Figure 9:
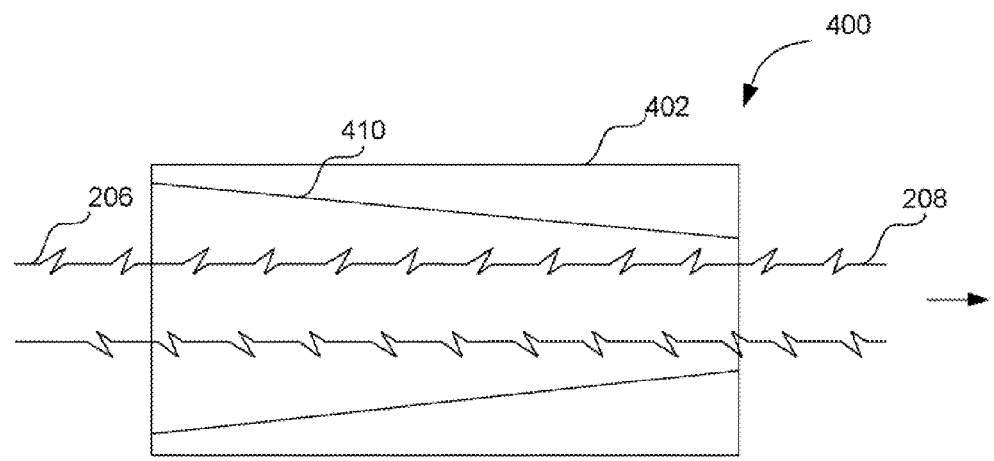
FIG. 9 illustrates a sectional view of the inner surface of a hollow tube for elevating barbs to a desired angle according to the present invention.

FIG. 9 illustrates a sectional view of another embodiment of the tube 402. In this embodiment, the diameter of the inner surface 410 of the tube 402 varies within the tube 402. In the embodiment illustrated in FIG. 9, the inner surface 410 of the tube 402 gradually narrows, thereby allowing the retainers 208 to gradually be bent back by the tube 402. It is to be understood that the inner surface 410 can have multiple diameters within the tube 402 and still fall within the scope of this invention.

Referring now to FIGS. 10A-10F, an alternative apparatus for elevating retainers to a desired angle, generally numbered 500, of the present invention is illustrated. In this embodiment, a ring 502 having a first half 504 and a second half 506 is used to bend the retainers 208 on the suture thread 206, the suture thread having a first end 508 and a second end 510. As with the hollow tube 402 shown in FIG. 4 and described above, the ring has an inner diameter which is slightly larger than the diameter of the suture thread and slightly smaller than the outermost protrusion of the retainers 208. The first half 504 of the ring 502 is attached to a first mechanical arm 512 and the second half 506 of the ring 502 is attached to a second mechanical arm 514, wherein the mechanical arms 512, 514 can move the ring 502 back and forth along the suture thread 206 to bend the retainers 208.

Figure 10A:
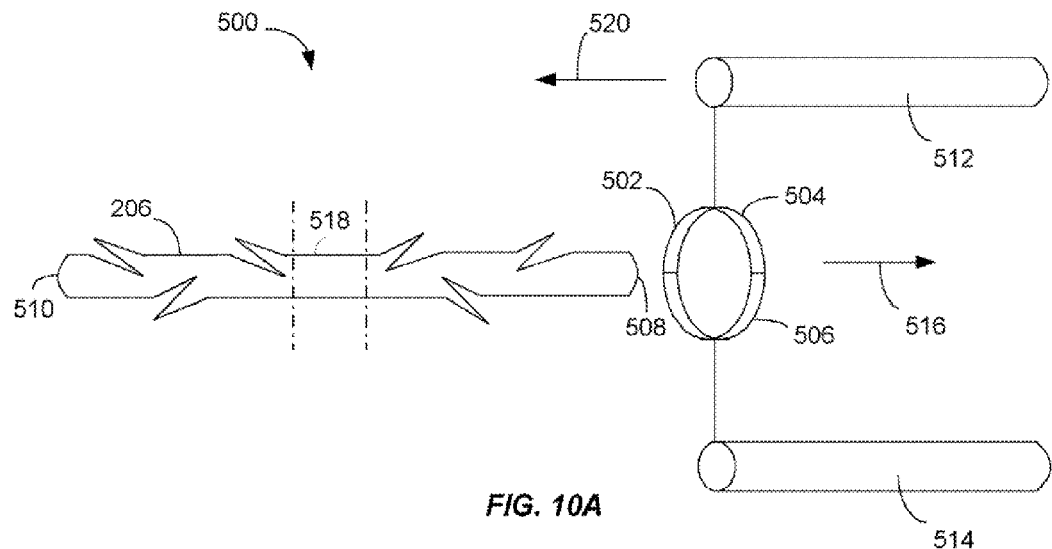
FIGS. 10A-10F illustrate a side view of an embodiment of the apparatus for elevating barbs to a desired angle according to the present invention.
Figure 10B:
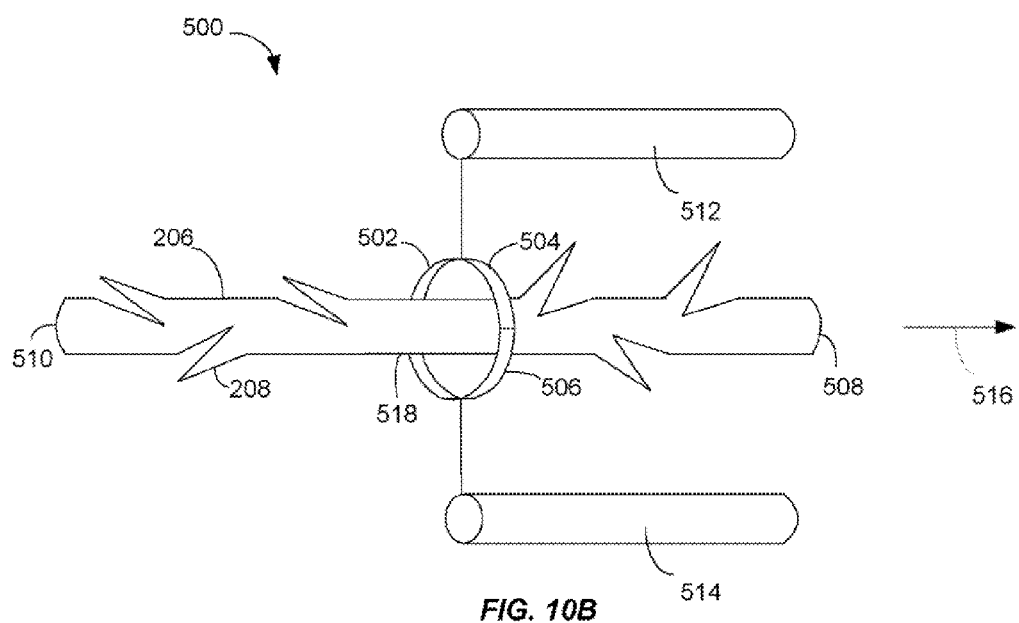
Figure 10C:
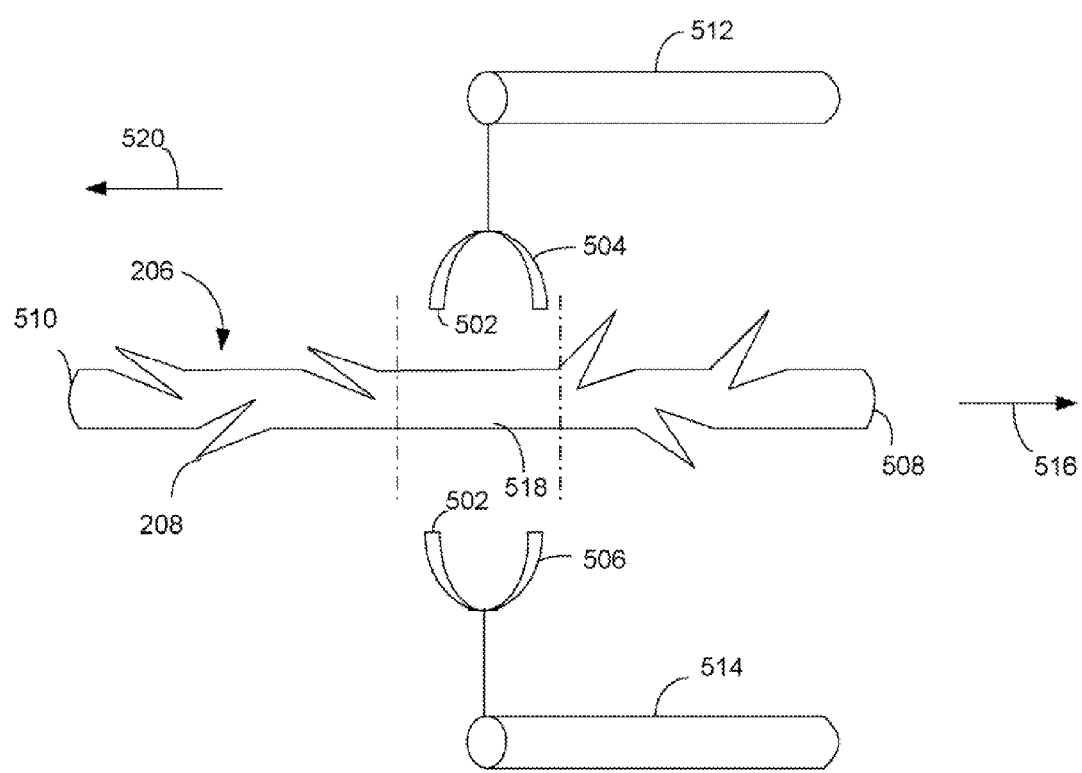
Figure 10D:
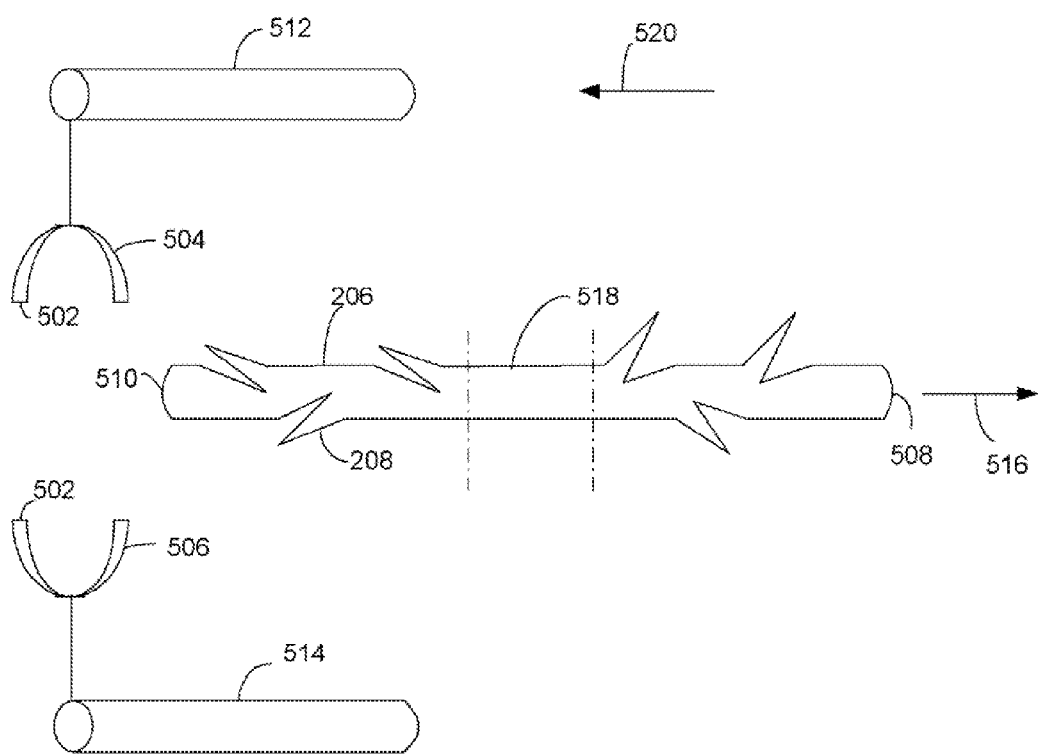
Figure 10E:
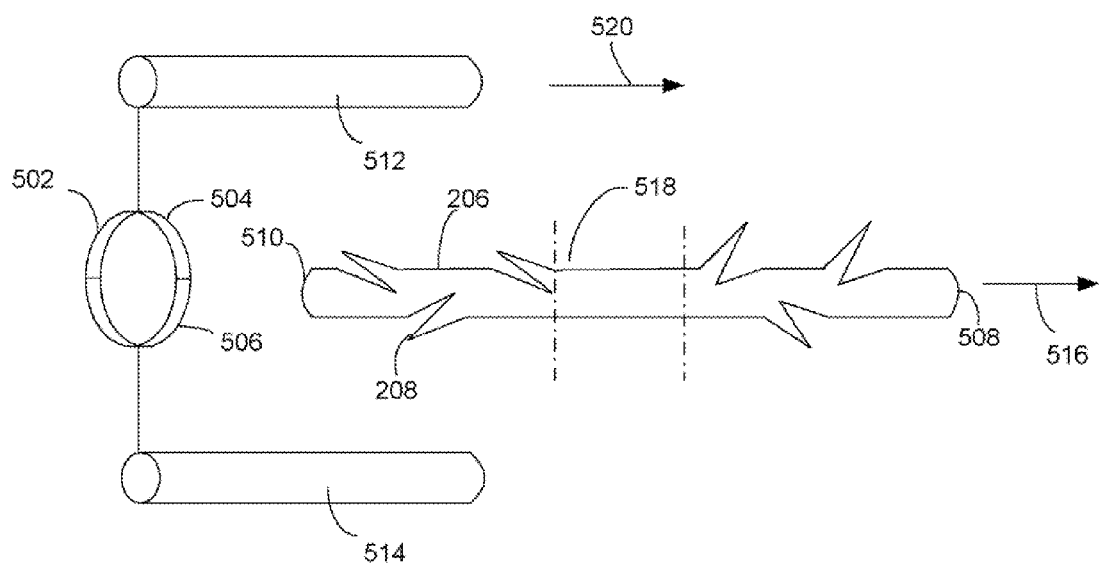
Figure 10F:
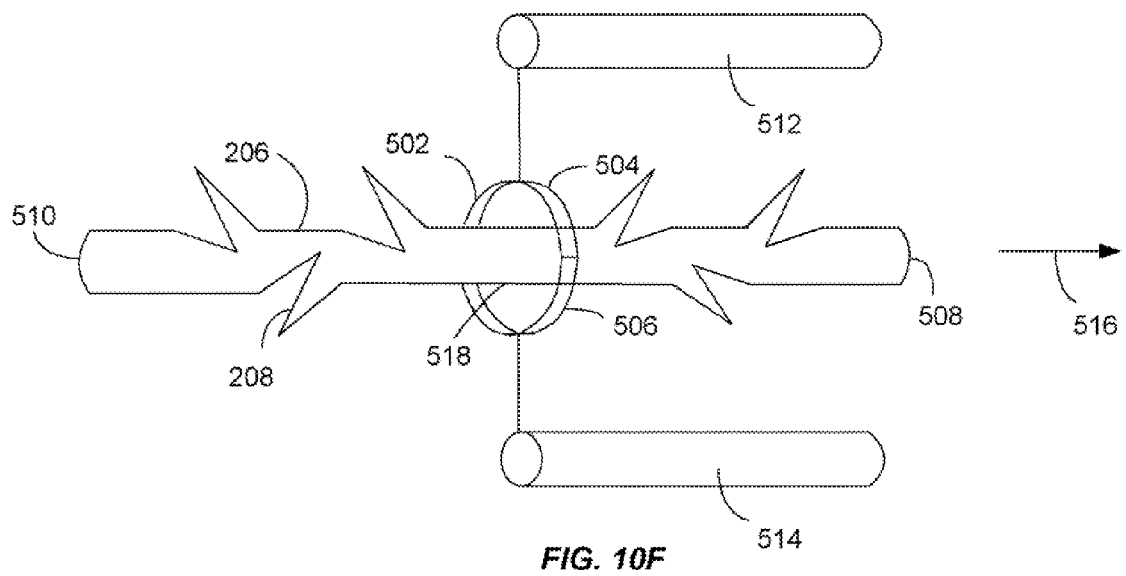

In this embodiment, the ring 502 is initially placed proximal to the first end 508 of the suture thread 206 wherein all of the retainers 208 are facing in direction 516. Once the ring 502 has been placed, the suture thread 206 is moved through the ring 502 in direction 516 to bend the retainers 208 back and away from direction 516. The two halves 504, 506 of the ring 502 are kept together until the ring 502 reaches the transition segment 518 of the suture thread 206 as shown in FIG. 10B. Once the ring 502 reaches the transition segment 518, the mechanical arms 512, 514 separate the two halves 504, 506 of the ring 502 to disengage the ring 502 from the suture thread 206 as shown in FIG. 10C. The mechanical arms 512, 514 then move both halves 504, 506 of the ring 502 in direction 520 to a location proximal to the second end 510 of the suture thread 206 as shown in FIG. 10D. The two halves 504, 506 of the ring 502 are then brought back together as shown in FIG. 10E. Once both halves 504, 506 of the ring 502 are brought back together, the mechanical arms 512, 514 move the ring 502 in direction 516 at least twice as fast as the suture thread 206 is being pulled through apparatus 500, also in direction 516. This action bends the retainers back and in the direction 516. Once the ring 502 reaches the transition segment 518 once again, the arms 512, 514 separate the two halves 504, 506 of the ring 502 to allow the entire suture thread 206 to pass by the ring 502. The process can then be repeated for another suture. In an embodiment, apparatus 500 can be used to elevate retainers 208 before and/or after the retainers 208 have been elevated by another embodiment of the invention shown in FIGS. 2A-9 and/or described herein. It is to be understood that the operating speed of the mechanical arms 512, 514 can be further varied without deviation from the scope of this invention.

Figure 11:
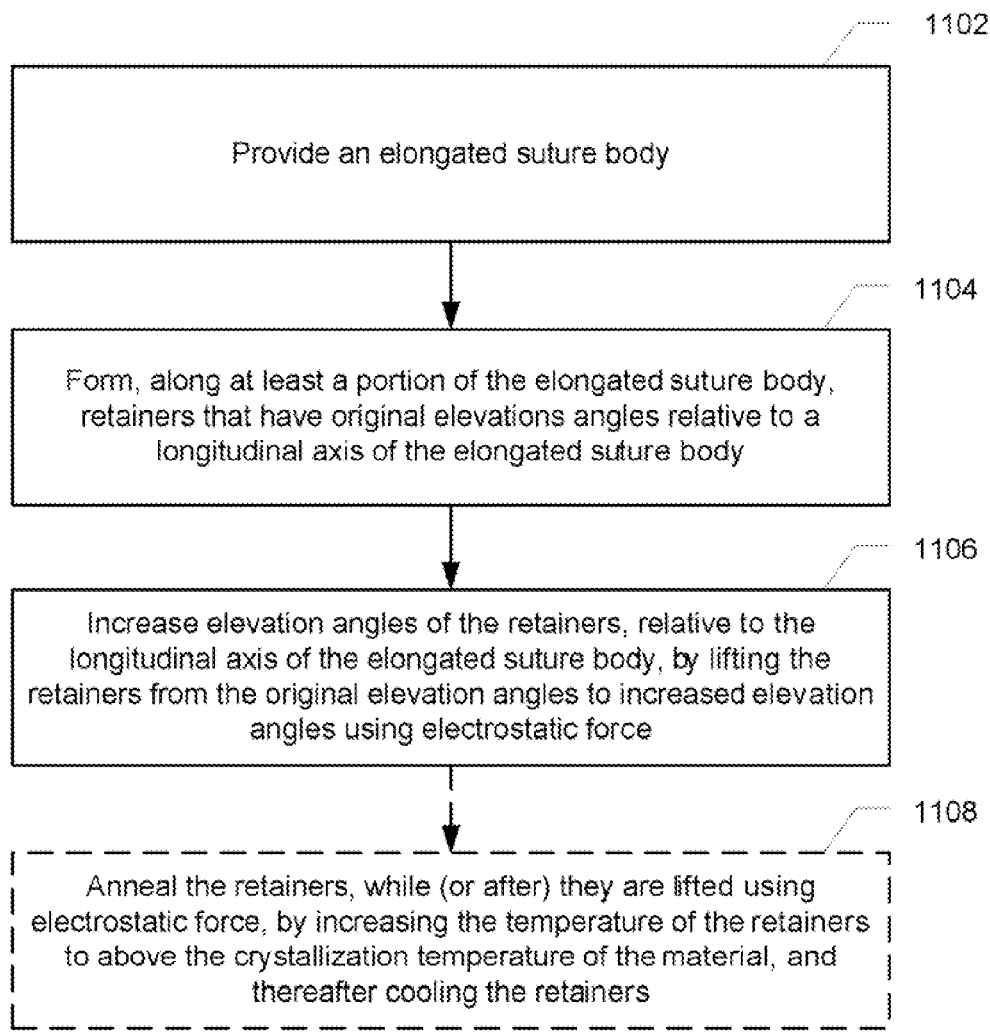
FIG. 11 is a high level flow diagram that is used to summarize methods of forming self-retaining sutures in accordance with embodiments of the present invention.

FIGS. 11 to 14:

FIG. 11 is a high level flow diagram that is used to summarize methods of forming a self-retaining suture in accordance with embodiments of the present invention. Referring to FIG. 11, at step 1102, an elongated suture body is provided. The elongated suture body can also be referred to as a suture thread, details of which are provided above.

Figure 12A:
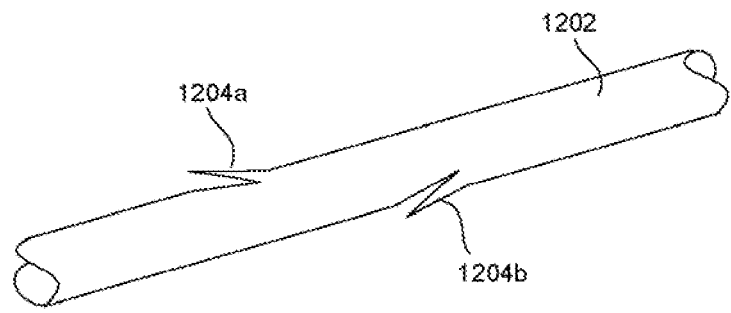
FIG. 12A is perspective view of a portion of an elongated suture body having retainers cut into the suture body.
Figure 12B:
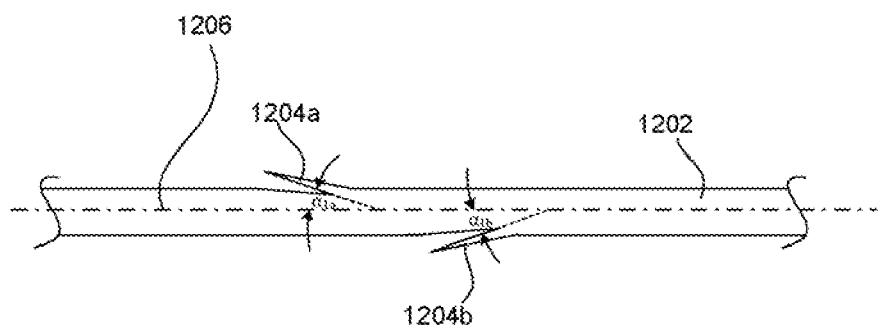
FIG. 12B is a side view of the elongated suture body of FIG. 12A.

At step 1104, retainers are formed along at least a portion of the elongated suture body, wherein the retainers have original elevations angles relative to the longitudinal axis. FIG. 12A is perspective view of a portion of an elongated suture body 1202 having retainers 1204a and 1204b cut into the suture body 1202. FIG. 12B is a side view of the elongated suture body 1202 of FIG. 12A. As can be appreciated from FIG. 12B, the retainers 1204a and 1204b have original elevation angles $\alpha_{1a}$ and $\alpha_{1b}$, respectively, relative to the longitudinal axis 1206. While original elevation angles $\alpha_{1a}$ and $\alpha_{1b}$ can be substantially similar, that need not be the case. In other words, one of elevation angles $\alpha_{1a}$ and $\alpha_{1b}$ can be different than the other.

In one embodiment, step 1104 is accomplished by cutting into the elongated suture body 1202 to form the retainers 1204 having original elevation angles relative to the longitudinal axis 1206. However, while the retainers 1204 can be formed at step 1104 by cutting the retainers into the suture body 1202, embodiments of the present invention are not limited to forming retainers in this manner.

Figure 12C:
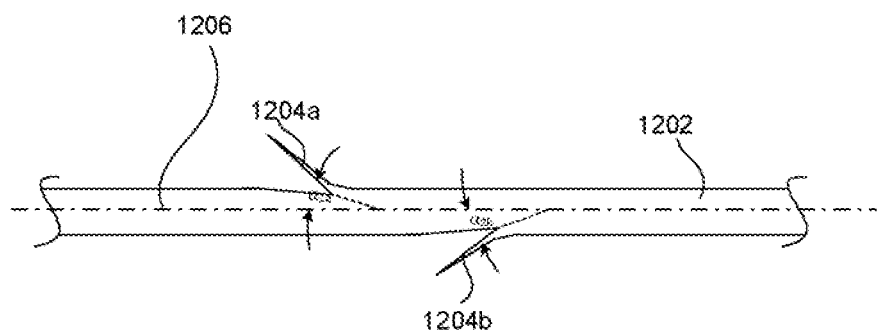
FIG. 12C is a side view of the elongated suture body of FIGS. 12A and 12B, after the elevation angles of the retainers were increased by lifting the retainers from original elevation angles (shown in FIG. 12B) to increased elevation angles (shown in FIG. 12C) using electrostatic force, in accordance with embodiments of the present invention.
Figure 12D:
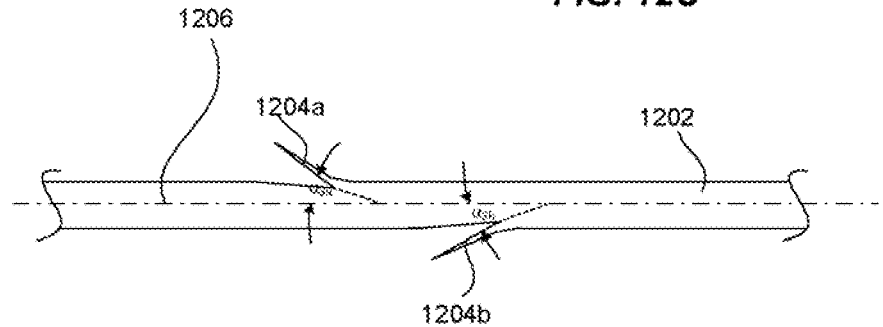
FIG. 12D is a side view of the elongated suture body of FIG. 12C after the electrostatic force is no longer applied.
Figure 13:
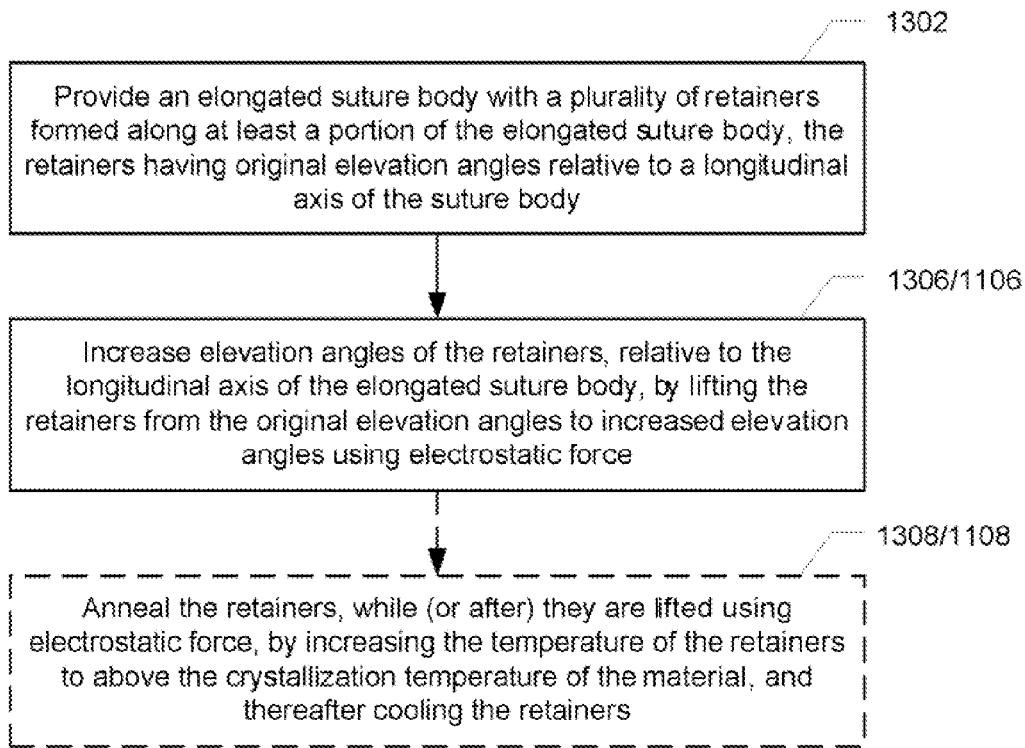
FIG. 13 is a high level flow diagram that is used to summarize methods of forming self-retaining sutures in accordance with further embodiments of the present invention.

Returning to FIG. 11, at step 1106, elevation angles of the retainers are increased, relative to longitudinal axis of the elongated suture body, by lifting the retainers from the original elevation angles to increased elevation angles using electrostatic force. FIG. 12C is a side view of the elongated suture body 1202, after the elevation angles of the retainers 1204 were increased by lifting the retainers 1204 from the original elevation angles $\alpha_{1a}$ and $\alpha_{1b}$, (shown in FIG. 12B) to increased elevation angles $\alpha_{2a}$ and $\alpha_{2b}$ (shown in FIG. 12C). In other words, $\alpha_{2a} > \alpha_{1a}$, and $\alpha_{2b} > \alpha_{1b}$. While the increased elevation angles $\alpha_{2a}$ and $\alpha_{2b}$ can be substantially similar, that need not be the case. In other words, one of the increased elevation angles $\alpha_{2a}$ and $\alpha_{2b}$ can be different than the other. An electrostatic generator can be used to produce an electrostatic force. An electrostatic generator can include, e.g., mechanical elements that are used to produce an electrostatic force, or electrodes that are used to produce an electrostatic force. Such devices are well known, and thus need not be described herein. Alternative devices and techniques for producing electrostatic force are possible, and within the scope of the present invention.

Following step 1106, plastic deformation imposed by the lifting at step 1106 maintains the retainers 1204 at elevation angles greater than the original elevation angles. However, the elevation angles at which the retainers 1204 are maintained (i.e., when no external force is applied to the retainers 1204) are likely less than $\alpha_{2a}$ and $\alpha_{2b}$. This is because after the electrostatic force is no longer applied, the retainers 1204 will tend to at least partially return to their previous state, due to the elastic and viscoelastic properties of the material from which the retainers are made. For example, referring to FIG. 12D, the maintained elevation angles of the retainers 1204a and 1204b can be, respectively, $\alpha_{3a}$ and $\alpha_{3b}$, where $\alpha_{2a} > \alpha_{3a} > \alpha_{1a}$, and $\alpha_{2b} > \alpha_{3b} > \alpha_{1b}$. In other words, the final elevation angles of the retainers 1204 are greater than the original elevation angles, but likely not as great as the elevation angles produced while the electrostatic force is being applied to lift the retainers 1204.

The retainers 1204 can be made from a material that has a corresponding crystallization temperature. Exemplary suture materials, from which the retainers can be formed, were provided above. Referring again to FIG. 11, at an optional step 1108, the retainers can be annealed, while they are being lifted using electrostatic force, by increasing the temperature of the retainers to above the crystallization temperature of the material but preferably below the melting point of the material, and thereafter cooling the retainers. This additional step 1108 can have the affect of maximizing the final elevation angles (e.g., $\alpha_{3a}$ and $\alpha_{3b}$) of the retainers by relieving stresses imposed on the retainers during lifting, eliminating viscoelastic effects, increasing the effect of creep and/or fatigue, and thus, can be beneficial. If step 1108 is performed, it would be beneficial to maintain the temperature of the retainers 1204 above the crystallization temperature for a sufficient time to allow for stress-relaxation at the points where the retainers 1204 connect to the elongated suture body 1202. In general the annealing time should be sufficiently long to allow for sufficient stress relief and/or elimination of the viscoelastic effects (memory), and/or setting in of creep and/or fatigue to allow the retainers to remain in the upward position. The time required to anneal the retainers can vary from as little as 15 minutes or less to as long as 48 hours or more, but is preferably between 30 minutes and 4 hours, depending on the material and the annealing temperature. All or some of the suture may be annealed in this fashion.

In accordance with an embodiment, the base of the retainer (the area where the retainer is connected to the suture body) is locally annealed to allow for maximum stress relief/viscoelastic effect removal to occur without annealing the suture body, and thus, without affecting the mechanical properties of the suture body. The effect of locally heating only certain portions of the suture can be obtained by heating the portions of the suture with a focused beam(s) of electromagnetic radiation (e.g. visible light, ultra-violet light, infra red light, etc.), or a focused stream of hot gas (preferably inert such as nitrogen or argon gas). Furthermore, since majority of undyed sutures are transparent to visible light, a portion at the base of each retainer can be selectively colored (e.g., painted) for targeted heating to occur, and the entire suture can be irradiated. More specifically, a color can be applied to portions of the suture where bases of retainers are formed, and radiation of that color can be shined locally or on the entire suture, and only the colored portions will heat up, thereby allowing for selective local annealing. The color can be applied after the retainers are formed, e.g., to the bases of the retainers, and potentially to the entire retainers. Alternatively, the color can be applied to the suture body prior to the retainers being formed, but such that after the retainers are formed, the bases of the retainers (and potentially the entire retainers) are colored. While the selectively annealing embodiments are useful where retainers are lifted using electrostatic force, the selective annealing embodiments can also be useful where electrostatic force is not necessarily used to lift retainers. It is also possible to locally anneal more than just the bases of the retainers, e.g., the entire retainers can be locally annealed.

In other embodiments, annealing (selective, or not) is performed after the electrostatic force is no longer being used to lift the retainers. While this embodiment may not maximize the final elevation angles, the annealing will help to prevent the retainers from returning back to their original elevation angles, or substantially thereto. Exemplary annealing techniques (heating to a certain temperature and cooling at a certain rate) are taught in U.S. Pat. No. 5,007,922, which is incorporated herein by reference. It is also possible to anneal the retainers while and after the electrostatic force is being used to lift the retainers.

In accordance with an embodiment of the present invention, the elongated suture body can include a statically chargeable agent, which will aid in the lifting of the retainers using electrostatic force. A statically chargeable agent is a material that can readily hold a charge. For example, materials from which electrons can be readily removed can readily hold a positive charge. For another example, materials from which electrons can be readily added can readily hold a negative charge. Conventional doping techniques can be used to produce such a statically chargeable agent. The statically chargeable agent can be applied to the elongated suture body before and/or after the retainers are formed at step 104, and/or during the forming of the elongated suture body. For example, the statically chargeable agent can be sprayed or otherwise deposited on the suture body, or added when manufacturing the suture body. It is also possible that an entire suture body, or portions thereof, be made of a statically chargeable material. Examples of statically chargeable agents, also referred to as statically chargeable materials, include materials of the triboelectric series, but are not limited thereto. Material such as polytetrafluoroethene (PTFE, marketed under the trademark TEFLON), polyurethane, poly vinyl chloride, polypropylene, polystyrene, some polyesters, polychlorotrifluoroethylene, polyethylene, vinylidene chloride copolyers (marketed under the trademark SARAN), polymethyl methacrylate (Acrylic), polyacrylonitrile fibers (marketed under the trademark ORLON), and some metals like silver, nickel, copper, are believed to have a tendency to become negatively charged. Other statically chargeable agents are believed to have a tendency to become positively charged, such as cellulose acetate, nylon, and proteins like polypeptides. These are just a few examples, which are not meant to be limiting. Charging of such materials can occur, e.g., through friction with another material, by transferring a charge through a charged gas, or by charging directly with an electron source (e.g., a battery or the like), but are not limited thereto. Other charging techniques, and additional details of some of the just mentioned techniques, are discussed below.

In accordance with an embodiment, the elongated suture body can be charged, before or after the retainers are formed, such that after the retainers are formed both the elongated suture body 1202 and the retainers 1204 are commonly charged, which causes repelling and thereby lifting of the retainers 1204. The retainers can be charged using various different techniques, including, but not limited to, corona charging, roller charging, brush charging, other types of friction charging, charging by use of particles (also referred to as particle charging) and triboelectric charging. The charge can also be applied by placing the elongated suture body in a magnetic field. In another embodiment, the charge can be applied by applying a current to the elongated suture body. Further, while the retainers are being lifted by repelling electrostatic force, the retainers can be annealed by increasing the temperature of the retainers to above the crystallization temperature of the material, and thereafter cooling the retainers.

Although only two retainers 1204 are shown in FIGS. 12A-12D, this is for simple illustrative purposes only. It is likely that the sutures can include hundreds of retainers 1204, although more or less are possible. It is also noted that the figures are not necessarily drawn to scale, i.e., it is likely that the retainers 1204 are not as large as shown relative to the suture body 1202. The periodicity and arrangement of the retainers 1204 can be random or organized to maximize or otherwise adjust tissue engagement strength.

As can be appreciated from the high level flow diagram of FIG. 3, specific embodiments of the present invention do not include the step of forming the retainers. Rather, a first step 1302 can be to provide an elongated suture body with a plurality of retainers already formed along at least a portion of the elongated suture body, wherein the retainers have original elevation angles relative to a longitudinal axis of the suture body. For example, a suture already having retainers cut into an elongated suture body can be purchased. Thereafter, at step 1306 elevation angles of the retainers are increased, relative to a longitudinal axis of the elongated suture body, by lifting the retainers from the original elevation angles to increased elevation angles using electrostatic force. Step 1306 is the same as step 106, and thus need not be described again. At optional step 1308, the retainers can be annealed, while (and/or after) they are lifted using electrostatic force, by increasing the temperature of the retainers to above the crystallization temperature of the material, and thereafter cooling the retainers. Step 1308 is the same as step 1108 described above, and thus need to be described again.

Figure 14:
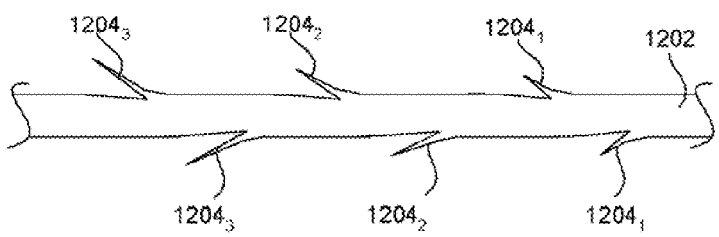
FIG. 14 is a side view of a portion of a self-retaining suture that includes retainers of varying sizes, in accordance with embodiments of the present invention.

Shown in FIG. 14 is a side view of a self-retaining suture that includes retainers 1204 of varying sizes. For example, retainers 1204$_1$ are closely spaced to one another and relatively small in size with a relatively short length as compared to retainers 1204$_2$, which are relatively medium in size with a relatively medium length, as compared to retainers 1204$_3$, which are relatively large in size with a relatively long length. The periodicity of such retainers can be random or organized, such that for example retainers 1204$_1$ occur in groups in a series and then followed by retainers 1204$_2$ which occur in groups in a series, followed by retainers 1204$_3$. The order of occurrence and the size of the groups may be altered to maximize tissue engagement strength. The different sized retainers 1204 are designed for various surgical applications. The retainer size may also vary in the transverse direction, whereby the base of the retainers may be short, medium, or long, and regardless, the suture base typically is less than about ¼ of the suture diameter. For instance, relatively larger or longer retainers 1204$_3$ are desirable for joining fat and soft tissues, whereas relatively smaller or shorter retainers 1204$_1$ are desirable for joining fibrous tissues. Use of a combination of large, medium, and/or small sized retainers on the same suture helps to ensure maximum anchoring properties when retainers sizes are customized for each tissue layer. Only two different sized sets of retainers (not shown) may be formed to the suture body 1202, or additional sets of retainers (not shown) with four, five, six, or more different sized sets than three sizes as illustrated may be formed to the suture body 1202 as desired, in accordance with the intended end use.

The retainers 1204 and the suture body 1202 can both be made of bio-absorbable material, examples of which were provided. Alternatively, the retainers 1204 and the suture body 1202 can both be made of non-absorbable material, examples of which were also provided above. In another embodiment of this invention the retainers 204 and the suture body 1202 can be partially bio-absorbable.

The retainers 1204 can be angled or canted such that the retainers substantially yield to motion of the elongated suture body 1202 within the tissue when the suture 1200 is drawn in one suture deployment direction and resist motion if the suture 1200 is drawn in an opposite suture deployment direction. The self-retaining sutures can have retainers 1204 that are unidirectional or bidirectional. If unidirectional, the self-retaining sutures can include an end that is pointed or has a needle to allow penetration and passage through tissue when drawn by the end and an opposite end that in some embodiments includes an anchor for engaging tissue at the initial insertion point to limit movement of the suture. If bidirectional, the self-retaining sutures can include retainers grouped and extending toward one deployment direction along one portion of the suture and opposing retainers grouped and extending toward an opposing deployment direction along another portion of the suture. Accordingly, when such a bi-directional suture is implanted, both groups of retainers are engaging tissue, and the retainers can resist movement of the suture through tissue in either direction. Also, a bidirectional suture can be armed with a needle at each end of the suture thread. A bidirectional suture can also have a transitional segment located between the two groups of retainers.

As mentioned above, the retainers 1204 can be formed so the retainers substantially yield to motion of the elongated suture body within the tissue when the elongated suture body is drawn in a first direction and resist motion of the elongated suture body in a second direction opposite the first direction. In specific embodiments, a bi-directional suture can be formed. More specifically, the elongated suture body can include first and second longitudinal portions. Step 1104 can include forming a first group of the retainers that extend from and along the first longitudinal portion, so that the first group of retainers substantially yield to motion of the elongated suture body within the tissue when the elongated suture body is drawn in a first direction and resist motion of the elongated suture body in a second direction opposite the first direction. Step 1104 can also include forming a second group of retainers that extend from and along the second longitudinal portion, so that the second group of retainers substantially yield to motion of the elongated suture body within the tissue when the elongated suture body is drawn in the second direction and resist motion of the elongated suture body in the first direction. Elevation angles of retainers in the first and second groups can be increased using embodiments of the present invention.

The elongated suture body 1202 can produced by any suitable method, including without limitation injection molding, extrusion, and so forth. The suture body 1202 and the retainers can be made of any suitable biocompatible material, and may be further treated with any suitable biocompatible material, whether to enhance the strength, resilience, longevity, or other qualities of the suture, or to equip the sutures to fulfill additional functions besides joining tissues together, repositioning tissues, or attaching foreign elements to tissues.

In a specific embodiment of the present invention a composite suture filament is created by co-extruding two materials to form a co-extruded elongated suture body having a core portion made of a first or inner material and outer portion formed of a second or outer material. The inner material is preferably selected such that it has excellent tensile and elastic properties and the outer material is selected to provide for the formation of retainers having a desired stiffness. In a specific embodiment the outer material has a higher elastic constant than the inner material to allow relatively stiff retainers to be formed, e.g., by cutting. The outer material may also have a larger plastic region than the inner material to allow for easier permanent deformation of the outer material when the retainers are lifted using electrostatic force. The inner material is preferably more elastic than the outer material so that the suture having retainers has an enhanced combination of retainer features, suture flexibility and tensile strength.

In a specific embodiment of the present invention a composite suture filament is created by co-extruding three (or more) materials to form a co-extruded elongated suture body having a core portion made of a first or inner material, an outer portion formed of a second or outer material, and a third or in-between material between the first and second materials. Again, the inner material can be selected such that it has excellent tensile and elastic properties and the outer material can be selected to provide for the formation of retainers having a desired stiffness. The in-between material can be an insulator, to thereby allow a magnitude of charge applied to the core portion of the suture to be different than a magnitude of charge applied to the outer material, in which the retainers can be formed. For example, the core material and outer material can both be positively charged, but the core material can have a greater magnitude of positive charge than the outer material, or vice versa. For another example, the core material and outer material can both be negatively charged, but the core material can have a greater magnitude of negative charge than the outer material, or vice versa. It is also possible that the core and outer portion be made of the same chargeable material, with an insulation material therebetween. With each of these options, electrostatic force will cause an increase in the elevation angles of the retainers, if the inner and outer portions are both positively charged or both negatively charged.

The sutures described herein may also incorporate materials that further promote tissue engagement. For example, forming the sutures of tissue engagement-promoting materials can enhance the ability of the sutures to stay in place. One such class of tissue engagement-promoting materials are porous polymers that can be extruded to form suture bodies, including both microporous polymers and polymers that can be extruded with bubbles (whether bioabsorbable or nonbioabsorbable). Sutures synthesized with such materials can have a three-dimensional lattice structure that increases tissue engagement surface area and permits tissue infiltration into the suture body itself, thus having a primary structure that promotes successful suture use. Moreover, by optimizing pore size, fibroblast ingrowth can be encouraged, further facilitating anchoring of the retainers 1204 in the tissue. Alternatively pro-fibrotic coatings or agents may be used to promote more fibrous tissue encapsulation of the retainers 1204 and therefore better engagement. Exemplary profibrotic materials, which can be used to form retainers 1204 and/or which can be applied to retainers 1204, to promote tissue growth, are disclosed in U.S. Pat. No. 7,166,570, entitled "Medical implants and fibrosis-inducing agents," which is incorporated herein by reference.

One such microporous polymer is ePTFE (expanded polytetrafluoroethylene). Self-retaining sutures incorporating ePTFE (and related microporous materials) are well-suited to uses requiring a strong and permanent lift (such as breast lifts, face lifts, and other tissue repositioning procedures), as tissue infiltration of the suture results in improved fixation and engraftment of the suture and the surrounding tissue thus providing superior hold and greater longevity of the lift.

Additionally, self-retaining sutures described herein may be provided with compositions to promote healing and prevent undesirable effects such as scar formation, infection, pain, and so forth. This can be accomplished in a variety of manners, including for example: (a) by directly affixing to the suture a formulation (e.g., by either spraying the suture with a polymer/drug film, or by dipping the suture into a polymer/drug solution), (b) by coating the suture with a substance such as a hydrogel which will in turn absorb the composition, (c) by interweaving formulation-coated thread (or the polymer itself formed into a thread) into the suture structure in the case of multi-filamentary sutures, (d) by inserting the suture into a sleeve or mesh which is comprised of, or coated with, a formulation, or (e) constructing the suture itself with a composition. Such compositions may include without limitation anti-proliferative agents, anti-angiogenic agents, anti-infective agents, fibrosis-inducing agents, anti-scarring agents, lubricious agents, echogenic agents, anti-inflammatory agents, cell cycle inhibitors, analgesics, and anti-microtubule agents. For example, a composition can be applied to the suture before the retainers are formed, so that when the retainers engage, the engaging surface is substantially free of the coating. In this way, tissue being sutured contacts a coated surface of the suture as the suture is introduced, but when the retainer engages, a non-coated surface of the retainer contacts the tissue. Alternatively, the suture may be coated after or during formation of retainers on the suture if, for example, a fully-coated rather than selectively-coated suture is desired. In yet another alternative, a suture may be selectively coated either during or after formation of retainers by exposing only selected portions of the suture to the coating. The particular purpose to which the suture is to be put or the composition may determine whether a fully-coated or selectively-coated suture is appropriate; for example, with lubricious coatings, it may be desirable to selectively coat the suture, leaving, for instance, the tissue-engaging surfaces of the sutures uncoated in order to prevent the tissue engagement function of those surfaces from being impaired. On the other hand, coatings such as those comprising such compounds as anti-infective agents may suitably be applied to the entire suture, while coatings such as those comprising fibrosing agents may suitably be applied to all or part of the suture (such as the tissue-engaging surfaces). The purpose of the suture may also determine the sort of coating that is applied to the suture; for example, self-retaining sutures having anti-proliferative coatings may be used in closing tumour excision sites, while self-retaining sutures with fibrosing coatings may be used in tissue repositioning procedures and those having anti-scarring coatings may be used for wound closure on the skin. As well, the structure of the suture may influence the choice and extent of coating; for example, sutures having an expanded segment may include a fibrosis-inducing composition on the expanded segment to further secure the segment in position in the tissue. Coatings may also include a plurality of compositions either together or on different portions of the suture, where the multiple compositions can be selected either for different purposes (such as combinations of analgesics, anti-infective and anti-scarring agents) or for their synergistic effects.

FIGS. 15A to 20C:

Polyglycolic acid (PGA) is the simplest aliphatic polyester polymer and has a glass transition temperature between 35-40° C. and a melting point between 225-230° C. The monomer, glycolic acid, occurs naturally in sugarcane syrup and in the leaves of certain plants, but can also be synthesized chemically. Ring-opening polymerization of the cyclic dimmer, glycolide, yields high molecular weight polymers. PGA has a high crystallinity (45-55%) that leads to its insolubility in water and most organic solvents but is soluble in highly fluorinated solvents like hexafluoroisopropanol (HFIP) and hexafluoroacetone sesquihydrate, which can be used to prepare solutions of the high molecular weight PGA polymers for melt spinning and film preparation. Fibers of PGA exhibit high strength and modulus (7 GPa) and are particularly stiff. PGA undergoes both enzymatic and hydrolytic degradation. Polyglycolide can be easily hydrolyzed owing to the presence of the ester linkage in its backbone, where the polymer is converted back to its monomer glycolic acid. The degradation process is erosive and involves the diffusion of water into the amorphous (non-crystalline) regions of the polymer matrix, cleaving the ester bonds and then after the amorphous regions have been eroded, the crystalline portions of the polymer become susceptible to hydrolytic attack. When exposed to physiological conditions, PGA is broken down by enzymes with esterase activity. The degradation product, glycolic acid, is non toxic and it can enter the tricarboxylic acid cycle after which it is excreted as water and carbon dioxide. A part of the glycolic acid is also excreted in urine. PGA sutures loose half their strength after two weeks and 100% after four weeks. The polymer is completely resorbed in four to six months.

Poly-lactic acid (PLA) is the most widely used biodegradable polyester. PLA polymers are not only used as implants in human bodies, but can also replace petroleum-based polymers in many application items. The monomer lactic acid is found in blood and muscle tissue as a product of the metabolic process of glucose. High molecular weight polylactide is obtained by ring-opening polymerization of the cyclic dimer of lactic acid. Lactic acid can be derived by fermentation of starchy products such as corn, and then converted to PLA through low-cost, high-yield catalytic polymerization (U.S. Pat. No. 5,981,694 which is expressly incorporated by reference in its entirety). Due to the asymmetrical β carbon of lactide acid, D and L stereoisomers exist, and the resulting polymer can be either isomeric (D, L) or racemic DL. Petrochemical PLA is a mixture of D- and L-stereoisomer (50/50), whereas the fermentation of renewable resources forms uniquely L-lactic acid. Proteinase K preferentially degrades L-L, L-D and D-L bonds as opposed to D-D linkages. PLA is water resistant, unstable in acidic and alkali solutions, soluble in halogenated hydrocarbons, ethyl acetate, THF and dioxane. Poly(L-lactic acid) (PLLA) is semi-crystalline, and suitable for applications such as orthopedic fixings and sutures (U.S. Pat. No. 5,567,431 which is expressly incorporated by reference in its entirety). Poly(D, L-lactic acid) (PDLLA) is amorphous, degrades more rapidly, and is more attractive as a drug delivery system. PLA degrades via composting within three weeks, by first undergoing a hydrolysis reaction and then a microbial decomposition during which carbon dioxide and water are generated. PLA is more hydrophobic than PGA and hydrolyzed more slowly in vivo.

Polycaprolactone (PCL) is a water stable, hydrophobic and semi-crystalline polymer. The preparation of PCL and its copolymers from ε-caprolactone can be effected by different mechanisms including anionic, cationic, coordination and radical polymerization. PCL can be hydrolyzed by fungi or through chemical hydrolysis. Chemical degradation of PCL is slower than poly(α-hydroxyalkanoic acids). Since the degradation of PCL takes place over about 2 years, copolymers have been developed for applications demanding an accelerated degradation rate. PCL possesses good mechanical properties, is more hydrophobic than and compatible with many polymers.

Poly(p-dioxanone) (PDO) also referred as poly(oxyethylene glycoate) and poly(ether ester) is formed by the ring-opening polymerization of p-dioxanone (U.S. Pat. No. 4,052,988 which is expressly incorporated by reference in its entirety). The polymer must be processed at the lowest possible temperature to prevent depolymerization back to monomer. The monofilament loses half of its initial breaking strength after 20 days and is absorbed within 180 days.

Glycolic acid has been copolymerized with other monomers to reduce the crystallinity and thereby increase the flexibility of the resulting copolymers. In various embodiments of the invention, the suture core is composed of copolymers including poly(glycolide-co-1,3-trimethylene carbonate) (TMC/PGA) (see U.S. Pat. No. 5,695,879 which is expressly incorporated by reference in its entirety), poly(glycolide-co-ethylene carbonate), poly(glycolide-co-propylene carbonate), poly(lactide-co-glycolide) (PLAGA) (see U.S. Pat. No. 4,960,866 which is expressly incorporated by reference in its entirety), poly(lactide-co-methylglycolide), poly(lactide-co-dimethylglycolide), poly(lactide-co-diethylglycolide), poly (lactide-co-dibutylglycolide), poly(lactide-co-butylene succinate), poly(glycolide-co-caprolactone), poly(glycolide-co-valerolactone), poly(glycolide-co-decalactone), poly (glycolide-co-propiolactone), poly(glycolide-co-butyrolactone) and poly(glycolide-co-pivalolactone, poly (glycolide-co-ethylene oxide) (PGA/PEO), poly(glycolide-co-trioxane), poly(glycolide-co-1,3-dioxanone), poly (glycolide-co-1,4-dioxane) or poly(glycolide-co-1,4-dioxanone) (PGA/PDO).

Lysine triisocyanate (LTI) can be blended with hydroxycarboxylic acid copolymer blends to improve the immiscibility of the two different kinds of biodegradable polymers. Fracture properties such as the J-integral at initiation, and the total fracture energy and impact strength can be improved as a result of the addition of LTI to these copolymers. The LTI isocyanate groups can react with the polymer hydroxyl or carboxyl groups resulting in void formation being inhibited and the improved properties.

In accordance with another aspect, the present invention provides sutures comprising a composite filament of two of more different co-extruded materials in which at least one inner material enhances the tensile strength and/or the flexibility of the suture and potentially does this without compromising the creation, elevation, deployment and engagement of the retainers on the suture.

In accordance with a specific embodiment of the present invention a self-retaining suture is made by inserting a core made from one material that has high strength and flexibility into a sheath made from a different material selected to enhance formation, positioning and strength of a plurality of retainers. In a specific embodiment the sheath material is more contractible than the core material and the core material has more tensile strength and/or more flexibility than the sheath material such that the suture has an enhanced combination of retainer features, tensile strength and flexibility compared to a similar suture formed from a single-material filament.

In accordance with specific embodiments of the present invention a self-retaining suture is made by forming a composite filament having a core made from one material that has high strength and a sheath made from a different material. A plurality of retainers is formed from the material of the sheath in the surface of the filament. In specific embodiments the sheath is made from a material that contracts upon a stimuli and therefore the retainers are forced to stand proud due to the contraction of the sheath material. The core material does not contract at the same rate as the sheath and is also more elastic and/or more flexible than the sheath material.

Considering FIG. 15, composite filament 2100 can be formed by any method known in the art for making a composite filament having two different materials each having the properties required for the function of the material in the filament. One suitable method is extrusion of the core and then inserting the core through a sleeve. Another suitable method is extrusion of a material over a preformed filament. Alternatively, the two materials can be co-extruded. Other methods of forming a coating layer on a preformed filament can also be utilized including, without limitation, dip coating, spray coating, curtain coating and/or chemical deposition, such as chemical vapor deposition (CVD).

In accordance with the foregoing background and the limitations of the prior art, the present invention provides, contractible or shrinkable or shape-memory self-retaining sutures which enhance the ability of the retainers to stand proud and thereby anchor into the self-retaining suture into the surrounding tissue, enhanced tissue holding capabilities, enhanced maximum load, and enhanced clinical performance.

Contractible Shape-Memory Polymer Film: As discussed above, the present invention provides compositions, configurations, methods of manufacturing and methods of using contractible, shrinkable and shape-memory tubing in self-retaining sutures in surgical procedures which greatly increase the ability of the self-retaining sutures to anchor into the surrounding tissue to provide superior holding strength and improve clinical performance.

Shape-memory materials are materials which have the ability to memorize one or more shapes different than the current temporary shape and transition between the shapes in response to a stimulus. A wide variety of materials are known to exhibit shape-memory effects including, for example, polymers, thermoplastics, metal alloys, hydrogels and ceramics. A shape-memory material transitions from one shape to another shape in response to a transition stimulus—typically a temperature change. However, a wide variety of other transition stimuli can be used to effect transition between shapes in shape-memory materials including, for example, electromagnetic radiation, electrical current, magnetic fields, pH, ionic strength and solvation (including, but not limited to water solvation). The transition stimulus is typically dependent upon the shape-memory material.

Shape-memory polymers transition between shapes in response to an external stimulus. Depending on the material required there are two ways that heat shrink can be manufactured. The heat shrink tubing can be manufactured from partially polymerized material which contains many un-reacted monomers. When the tubing is heated, the un-reacted monomers polymerize. This increases the density of the material as the monomers become bonded together therefore taking up less space. Accordingly, the volume of the material shrinks.

Heat shrink manufactured can also be expansion-based. This process involves producing the tubing as normal, heating it to just above the polymer glass transition temperature and mechanically stretching the tubing (often by inflating it with a gas) finally it is rapidly cooled. When heated at a later time, the tubing will "relax" back to the un-expanded size. The expansion based material is often cross-linked through the use of electron beams, peroxides or moisture, to make the tubing maintain its shape, both before and after shrinking.

In one embodiment of the invention, the shape-memory polymers have a current shape and one or more stored shapes. A first stored shape is produced by conventional methods and the configuration of that shape is largely determined by covalent bonds between the polymer chains. The material is then deformed into a second temporary form under conditions in which the second form is fixed by mechanical connections made by particular "switching segment". The transformation into the second temporary forms is a process called programming. The polymer maintains the second form until another shape is recalled by a predetermined external stimulus. In an embodiment of the invention, the core is inserted into heat shrink tubing, which is heated to produce a tight fit between the core and the outer sheath. The retainers are then cut into the suture and then the suture is again heated to further contract the heat shrink tubing and make the retainers stand proud.

The transition stimulus for shape memory polymers is often temperature, but can also be an electric field, magnetic field, electromagnetic radiation (e.g. light), pH change, chemical change or solvation change (e.g. water). In some instances the transition stimulus is a means for raising the temperature of the polymer. Passing an electric current through a conductive polymer can be used to raise the temperature by resistive heating. Applying a fluctuating magnetic field to a polymer can be used to heat a polymer having ferromagnetic properties. Illuminating a polymer with electromagnetic radiation can be used to heat a polymer which absorbs (or is treated to absorb) the particular wavelength used. However, other transition stimuli such as pH, chemical change and solvation can be used to "melt" the switching segment without a change in temperature.

Other Contractible Polymer Film: In an embodiment of the invention, a self retaining suture is coated with a gel/solution comprising a contractible nematic elastomer polymer film made up of a fiber having a polymeric backbone with a liquid crystalline (LC) side group and a cross linking side group, both bonded to the backbone. In an embodiment of the invention, cross links between the cross linking side groups link the polymeric backbone molecules. The invention further comprises a method for making a self retaining suture comprising the steps of: providing a self retaining suture and a solution containing a copolymer having a LC side group and a cross linking side group; commencing a cross linking reaction with the copolymer and before the cross linking reaction is complete depositing this gel/solution on the self retaining suture in contract with the retainers so that when the copolymer cross links and shrinks the retainers stand proud. The invention also includes a surgical kit comprising a scalpel, gauze and the self retaining suture core with retainers cut in the core to which has been applied a nematic elastomer polymer film on the outer coating of the suture core in order to make the retainers stand proud.

A method is described for preparing the nematic elastomer gel/solution containing the LC fibers from a side chain LC terpolymer containing two side-chain mesogens and a non-mesogenic group that acts as a reactive site for cross-linking. The initial cross linking can occur in the gel phase, and the sample can be mechanically stretched to obtain a monodomain sample before the cross-linking is complete. A fiber drawn from a mixture of a copolymer and a cross-linker show that the fiber has a significant uniaxial contraction as a function of temperature across the nematic-isotropic phase (i.e., going from disordered to an ordered state). By varying the chemical composition of the elastomer, cross linking temperature, and cross linking method, the operating temperature and amount of contraction can be controlled.

A variety of copolymers can be used to make the fiber. As used herein, the term "copolymer" includes polymers, copolymers and terpolymers having any number of copolymerized monomers, including block, alternating, and random copolymers. The backbone of the copolymer can include acrylic, vinyl, siloxane, and/or norbornene units. The copolymer can be made up of one or more of these units or alternatively can be made up of only one unit such as polysiloxane. In the case of polysiloxane the side groups are added to the polymer via hydrosilation reactions. The copolymer has side groups that can be cross linked. The copolymer also has LC side groups which include nematic (groups that can induce ordering in the copolymer) and/or smectic groups (groups that can induce ordering in the copolymer resulting in layers).

The coupling between the LC side group and the polymer backbone is important for the thermostrictive behavior of elastomeric materials. Studies have shown that the orientation order of the side groups will induce orientation order in the polymer backbone. For example, the use of laterally affixed LC mesogens can produce large backbone anisotropy. This is as opposed to LC side groups that are attached to the backbone at the end of the side group. In various embodiments of the invention, exemplary LC side groups include $C_jH_{2j+1}$—OBz-COO-Ph(X)—Y, where j is an integer, Bz=benzyl, Ph=phenyl, Y is selected from benzonitrile, p-carboxy-benzonitrile and p-carboxy-Bz-$C_jH_{2j+1}$ and X=COO—$(CH_2)_n$-*, where * indicates the linkage point of attachment to the copolymer backbone.

The cross linking side group can be an alkyl alcohol group, such as butanol. When the backbone is polyacrylate, this can be incorporated by reacting with 4-ol-butyl acrylate. When the backbone is a polysiloxane, the cross linking side group can be incorporated by reacting with 2-(but-3-eneyloxy)tetrahydropyran. Subsequent reaction with methanol and an ion-exchange resin can be used to remove the tetrahydropyran and convert the side chain to an alcohol. This procedure can be used because an unprotected hydroxyl group could also react with the polysiloxane backbone. A copolymer can also include multiple LC or cross linking side groups.

The copolymer can be cross linked and drawn into a fiber. This can be done by mixing a cross linking agent with the copolymer. When the cross linking side group has a hydroxyl group, then the cross linking agent can have isocyanate groups, so that carbamide linkages can be formed between the cross linking side group and the cross linking agent. Alternatively, when the cross linking side group has epoxy groups, alcohol-ether linkages can be formed. Acrylic cross linking agents can also be used. Once the cross linking reaction has occurred, the cross linking side group can be an alkyl group such as 1,4-n-butyl. Suitable cross linking agents include 4,4'-methylene bis(phenyl isocyanate), diisocyanoalkane and 4,4'-diisocyanoto biphenyl.

Fiber drawing can be performed by starting the cross linking reaction, such that the viscosity of the mixture increases to allow for drawing a fiber, and drawing the fiber before cross linking has completed. Once cross linking is complete, the fiber can maintain its shape. The copolymer cross linking agent mixture can be warmed prior to drawing. The self retaining suture can be dipped in the mixture and used to draw a fiber from the mixture which is twirled around the self retaining suture to form a fiber, film or covering extending from one end of the self retaining suture to the other end of the self retaining suture and coming into contact with the face of the retainers cut into the self retaining suture.

When the fiber is made, the LC side groups can have orientation order. When a stimulus such as thermal, electrical, or photo is applied to the fiber, these side groups can become substantially reoriented or disordered. This can have the effect of changing the dimensions of the fiber, such as shortening the length of the fiber. Electrical stimulation can be effective when the LC side chain has a dielectric anisotropy. Photo stimulation can be effective when LC side chain has a photoexcitable group such as an azo group, which changes its conformation upon irradiation.

LC mesogens can also spontaneously order during the spinning of the fiber. Therefore, in a nematic elastomer with side-on attachment of the LC mesogen, the orientation order of the mesogen as well as the polymer backbone can be along the fiber axis. Accordingly, the contraction can occur along the fiber axis. Bundles of fibers can be deployed in self retaining sutures, the number of fibers in each bundle dictating the force that can be generated.

A solution containing a series of polysiloxanes with cholesteric side chains having odd and even numbers of atoms along the polysiloxane chain can be used to form a film, which can be induced to contract through a stimulus. The first stage involves a slight cross-linking of the cholesteric side chain polysiloxanes while applying a stress field. Subsequently, a second cross-linking reaction is performed which fixes the uniaxial alignment. By this method nematic elastomers of large dimensions with permanent alignment and highly anisotropic mechanical properties can be produced. Varying the content of odd and even spacer groups in the cholesteric side chain elastomers can vary the amount of contraction of the polymer film along its axis in response to a stimuli. Application of such a film to a self retaining suture core can result in the film being contractible upon a stimulus. Further cross linking of the cholesteric side chains in the polysiloxane can be used to fix the retainers in the proud position.

The stimuli for contraction of nematic elastomers can include temperature, light, magnetic field, electric field or stress applied perpendicular to the main axis. The resulting contraction of the film can be used to make the retainers in the self retaining suture core stand proud.

Self-Retaining Suture Systems: The present invention provides compositions, configurations, methods of manufacturing self-retaining sutures where a shape-memory tubing or nematic elastomer is used to keep the retainers proud. Self-retaining sutures incorporating a shape-memory tubing or a or nematic elastomer affect the geometry of features of the retainers cut into the filament core before deployment of the suture into tissue.

Figure 15A:
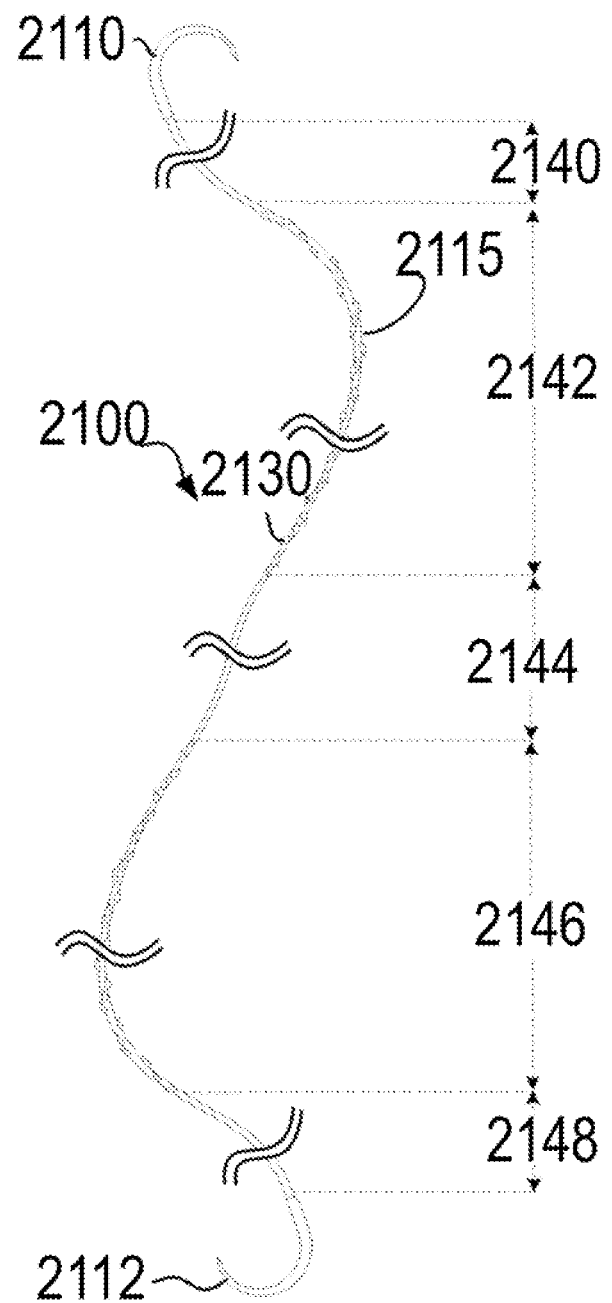
FIGS. 15A and 15B show perspective views of a self retaining suture comprising an (inner core not shown) and an outer layer in accordance with various embodiments of the present invention.

FIG. 15A illustrates a self-retaining suture system 2100. The heat shrink coating self-retaining suture 2100 is a bidirectional self-retaining suture and comprises needles 2110 and 2112 attached at each end of heat shrink self-retaining suture thread 2100. Heat shrink self-retaining suture thread includes a plurality of retainers 2130 distributed on the surface of a filament 2115. In the lead-in region 2140 there are no retainers 2130. In region 2142 of heat shrink suture thread there are a plurality of retainers 2130 arranged such that, when retainers 2130 are elevated, the suture thread can be deployed in the direction of needle 2110 but resists movement in the direction of needle 2112. In transition region 2144, there are no retainers 2130. In region 2146, there is a plurality of retainers 2130 arranged such that, when retainers 2130 are elevated, the suture thread can be deployed in the direction of needle 2112 but resists movement in the direction of needle 2110. In lead-in region 2148 of self-retaining suture thread 2100 there are no retainers 2130. A break is shown in each of regions 2140, 2142, 2144, 2146 and 2148 to indicate that the length of each region can be varied and selected depending upon the application for which the suture is intended to be used. Although a bidirectional heat shrink self-retaining suture system 2100 is illustrated, the present invention includes self-retaining suture systems of a wide variety of retainer and needle configurations described above. Likewise the configuration of each of needles 2110 and 2112 can be any of the range of different surgical needles developed for use in different applications. Needles 2110 and 2112 can have the same configuration or different configurations.

Figure 15B:
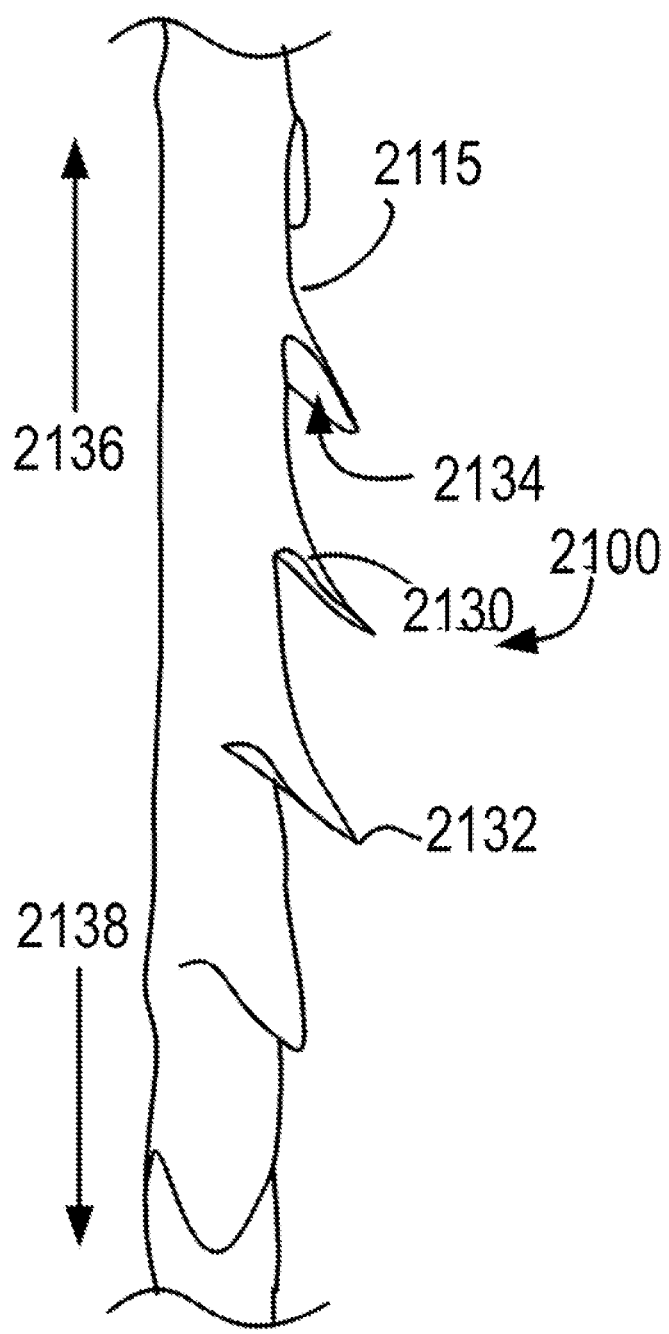

FIG. 15B illustrates a magnified view of heat shrink self-retaining suture thread 2100 in region 2142 of FIG. 15A. As shown in FIG. 15B, a plurality of retainers 2130 is distributed on the surface of filament 2115. The affixation of self-retaining sutures after deployment in tissue entails the penetration of retainer ends into the surrounding tissue resulting in tissue being caught between the retainer and the suture body. The inner surface of the retainers 2130 contacts tissue that is caught between the retainers 2130 and the filament surface 2115. The inner surface of the retainers is referred to herein as the "tissue engagement surface" or "inner retainer surface." As illustrated in FIG. 15B, each retainer 2130 has a tip 2132 and tissue retainer surface 2134.

In a heat shrink self-retaining suture system, the retainers 2130 include a shape-memory component. In some embodiments, the heat shrink component can be used to cause retainers 2130 to stand proud in response to a stimulus. With the retainer 2130 elevated, when self-retaining suture thread 2100 is moved in the direction of arrow 2138, tip 2132 or retainer 2130 engages tissue causing retainers 2130 to further extend and engage the tissue with tissue retainer surface 2134 thereby preventing movement of the suture in that direction. However, prior to elevation of retainer 2130 it can be possible to move heat shrink suture thread 2100 in both of directions 2136, 2138 without interference by retainers 2130. Thus, the use of heat shrink suture thread 2100 allows for selectable control of the self-retaining features.

Figure 15C:
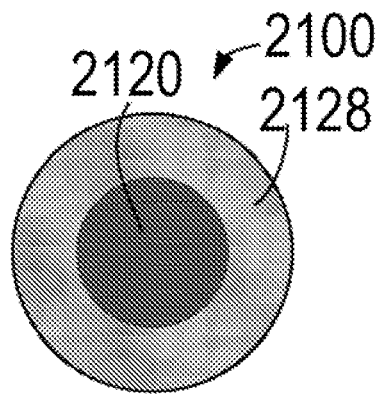
FIG. 15C is a cross-sectional view of the self retaining suture of FIGS. 15A and 15B illustrating the arrangement of an inner core and an outer layer.
Figure 15D:
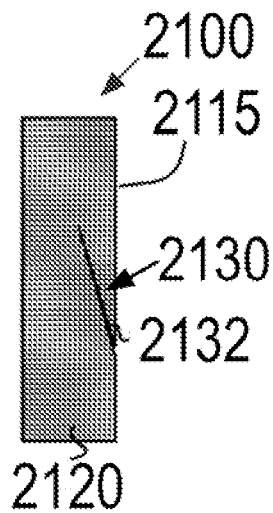
FIGS. 15D and 15E show sectional views of the self retaining suture of FIGS. 15A, 15B and 15C illustrating the shape of self retainers in the suture.
Figure 15E:
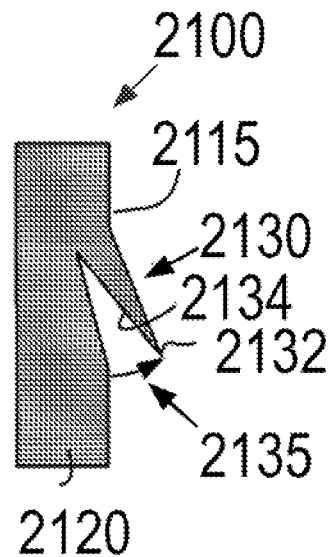

FIG. 15C shows a cross-sectional view of shape-memory suture thread 2100 comprising a core 2120 and an outer coating 2128 in accordance with an embodiment of the invention. FIG. 15D shows an embodiment of the invention, where a suture thread 2100 in which retainer 2130 is cut into the core 2120, where the retainer 2130 lies flat against the surface of the filament 2115 and where the tip 2132 is not in a position to engage tissue. FIG. 15E shows a suture thread 2100 in which retainer 2130 is cut into the core 2120, where the retainer 2130 is elevated above the surface of filament 2115 with tip 2132 and tissue retainer surface 2134 in position to engage tissue. Upon the application of a stimulus retainer 2130 changes from the configuration of FIG. 15D to the configuration of FIG. 15E. Retainer tip 2132 thus moves in the direction of arrow 2135 away from filament surface 2115 in response to the stimulus. The stimulus can be, for example, heating the heat shrink tubing 2120 to a transition temperature. The particular transition temperature can be selected by modifying the composition of the heat shrink material.

Heat Shrink Self-Retaining Suture Formation, Programming and Activation: Single or multi-filament suture threads as described herein can be produced by any suitable method, including without limitation, one or a combination of injection molding, stamping, cutting, laser, extrusion, and so forth. The outer layer can be applied to the inner core or can be made separately as a tubing and the inner core threaded into the tubing. With respect to cutting, polymeric thread or filaments can be manufactured or purchased for the suture body, and the retainers can be subsequently cut onto the suture body. Such retainers can be hand-cut, laser-cut, or mechanically machine-cut using blades, cutting wheels, grinding wheels, and so forth. During cutting either the cutting device or the suture thread can be moved relative to the other, or both can be moved, to control the size, shape and depth of cut. Particular methods for cutting retainers on a filament are described in U.S. patent application Ser. No. 09/943,733 titled "Method Of Forming Barbs On A Suture And Apparatus For Performing Same" to Genova et al., and U.S. patent application Ser. No. 10/065,280 titled "Self-retaining sutures" to Leung et al. both of which are incorporated herein by reference.

Figure 16:
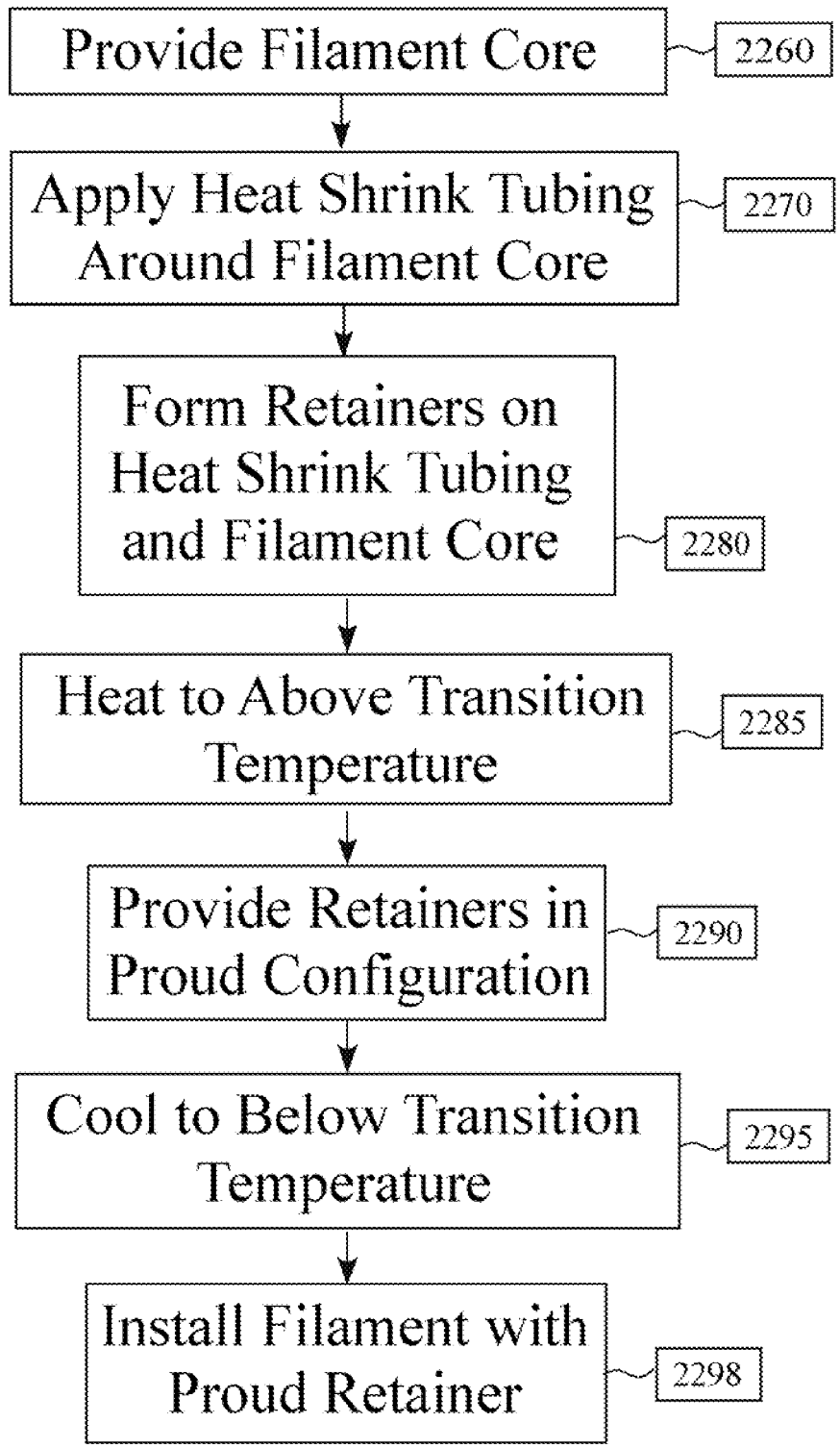
FIG. 16 is a flowchart of the process of making a self-retaining suture with a heat shrink coating in accordance with various embodiments of the present invention.

FIG. 16 is a flow chart demonstrating an exemplary process for making a suture thread using heat shrink tubing 2328 to keep the retainers 2330 proud (see FIG. 17). FIG. 17A through 3D illustrate steps of the process of FIG. 16. In step 2260 of FIG. 16, a filament core 2320 is provided. FIG. 17A shows a sectional view of the filament 2360 before inserting in the heat shrink tubing.

Figure 17A:
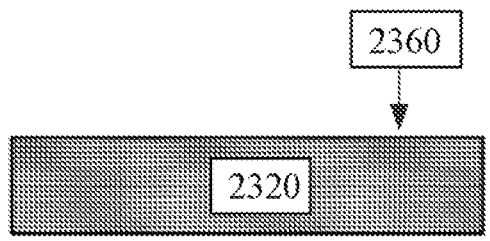
FIGS. 17A to 17D show sectional views of a heat shrink coated self-retaining suture during the steps of the process of FIG. 16.
Figure 17B:
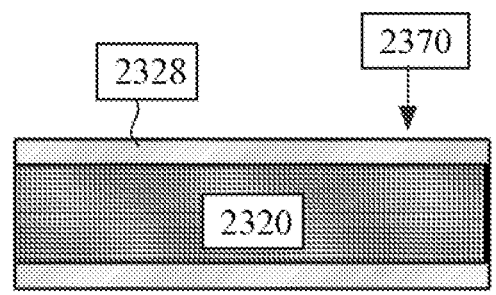

In step 2270 of FIG. 16, and FIG. 17B, the heat shrink tubing 2328 is applied around the filament core 2320. The heat shrink polymer is selected and/or designed to have a suitable transition temperature. FIG. 17B shows a sectional view of the filament 2370 before retainer formation.

Figure 17C:
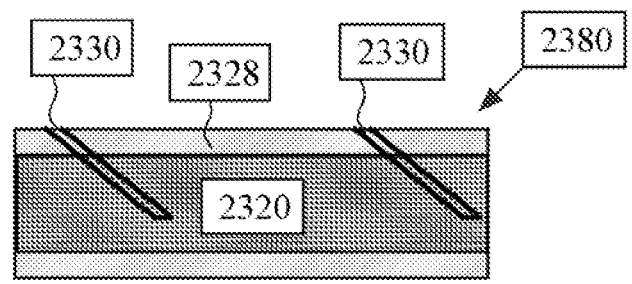

In step 2280 of FIG. 16, and FIG. 17C, the retainers 2330 can be formed by using any of a wide range of technologies. FIG. 17C shows a sectional view of the filament 2380 where the retainer 2330 is cut through the heat shrink tubing 2328 into the filament core 2320. Note that in this embodiment, retainer 2330 has been formed by removing material from heat shrink tubing 2328 and filament core 2320. The material can be removed using any of a wide range of technologies including without limitation: hand-cutting, laser-cutting, stamping or machine-cutting using blades, cutting wheels, grinding wheels, and so forth. In various embodiments of the invention, the retainer 2330 so formed, can have a configuration which is elevated above the body of filament 2380.

Figure 17D:
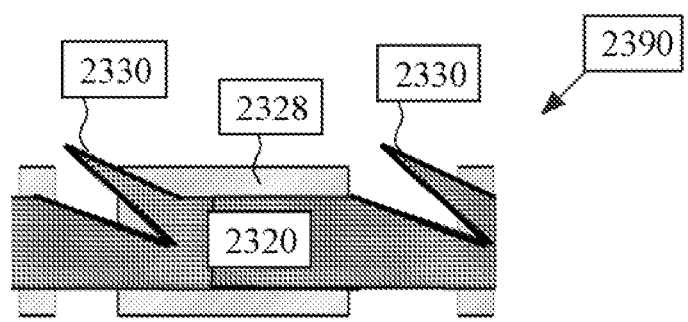

In step 2285 of FIG. 16, the heat shrink tubing is heated and contracts as a result. In step 2290 of FIG. 16, and FIG. 17D, as the heat shrink layer 2328 contracts, the retainers 2330 cut into the filament core 2320 move away from the surface of the filament 2390 to stand proud. FIG. 17D shows a sectional view of the filament 2390 before cooling and insertion into a wound. In step 2295 of FIG. 16, the heat shrink tubing is cooled and the heat shrink tubing remains contracted and the retainers are in the proud position. In step 2298 of FIG. 16, the self retaining filament can be installed.

Where the transition stimulus is a temperature, the shrink tubing polymer is heated above the transition temperature in step 2285. The heating device, can be any device capable of heating the filament tubing, for example, a source of electromagnetic radiation such as infra-red or visible light. However, filament tubing or coating can also be heated by magnetic or electrical fields, an electric current passed through filament core 2320 or simply by bathing the suture in sterile saline above the transition temperature.

The properties of a heat shrink suture can also be utilized to affect the size and/or shape of the filament instead of or in addition to the retainers of the self-retaining suture. Heat shrink can be used to reduce a filament diameter and length. Thus, in a simple example, the shape-memory effect can be used to reduce the length of a suture after deployment in order to approximate a wound. Table I shows some typical shrink rates for polymers.

TABLE I

Typical contraction rates for polymers.

| Polymer | Shrink rates (/in/in) |
|---|---|
| ABS | 0.005-0.007 |
| Acetal | 0.018-0.025 |
| Acrylic | 0.002-0.008 |
| Nylon 66 | 0.012-0.018 |
| Polycarbonate | 0.005-0.007 |
| Polypropylene | 0.010-0.025 |

Figure 18:
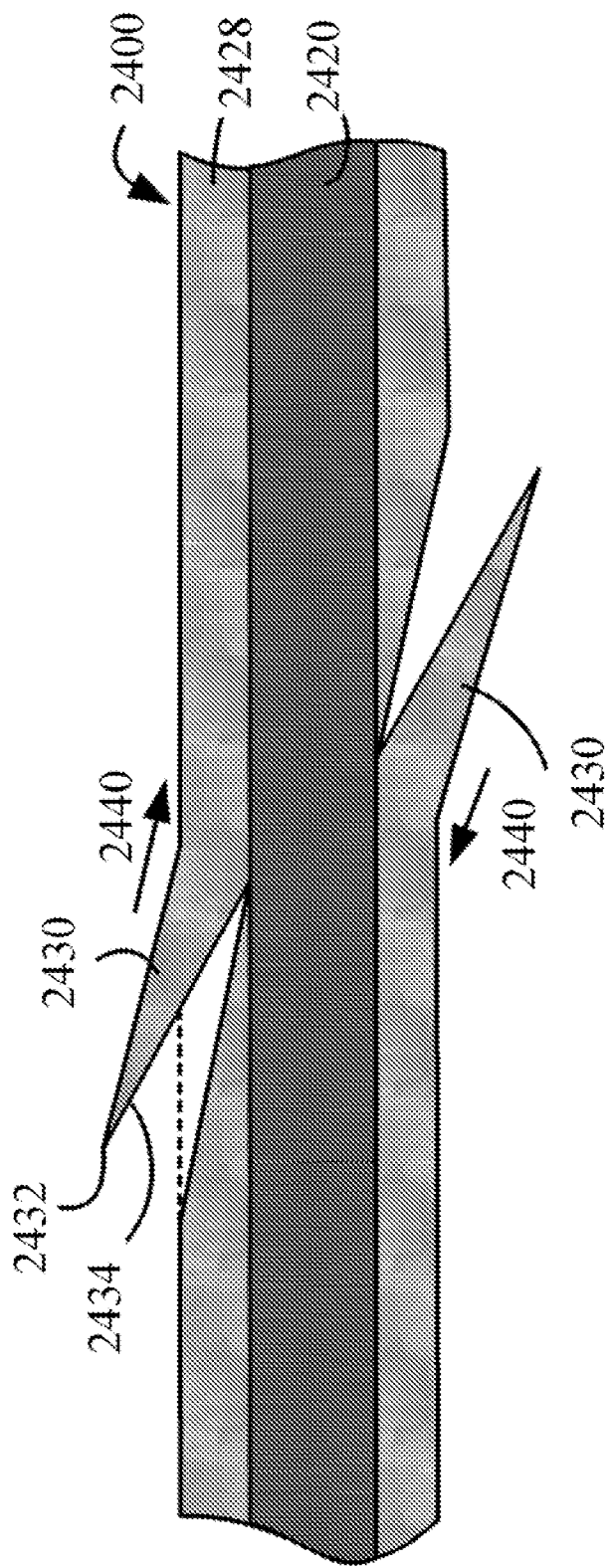
FIG. 18 is a sectional view of a heat shrink coated self-retaining suture, where retainers do not penetrate into the core of a suture in accordance with various embodiments of the present invention.

FIG. 18 shows a shrink self-retaining suture system 2400. The shrink tubing 2428 can be made of a shape-memory polymer, such as heat shrink tubing. The system comprises a filament 2400 and a plurality of retainers 2430 cut into the heat shrink tubing 2428 but not cut into the suture core 2420. When the filament 2400 reaches the transition temperature, the heat shrink tubing 2428 begins to contract in the direction shown by arrows 2440. Retainers 2430 fan out from filament 2400 so that the retainer tip 2432 can insert into tissue and retainer surface 2434 can contact tissue surface so as to be able to catch tissue between the retainers 2430 and the heat shrink tubing 2428.

Figure 19:
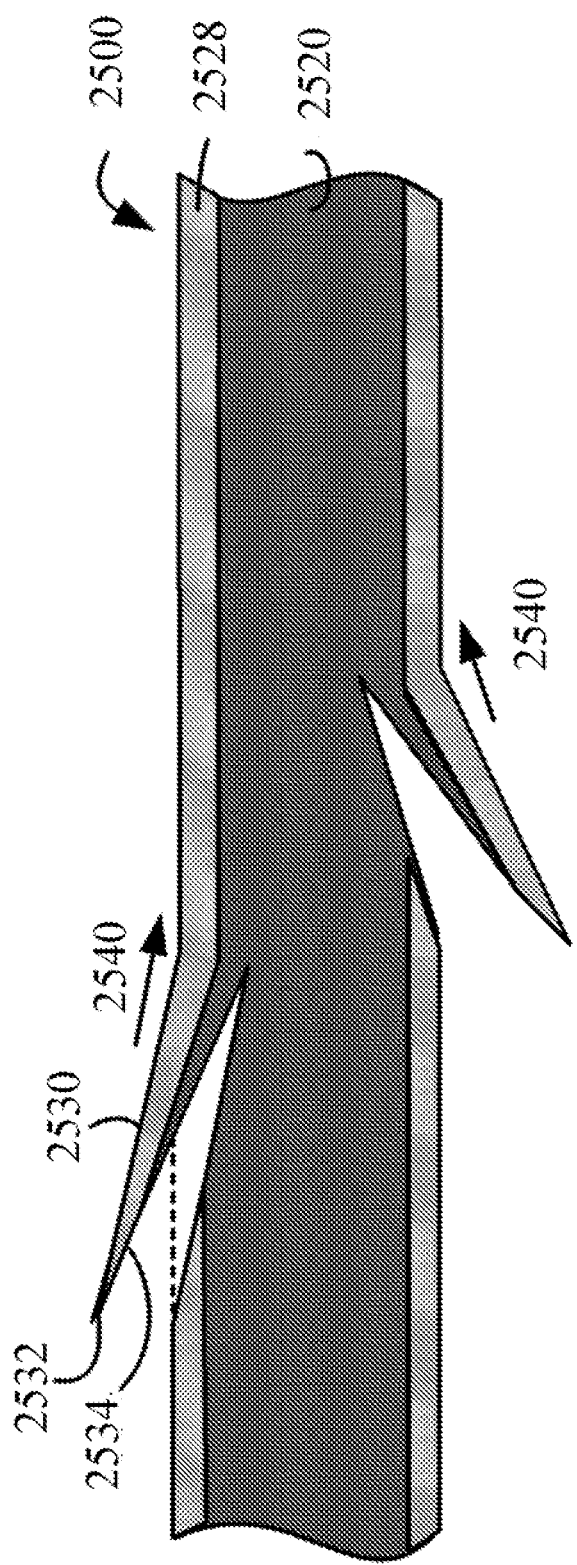
FIG. 19 is a sectional view of a heat shrink coated self-retaining suture, where retainers do penetrate into the core of a suture in accordance with various embodiments of the present invention.

FIG. 19 shows a shrink self-retaining suture system 2500. The shrink tubing 2528 can be made of a shape-memory polymer, such as heat shrink tubing. The system comprises a filament 2500 and a plurality of retainers 2530 cut into the heat shrink tubing 2528 and the suture core 2520. When the filament 2500 reaches the transition temperature, the heat shrink tubing 2528 begins to contract in the direction shown by arrows 2540. Retainers 2530 fan out from filament 2500 so that the retainer tip 2532 can insert into tissue and retainer surface 2534 can contact tissue surface to be able to catch tissue between the retainers 2530 and the intact filament core 2520.

A heat shrink tubing with an appropriate transition temperature can be of particular interest as the filament can be manufactured, and the retainers cut and the suture stored and the retainers deployed by heating the suture above the transition temperature prior to supplying to the surgeon or after supplying to the surgeon but before insertion in the wound or after insertion in the wound. In one configuration, the suture is inserted with the retainers standing proud. In an alternative embodiment of the present invention, the suture is inserted below the transition temperature and then the temperature rises above the transition temperature and the retainers stand proud and become deployed in the body. If the transition temperature is less than or equal to the temperature of tissue, filament 2400, 2500 will begin to contract as soon as it equilibrates in temperature with the surrounding tissue.

In alternative embodiments, an external stimulus can be required to cause elevation of the retainers. Such an external stimulus can be, for example, the application of heat to cause a temperature rise in the suture in excess of natural body temperature. The temperature rise can be caused by heating the suture outside the body prior to deployment. Alternatively, magnetic particles can be embedded in the material of the suture and caused to heat the suture material by magnetic induction caused by application of a magnetic field through the tissue of the subject after deployment of the suture. Additionally, shape-memory polymers which contract upon application of UV light, pH or other stimuli which can be applied to the suture after deployment in the tissues can be used. In such cases, the transition stimulus can be controlled in order to cause all or part of filament 2400, 2500 to contract thus a measure of control of the wound approximation and/or the force applied to tissues can be achieved.

In various embodiments of the invention, a coating can be applied to an elongated suture core prior to or after cutting retainers into the suture core, wherein the coating can contract to make the retainers stand proud. The contraction of the coating can be activated through interaction with an activator. In an embodiment of the invention the activator is a solution, wherein the coating contracts due to a change in pH, hydration, or a change in ionic strength. Alternatively, in a variety of embodiments, the activator can be selected from the group consisting of electromagnetic force, magnetic field, ultraviolet (UV) radiation, heat, infra-red (IR) radiation, free radical initiator, heat or UV radiation.

Figure 20A:
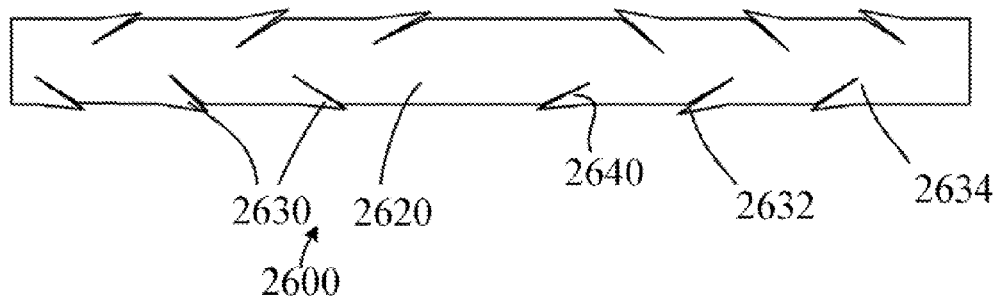
FIGS. 20A-20C show sectional views of a self-retaining suture, where in (A) the retainers penetrate into a core of a suture but are not standing proud, (B) a solution has been deposited on the core and (C) the contraction of the solution upon a stimulus causes the self retainers to stand proud in accordance with various embodiments of the present invention.
Figure 20B:
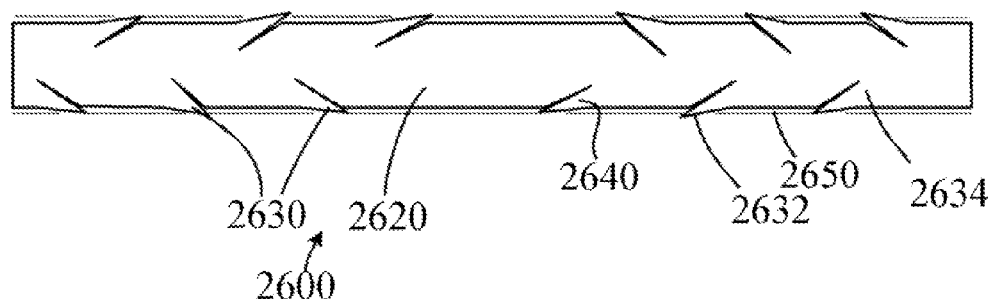
Figure 20C:
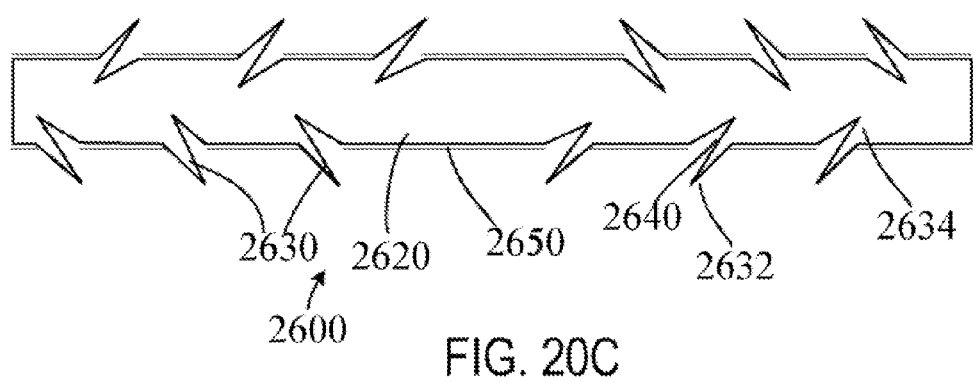

FIG. 20 shows a nematic elastomer self-retaining suture system 2600. The system comprises a filament 2600 and a plurality of retainers 2630 cut into the filament core 2620. Shown in FIG. 20A, the retainers 2630 are not standing proud from the filament 2600 and therefore the retainer tip 2632 can barely insert into tissue and retainer surface 2634 can barely contact the tissue surface to be able to catch tissue between the retainers 2630 and the intact filament core 2620. Shown in FIG. 20B, a self retaining suture is dipped in a solution/gel in which the nematic elastomer is drawn as a film along the main axis of the self retaining suture. The retainers 2630 are still not standing proud from the filament 2600. By twirling the self retaining suture (not shown), the nematic elastomer can be applied to the filament core without coating the retainer tip 2632. Shown in FIG. 20C, as the stimulus is applied the nematic elastomer contracts and the retainers 2630 stand proud from the filament 2600. The retainer tip 2632 can then insert into tissue and the retainer surface 2634 can contact the tissue surface to be able to catch tissue between the retainers 2630 and the indent in the filament core 2640.

In an alternative embodiment of the invention, the retainers can be cut into the suture after the nematic elastomer has been applied onto the suture core.

A nematic elastomer with an appropriate transition temperature can be of particular interest as the filament can be manufactured, and the retainers cut and the suture stored and the nematic elastomer applied and the retainers deployed prior to supplying to the surgeon or after supplying to the surgeon but before insertion in the wound or after insertion in the wound. In one configuration, the suture is inserted with the retainers standing proud. In an alternative embodiment of the present invention, the suture is inserted and then the temperature rises above the transition temperature and the retainers stand proud and become deployed in the body. If the transition temperature is less than or equal to the temperature of tissue, filament 2600 will begin to contract as soon as it equilibrates in temperature with the surrounding tissue.

Any suitable manufacturing process can be used to form the stock filament material for embodiments of the present invention. In an embodiment, composite materials can be spun into fibers to be used as a monofilament or multifilament core. To produce fibers having the core/sheath structure of FIG. 15, the core is inserted into a sheath or the sheath is sprayed or otherwise applied.

In differing embodiments of the invention, the sutures that can be modified according to the teachings of this invention include both degradable and non-degradable sutures. In various embodiments of the invention, the suture compositions can be polypropylene, nylon, caprolactone, caprolactone glycolide copolymer, glycolide, glycolide lactide copolymer, lactide, and poly dioxanone prior to modification.

In an alternative embodiment of the invention, the sutures can be coated with an antibacterial coatings either prior to or after raising the temperature to the transition temperature to inhibit bacterial colonization with *Staphylococcus aureus*. The antibacterial agent used to coat the suture can be selected from the group consisting of cyanoalkylated hydroxypropylcellulose and triclosan.

Figure 21:
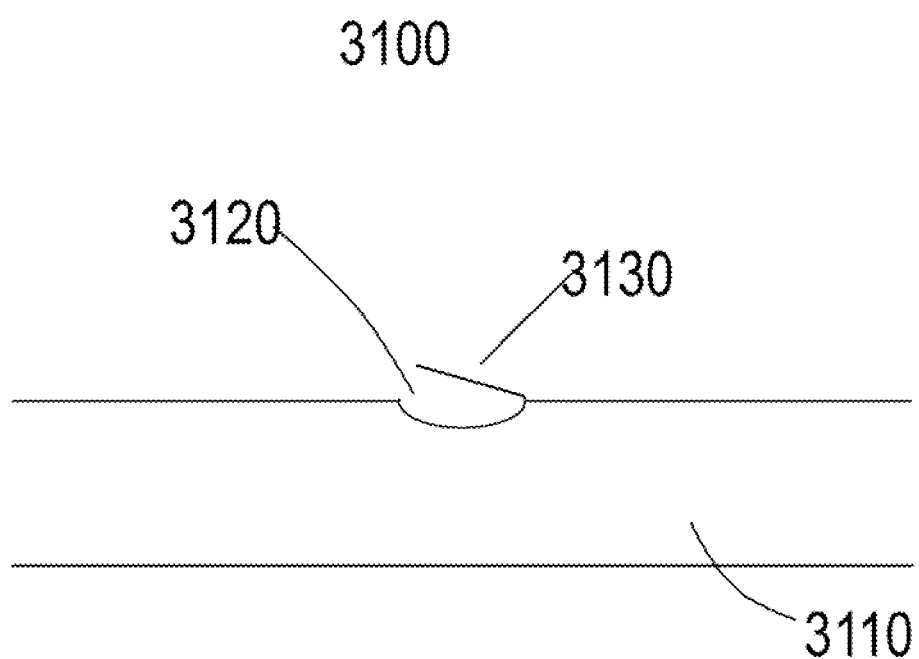
FIG. 21 shows a self retaining suture with a retainer cut from the suture that is not extended from the suture core.
Figure 22A:
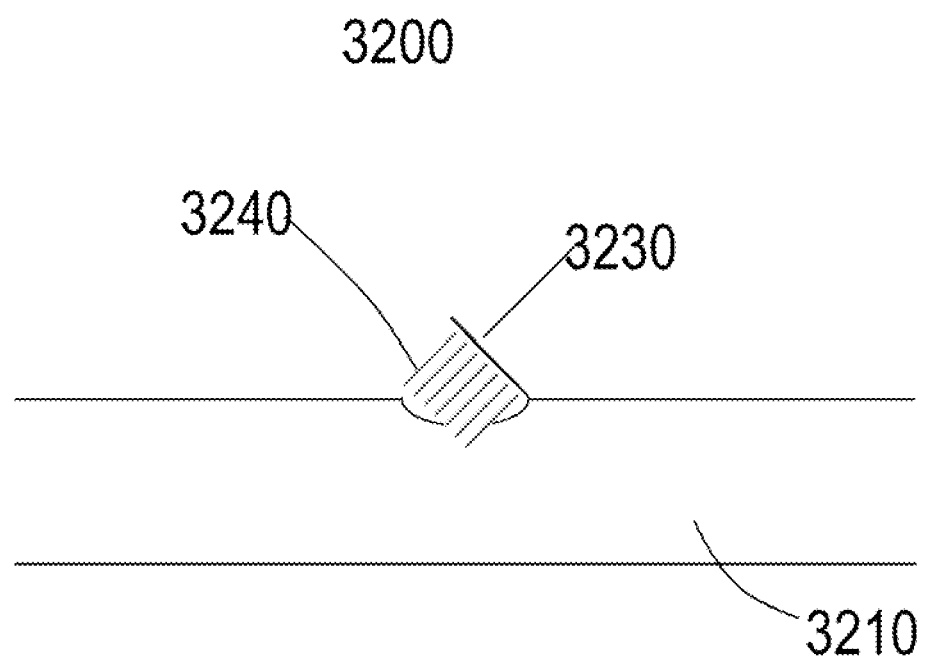
FIG. 22A shows an embodiment of the invention, where a solution has been deposited in a hole corresponding to the suture retainer expands and forces the retainer into an extended position.
Figure 22B:
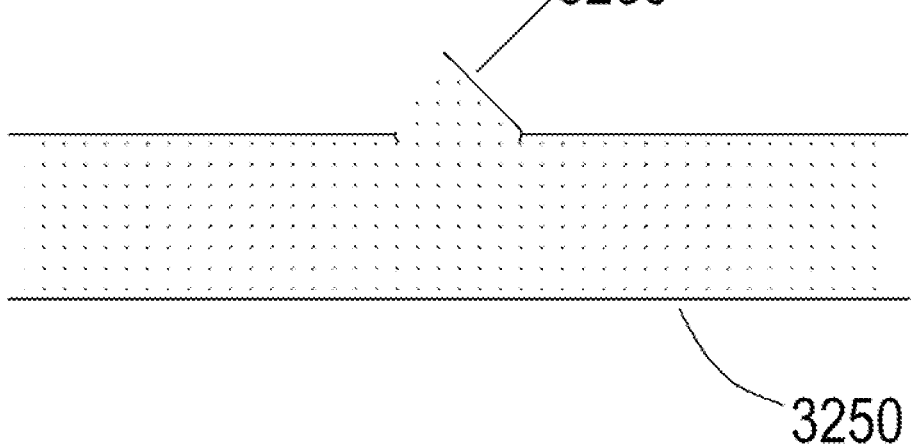
FIG. 22B shows an embodiment of the invention after a film has been applied to hold the retainer extended away from the core.

FIGS. 21 to 25B:

In an embodiment of the invention, a self-retaining suture 3100 includes one or more elongated filaments. FIG. 21 shows an embodiment of the invention, where the filament material 3110 is cut producing a hole 3120 to prepare a retainer 3130. The retainer 3230 can be extended away from the filament 3210 by placing a solution into the hole 3240 where the solution expands and forces the retainer 3230 into an extended position as shown in FIG. 22A. In FIG. 22B the retainer 3230 of a self-retaining suture 3200 can be locked into the extended position by applying a film 3250. Each retainer helps the suture resist movement in a direction opposite from which the retainer faces. The multi-filaments can be woven, braided or random oriented. In an alternative embodiment of the invention, the sutures can have grooves or wells in the outer material for an adhesive to pool for better delivery to the final site of adhesion. The disposition of the retainers on the suture body can be ordered, e.g., staggered, spiral, overlapping, or random. Also, the retainers can be configured with a specific angle, depth, length and separation distance.

Figure 23A:
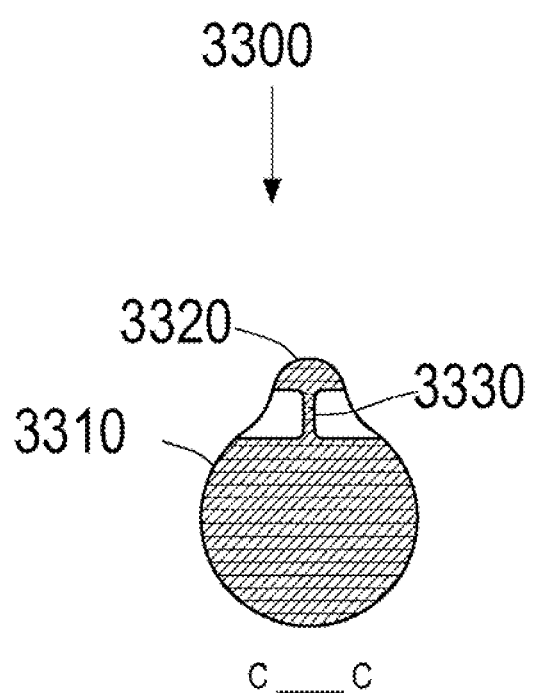
FIG. 23A shows a cross-sectional view of an embodiment of the invention, where a retainer is pinched or otherwise formed from the self-retaining sutures core.
Figure 23B:
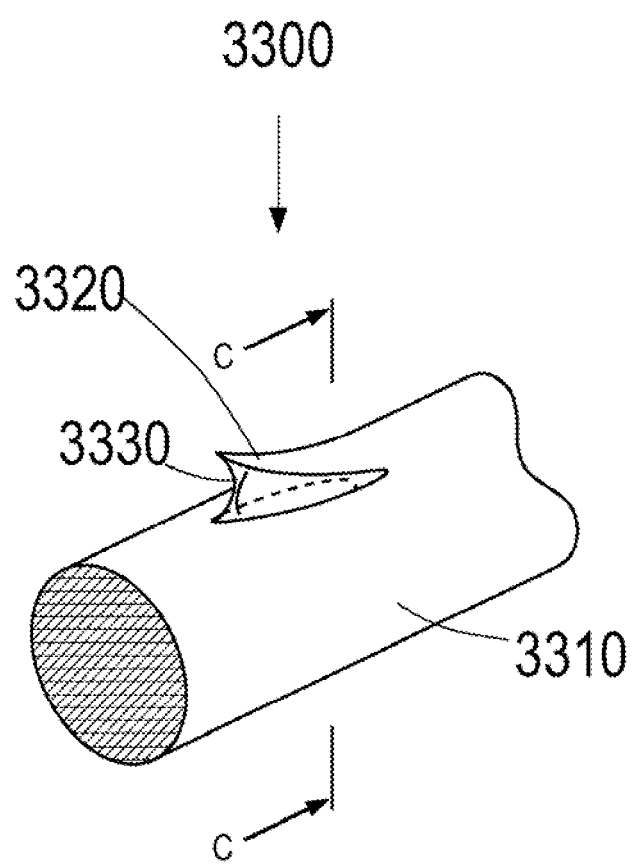
FIG. 23B shows a perspective view of the embodiment of the invention of FIG. 23A.

In an alternative embodiment of the invention, self-retainers are pinched into a monofilament core by squeezing or pinching the monofilament core. As shown in FIGS. 23A and 23B, in an embodiment of the invention, the self-retaining suture 3300 has one or more retainers 3320 formed by squeezing or pinching or otherwise deforming the monofilaments 3310 causing the retainer 3320 to form out of the deformed material drawn from the suture core or thread body 3310 and outer coating or outer sheath. Generally, it is believed that the fin 3330, as well as the bottom of the retainer 3320 that is connected to the fin, formed by such squeezing will be plastically deformed. One advantage of forming a retainer by pinching the suture core or thread body is that it can be easy to form. In this embodiment of the invention, the retainers are formed by squeezing or otherwise deforming a part of the suture and causing the retainer to form out of deformed material drawn from a monofilament suture core. An advantage of this method of retainer forming is the supporting fin that is left underneath the retainer in order to prevent the retainer from laying down flat. In various embodiments of the invention, the width and length of a fin 3330, formed between the retainer 3320 and the core 3310, can be controlled by adjusting the speed with which the suture core or body 3310 passes through a squeezing tool, the shape of the squeezing tool, the frequency of application and withdrawal of the squeezing tool and the pressure applied by the squeezing tool.

Figure 24A:
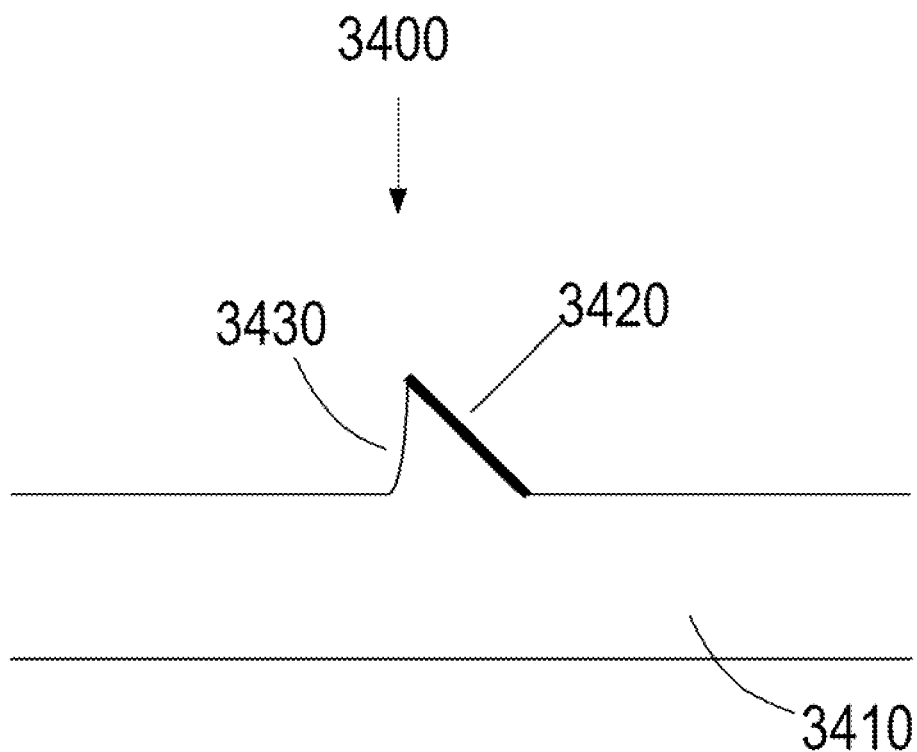
FIG. 24A shows a profile view of a suture with a pinched retainer of another embodiment of the invention.
Figure 24B:
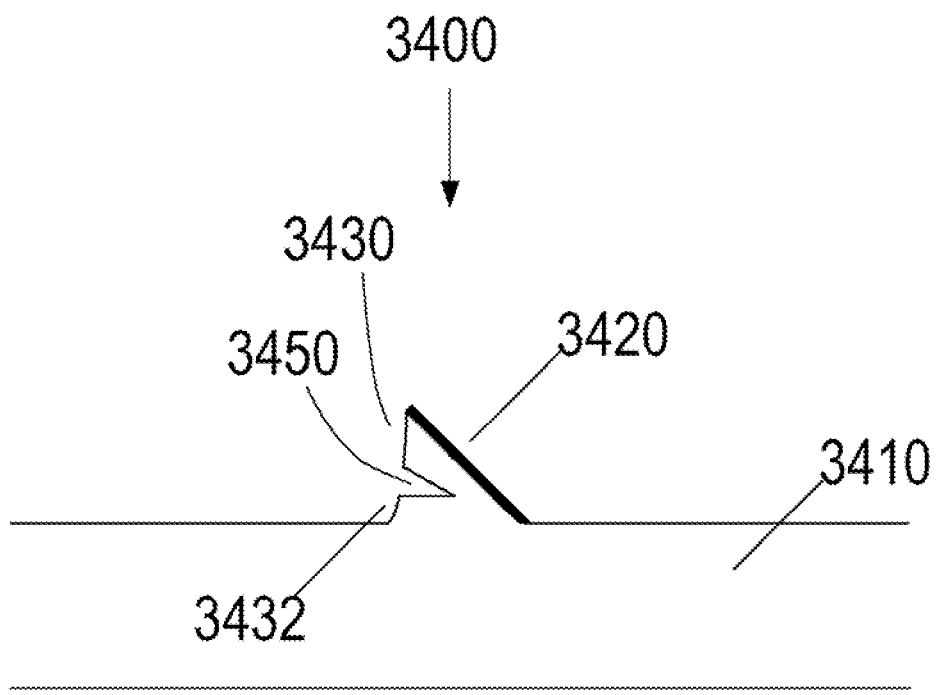
FIGS. 24B, 24C and 24D show profile views of a suture with a pinched retainer of another embodiment of this invention, with the embodiment in several positions.
Figure 24C:
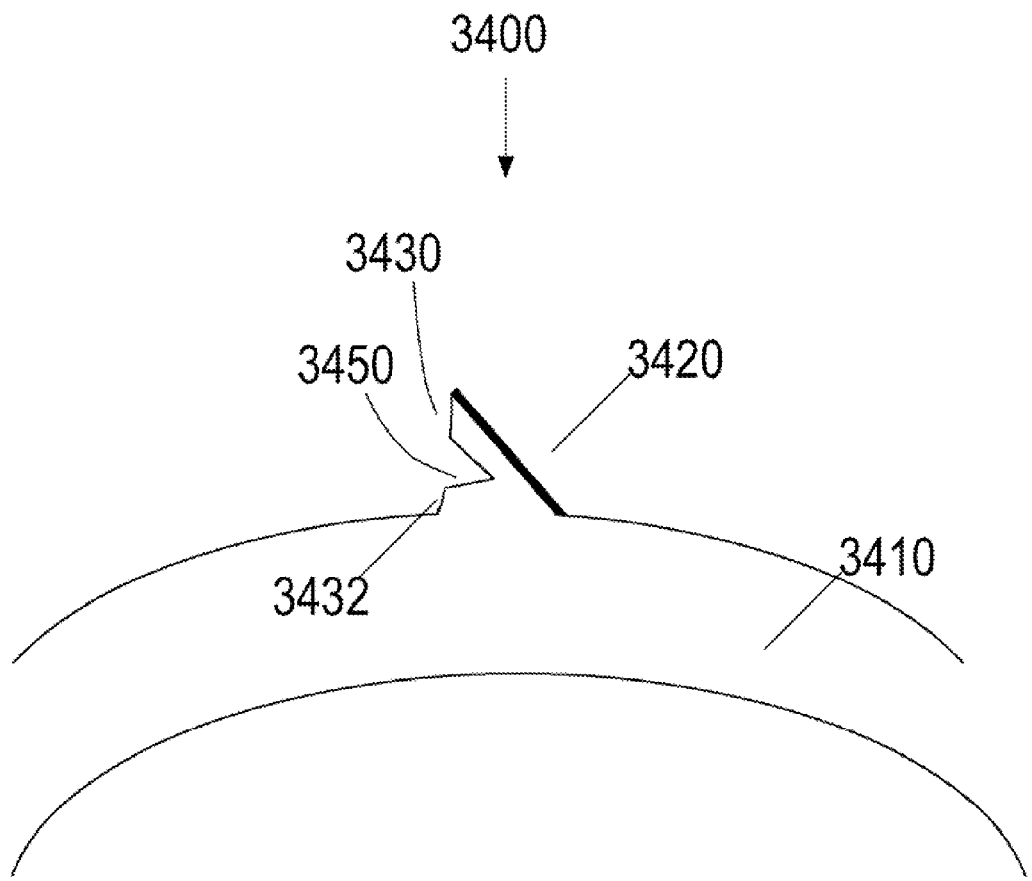
Figure 24D:
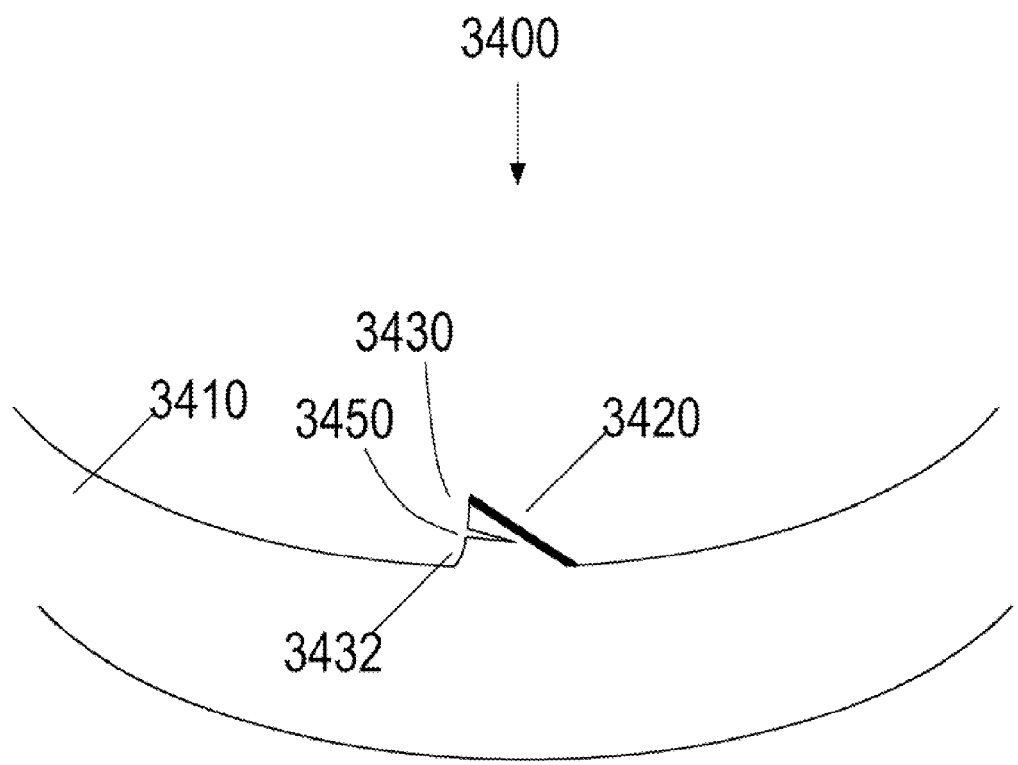

As shown in FIG. 24A, in various embodiments of the invention, after the suture core or body 3410 is squeezed or otherwise deformed to form the retainer 3420, a cut can be made in the fin 3430, reducing the amount of material under the retainer 3420 (see FIG. 24B). The cut in the fin 3430 minimizes the impediment of the fin 3430 in allowing the suture 3400 with retainer 3420 to be inserted into the tissue, and allows for better fixation in the tissues once inserted. With the cut 3450, the retainer 3420 can lie closer to the body of the suture during insertion and deployment, allowing for an easier deployment. FIGS. 24A-24D show profile views of sutures 3400 according to various embodiments of the invention. FIG. 24A depicts a side view of a suture 3400 that has been squeezed or otherwise formed by deformation of the suture core or body 3410 in order to produce one or more retainers such as retainer 3420 and a fin 3430 which supports and spaces the retainer 3420 from the core or body 3410. It is to be understood that such a suture can have a multiplicity of retainers 3420 so formed or deformed from the core 3410 and located at various positions along the length of the core 3410. FIG. 24B to FIG. 24D depict a suture 3400 that is the suture 3400 as depicted in FIG. 24A with the addition of a cut or slot 3450 formed in the fin 3430 forming an inferior or base fin portion 3432 located below the cut and the superior fin portion 3430 located above the cut. The cut may be formed by a number of techniques including using a blade to form the cut after the fin and retainer is formed, and also by using a squeezing or deforming tool that simultaneously formed the fin and retainer and also the cut in the fin. The cut or slot 3450 in the fin can be made with a simple cut or may be made by the removal of, for example, a wedge shaped section from the fin as depicted in FIG. 24B.

FIG. 24C depicts the embodiment of FIG. 24B with the suture curved outwardly with respect to the retainer 3420, such that the retainer 3420 and in particular the superior fin portion 3430 project more prominently from the core 3410 and the inferior or base fin portion 3432. As is evident from FIG. 24C the area of the cut 3450 has been enlarged due to the projection of the retainer 3420 further away from the core 3410 of the suture 3400. FIG. 24D depicts the embodiment of FIG. 24B with the suture curved inwardly with respect to the retainer, such that the retainer 3420 projects less prominently from the core 3410 as for example compared with FIG. 24B. It is noted that due to the remaining material of the fin and in particular the inferior or base fin portion 3432 located below the cut and the superior fin portion 3430 located above the cut, with the suture curved inwardly, the retainer does not settle back into the core of the suture, but maintains a prominence and projection above the core of the suture. The base fin portion 3432 accordingly acts as a stop ensuring that the retainer does not settle back into the core 3410. Accordingly, even with the suture curved inwardly as depicted in FIG. 24D, the retainer is prominent enough to engage tissue when the suture is for example pulled in a direction opposite to the direction of the initial deployment of the suture in the tissue.

Figure 25A:
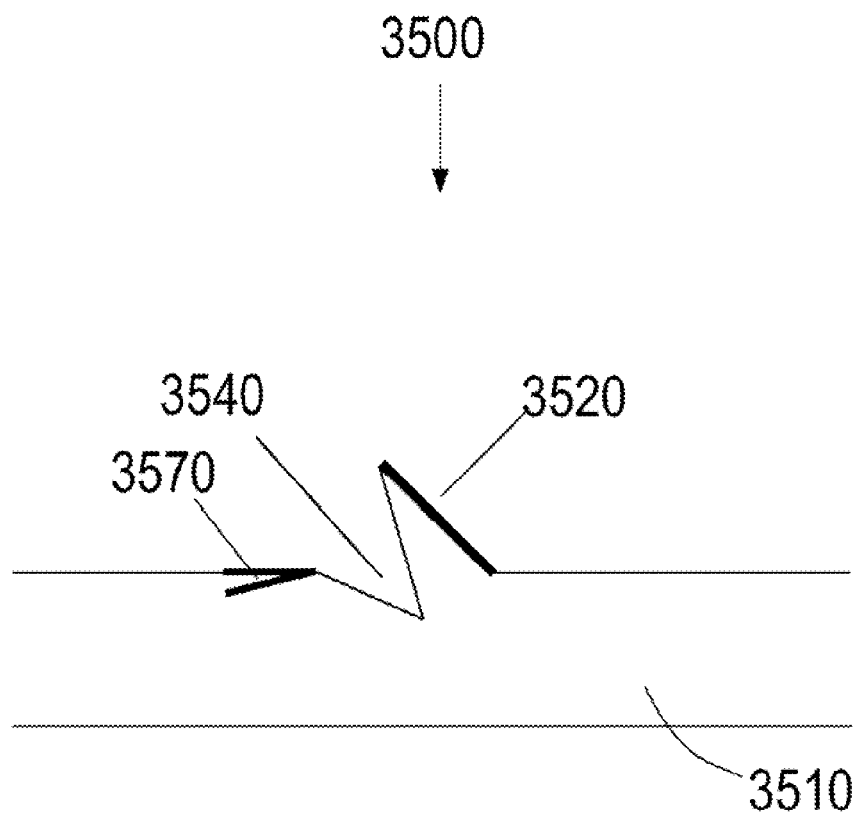
FIG. 25A shows a profile view of another embodiment of the invention with a suture with a retainer and an element that can prevent movement of the retainer associated with cutting the retainer.
Figure 25B:
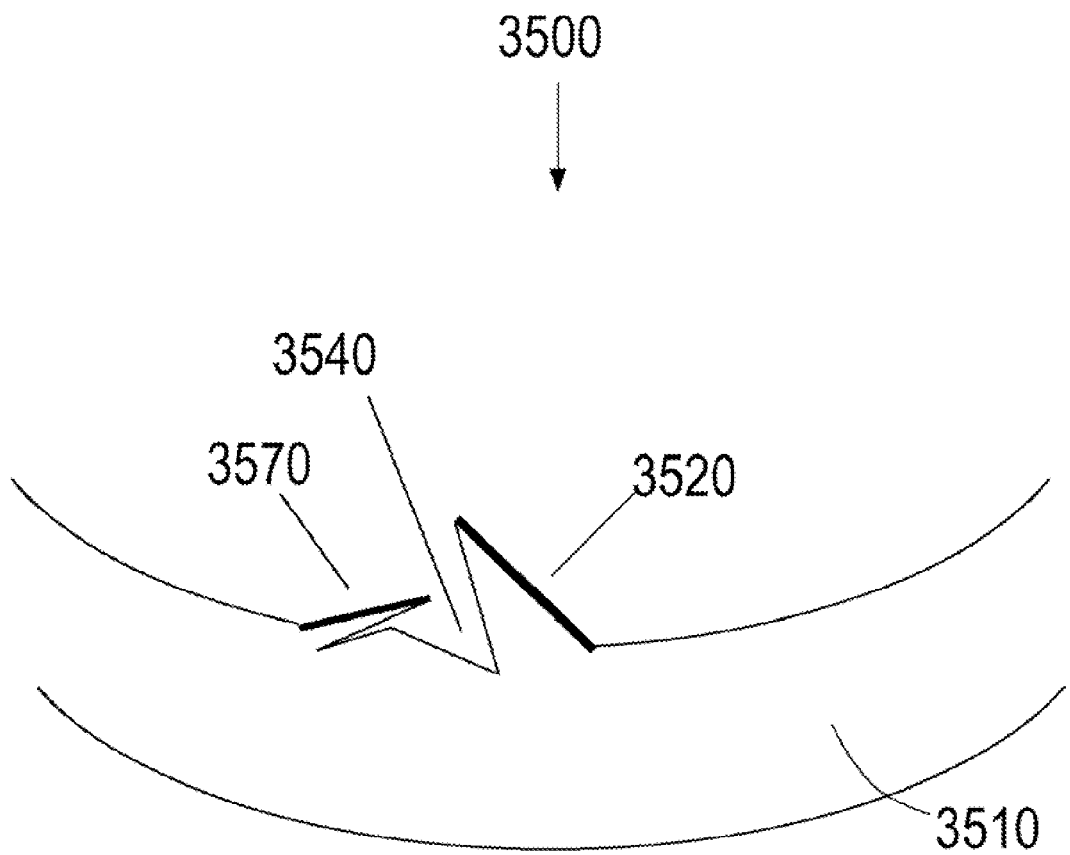
FIG. 25B shows a profile view of the embodiment of the invention of FIG. 25A in a different position.

Another embodiment of the pinched monofilament suture 3500 of the invention is depicted in FIG. 25A and FIG. 25B. In FIG. 25A, a retainer 3520 is formed in the suture core 3510 by, for example, cutting 3540 the retainer 3520 into outer sheath of the suture and/or the monofilament core 3510 using methods and procedures described herein. Additionally, adjacent to the retainer 3520, a retainer stop 3570 is formed in the core 3510. In this embodiment, the retainer stop 3570 can be formed with a forming technique that involves forming the retainer stop 3570 from the core 3510 in a direction opposite to the direction which was used to form the retainer 3520. Accordingly, the stop can be made in the outer sheath and/or the monofilament suture 3500 using methods and procedures described herein. As depicted in FIG. 25B when the suture is curved inwardly with respect to the retainer, the retainer stopper 3570 projects to a position below the retainer 3520 and prevents or stops the retainer 3520 from settling back into the space 3540 of the core 3510. Accordingly, even with the suture curved inwardly as depicted in FIG. 25B, the retainer is prominent enough to engage tissue when the suture is for example pulled in a direction opposite to the direction of the initial deployment of the suture in the tissue.

In various embodiments of the invention, incisions are cut into the fin using metal blades, sapphire blades, heating applied prior to cutting, heating applied during cutting and heating applied after cutting. In various embodiments of the invention, cuts into the fin vary in size, shape and angle of cut parameters so that the retainer can not be folded back against the core of the suture. In various embodiments of the invention, the cut is made using size, shape and angle of cut parameters so that the retainer strength is not diminished.

In various embodiments of the invention, the disposition of the retainers on the suture body can be ordered, e.g., staggered, spiral, overlapping, or random. Also, the retainers can be configured with a specific angle, depth, length and separation distance.

In an embodiment of the invention, a Monoderm (glycolide and e-caprolactone copolymer) monofilament suture can be coated with a stronger polymer coating to form, for example, a sheath as previously described. In another embodiment of the invention, a Monoderm monofilament suture can be coated with a more flexible polymer coating. In an embodiment of the invention, a PGA monofilament suture can be coated with a stronger polymer coating. In another embodiment of the invention, a PGA monofilament suture can be coated with a more flexible polymer coating.

In an embodiment of the invention, the resulting coated monofilament suture can be stronger than an uncoated monofilament suture although not necessarily as strong as a suture of the same size made from the material used to coat the monofilament suture. In an embodiment of the invention, the resulting coated monofilament suture can be stronger than a suture made from the material used to coat the monofilament suture, although not necessarily as strong as an uncoated monofilament suture of the same size. In an embodiment of the invention, the resulting coated monofilament suture can be more flexible than an uncoated monofilament suture although not necessarily as flexible as a suture of the same size made from the material used to coat the monofilament suture. In an embodiment of the invention, the resulting coated monofilament suture can be more flexible than a suture made from the material used to coat the monofilament suture, although not necessarily as flexible as an uncoated monofilament suture of the same size.

In an embodiment of the invention, a monofilament suture can be coated with a PDO polymer coating. In an embodiment of the invention, the resulting PDO coated monofilament suture can be stronger than an uncoated monofilament suture, although not necessarily as strong as a PDO suture of the same size. In an embodiment of the invention, the resulting PDO coated monofilament suture can be more flexible than an uncoated monofilament suture, although not necessarily as flexible as a PDO suture of the same size.

In an embodiment of the invention, a Monoderm monofilament suture can be coated with a PDO polymer coating. In an alternative embodiment of the invention, a PGA monofilament suture can be coated with a PDO polymer coating. In another embodiment of the invention, a PLAGA monofilament suture can be coated with a PDO polymer coating. In an alternative embodiment of the invention, a PLA monofilament suture can be coated with a PDO polymer coating.

In an embodiment of the invention, the resulting PDO coated Monoderm monofilament suture can be stronger than an uncoated Monoderm monofilament suture of the same size. In an embodiment of the invention, the resulting PDO coated Monoderm monofilament suture can be more flexible than an uncoated Monoderm monofilament suture of the same size. In an embodiment of the invention, the resulting PDO coated PGA monofilament suture can be stronger than an uncoated PGA monofilament suture of the same size. In an embodiment of the invention, the resulting PDO coated PGA monofilament suture can be more flexible than an uncoated PGA monofilament suture of the same size. In an alternative embodiment of the invention, the resulting PDO coated PLAGA monofilament suture can be stronger than an uncoated PLAGA monofilament suture of the same size. In an embodiment of the invention, the resulting PDO coated PLAGA monofilament suture can be more flexible than an uncoated PLAGA monofilament suture of the same size. In an alternative embodiment of the invention, the resulting PDO coated PLA monofilament suture can be stronger than an uncoated PLA monofilament suture of the same size. In an embodiment of the invention, the resulting PDO coated PLA monofilament suture can be more flexible than an uncoated PLA monofilament suture of the same size.

In various embodiments the retainers are cut to penetrate only the outer material. In an alternative embodiment of the invention, the retainers are cut through the outer material and the core material.

In differing embodiments of the invention, the sutures that can be modified according to the teachings of this invention include both degradable and non-degradable sutures.

In an alternative embodiment of the invention, the sutures can be coated with an antibacterial coatings either prior to or after modification to inhibit bacterial colonization with *Staphylococcus aureus*. The antibacterial agent used to coat the suture can be selected from the group consisting of cyanoalkylated hydroxypropylcellulose and triclosan.

Different sutures materials produce varying degrees of tissue reaction, specifically inflammation. Significant inflammation reduces the resistance to infection and delays the onset of wound healing. The type of material and size of the suture are thought to be the major factors contributing to this reaction. Natural materials can be absorbed mainly by proteolysis, causing a prominent inflammatory response, while synthetic materials can be absorbed mainly by hydrolysis, producing a minimal inflammatory reaction. Allergic reactions to suture materials or surgical adhesives are rare. Some reactions have been specifically associated with chromic catgut, when individuals are sensitive to the chromate ion.

In addition to the general wound closure and soft tissue repair applications described in the preceding sections, self-retaining sutures can be used in a variety of other indications.

Self-retaining sutures described herein may be used in various dental procedures, i.e., oral and maxillofacial surgical procedures and thus may be referred to as "self-retaining dental sutures." The above-mentioned procedures include, but are not limited to, oral surgery (e.g., removal of impacted or broken teeth), surgery to provide bone augmentation, surgery to repair dentofacial deformities, repair following trauma (e.g., facial bone fractures and injuries), surgical treatment of odontogenic and non-odontogenic tumors, reconstructive surgeries, repair of cleft lip or cleft palate, congenital craniofacial deformities, and esthetic facial surgery. Self-retaining dental sutures may be degradable or non-degradable, and may typically range in size from USP 2-0 to USP 6-0.

Self-retaining sutures described herein may also be used in tissue repositioning surgical procedures and thus may be referred to as "self-retaining tissue repositioning sutures". Such surgical procedures include, without limitation, face lifts, neck lifts, brow lifts, thigh lifts, and breast lifts. Self-retaining sutures used in tissue repositioning procedures may vary depending on the tissue being repositioned; for example, sutures with larger and further spaced-apart retainers may be suitably employed with relatively soft tissues such as fatty tissues.

Self-retaining sutures described herein may also be used in microsurgical procedures that are performed under a surgical microscope (and thus may be referred to as "self-retaining microsutures"). Such surgical procedures include, but are not limited to, reattachment and repair of peripheral nerves, spinal microsurgery, microsurgery of the hand, various plastic microsurgical procedures (e.g., facial reconstruction), microsurgery of the male or female reproductive systems, and various types of reconstructive microsurgery. Microsurgical reconstruction is used for complex reconstructive surgery problems when other options such as primary closure, healing by secondary intention, skin grafting, local flap transfer, and distant flap transfer are not adequate. Self-retaining microsutures have a very small caliber, often as small as USP 9-0 or USP 10-0, and may have an attached needle of corresponding size. They may be degradable or non-degradable.

Self-retaining sutures as described herein may be used in similarly small caliber ranges for ophthalmic surgical procedures and thus may be referred to as "ophthalmic self-retaining sutures". Such procedures include but are not limited to keratoplasty, cataract, and vitreous retinal microsurgical procedures. Ophthalmic self-retaining sutures may be degradable or non-degradable, and have an attached needle of correspondingly-small caliber.

Self-retaining sutures can be used in a variety of veterinary applications for a wide number of surgical and traumatic purposes in animal health.

Although the present invention has been shown and described in detail with regard to only a few exemplary embodiments of the invention, it should be understood by those skilled in the art that it is not intended to limit the invention to the specific embodiments disclosed. Various modifications, omissions, and additions may be made to the disclosed embodiments without materially departing from the novel teachings and advantages of the invention, particularly in light of the foregoing teachings. Accordingly, it is intended to cover all such modifications, omissions, additions, and equivalents as may be included within the spirit and scope of the invention as defined by the following claims.

What is claimed is:

1. A method of forming a self-retaining suture comprising the steps of:
    forming a plurality of retainers on an elongated suture body by inserting said suture into a retainer-forming machine, wherein said retainer-forming machine forms retainers in said suture; and
    performing a step of elevating the retainers away from the suture body, wherein the step of elevating the retainers comprises:
    after the retainers have been created by said retainer-forming machine, inserting the suture having retainers into an apparatus having at least one roller and at least one bending bar;
    drawing the suture through the apparatus over the at least one roller;
    and contacting the retainers with said at least one bending bar, wherein said bending bar physically applies a force to the retainers and bends the retainers back.

2. The method of claim 1 wherein the elevating step further comprises one or more of the following steps in addition to the step of contacting the retainers with at least one bending bar:
    applying mechanical energy to the retainers;
    applying thermal energy to the retainers;
    applying chemical energy to the retainers;
    applying electrostatic energy to the retainers;
    applying electrical energy to the retainers;
    applying elastic energy to the retainers;
    forming the retainers in a layer of material that is different that a core of the suture;
    coating the suture with a material that causes the retainers to become elevated;
    directing a fluid at the retainers; and
    applying a stress to one of the suture and the retainer.

3. The self-retaining suture system of claim 1 wherein the retainer is elevated using one or more of:
    applying mechanical energy to the retainers;
    applying thermal energy to the retainers;
    applying chemical energy to the retainers;
    applying electrostatic energy to the retainers;
    applying electrical energy to the retainers;
    applying elastic energy to the retainers;
    coating the suture with a material that causes the retainers to become elevated;
    directing a fluid at the retainers; and
    applying a stress to one of the suture and the retainer.

4. The method of claim 1, wherein the suture body comprises
    an inner core and an outer layer, and wherein the step of elevating the retainers further includes providing a transition stimuli to contract the outer layer thereby extending the retainers outwards away from the inner core.

5. The method of claim 4, wherein the outer layer is heat shrink tubing and the transition stimuli includes heating the heat shrink tubing.

6. The method of claim 4, wherein the inner core is a multifilament.

7. The method of claim 1, wherein the suture body further comprises an outer coating, and wherein the step of elevating the retainers further includes
    activating the coating to contract, the contraction of the coating causing the retainers to extend outwards away from the suture body.

8. The method of claim 7, wherein the coating is activated by a change in temperature.

9. The method of claim 7, further comprising adding an activator to contract the outer surface.

10. A method of forming a self-retaining suture comprising the steps of:
    forming a plurality of retainers on an elongated suture body; and
    performing a step of elevating the retainers away from the suture body, wherein the step of elevating the retainers comprises:
    inserting the suture having retainers into at least one hollow tube, said hollow tube having an inner surface having a retainer-engaging feature selected from the group consisting of dimples, grooves, bars or projections;
    drawing the suture through the at least one hollow tube; and
    bending the retainers back within the tube by dragging the retainers along the inner surface of the at least one hollow tube such that the retainers contact said retainer-engaging feature and said retainers are bent back.

11. The method of claim 10, which includes the further steps of:
    (a) drawing a first end of the suture through the tube in a first direction, wherein the retainers contact the inner surface of the tube between the first end of the suture and a transition segment of the suture, wherein the tube includes two separable halves, and wherein the suture is being drawn at a first speed;
    (b) separating the tube into two halves when the tube reaches the transition segment of the suture;
    (c) moving the two halves of the tube in a second direction opposite the first direction until the tube is located proximal to a second end of the suture;
    (d) connecting the separated halves of the tube back together proximal to the second end of the suture;
    (e) moving the tube in the first direction at a second speed until the tube reaches the transition segment of the suture, wherein the second speed is at least twice as fast as the first speed; and
    (f) separating the tube into two halves until the suture passes by the tube.

12. A method of forming a self-retaining suture comprising the steps of:
- forming a plurality of retainers on an elongated suture body, said plurality of retainers disposed in a spiral configuration about said elongated suture body; and
- performing a step of elevating the plurality of retainers away from the suture body, wherein the step of elevating the retainers comprises lifting the retainers from original elevation angles to increased elevation angles using electrostatic force.

13. The method of claim 12, wherein plastic deformation imposed by the lifting maintains the retainers at elevation angles greater than the original elevation angles.

14. The method of claim 12, wherein the retainers are made from a material that has a corresponding crystallization temperature, and further comprising:
- (d) annealing the retainers, while the retainers are lifted using electrostatic force, by increasing the temperature of the retainers to above the crystallization temperature of the material, and thereafter cooling the retainers.

15. The method of claim 14, wherein the step of elevating the retainers includes maintaining the temperature of the retainers above the crystallization temperature for a sufficient time to allow for stress-relaxation at the points where the retainers connect to the suture body.

16. The method of claim 12, wherein the retainers are made from a material that has a corresponding crystallization temperature, and further comprising annealing the retainers, after the retainers were lifted using electrostatic force, by increasing the temperature of the retainers to above the crystallization temperature of the material, and thereafter cooling the retainers.

17. The method of claim 12, further comprising a step of selectively annealing at least part of the retainers while or after the retainers are lifted using electrostatic force.

18. A method of forming a self-retaining suture comprising the steps of:
- forming a plurality of retainers on an elongated suture body; and
- performing a step of elevating the retainers away from the suture body, wherein the step of elevating the retainers comprises:
- contacting the suture body with a solution, wherein the solution expands the suture body extending the retainer out from the suture body; and
- applying a contractable film to the expanded suture body and contracting the film to fix the retainer in the extended position.

* * * * *